(12) United States Patent
Forsgren et al.

(10) Patent No.: US 7,981,434 B2
(45) Date of Patent: *Jul. 19, 2011

(54) **SURFACE EXPOSED IMMUNOGLOBULIN D-BINDING PROTEIN FROM *MORAXELLA CATARRHALIS***

(75) Inventors: Arne Forsgren, Falsterbo (SE); Kristian Riesbeck, Malmö (SE); Håkan Jansson, Lund (SE)

(73) Assignee: Arne Forsgren et al., Falsterbo (SE)

( * ) Notice: Subject to any disclaimer, the term of this patent is extended or adjusted under 35 U.S.C. 154(b) by 278 days.

This patent is subject to a terminal disclaimer.

(21) Appl. No.: 12/124,404

(22) Filed: May 21, 2008

(65) Prior Publication Data

US 2010/0098729 A1   Apr. 22, 2010

Related U.S. Application Data

(63) Continuation of application No. 10/480,456, filed as application No. PCT/SE02/01299 on Jul. 1, 2002, now Pat. No. 7,470,432.

(30) Foreign Application Priority Data

Jul. 4, 2001 (SE) ..................................... 0102410

(51) Int. Cl.
*A61K 39/10* (2006.01)
(52) U.S. Cl. ............... 424/254.1; 424/185.1; 424/190.1; 424/192.1; 435/4; 435/7.32
(58) Field of Classification Search .................. None
See application file for complete search history.

(56) References Cited

U.S. PATENT DOCUMENTS

| | | |
|---|---|---|
| 5,808,024 A | 9/1998 | Sasaki et al. |
| 6,214,981 B1 | 4/2001 | Tucker et al. |

FOREIGN PATENT DOCUMENTS

| | | |
|---|---|---|
| WO | WO 96/34960 | 11/1996 |
| WO | WO 01/05424 | 1/2001 |
| WO | WO 01/07619 | 2/2001 |

OTHER PUBLICATIONS

Forsgren et al., "Isolation and Characterization of Novel IgD-Binding Protein from *Moraxella catarrhalis*", The Journal of Immunology, vol. 167, 2001, pp. 2112 to 2120.
Forsgren et al., "*Branhamella catarrhalis* Activates Human B Lymphocytes Following Interactions with Surface IgD and Class 1 Major Histocompatibility Complex Antigens", Cellular Immunology, vol. 112, 1988, pp. 78 to 88.
Tedder, "Immunoglobulin D-Binding Bacteria", Bacterial Immunoglobulin-Binding Proteins, vol. 1, 1990, pp. 235 to 242.
Mikayama et al., Proc. Natl. Acad. Sci., vol. 90, pp. 10056-10060, Nov. 1993.
Rudinger et al., Peptide Hormones, Biol. Council, pp. 1-7, Jun. 1976.
Murphy et al., Pediatr. Infect. Dis. J., vol. 8, pp. S66-S68, 1989.
Yamanaka et al., J. Pediatrics, vol. 122, No. 2, pp. 212-218, 1993.

*Primary Examiner* — Jennifer Graser
(74) *Attorney, Agent, or Firm* — Buchanan Ingersoll & Rooney PC

(57) ABSTRACT

The present invention relates to a surface exposed protein, which can be detected in *Moraxella catarrhalis*, having an amino acid sequence as described in SEQ ID NO: 1, an apparent molecular weight of 200 kDa and a capacity of selectively binding membrane bound or soluble IgD, to an immunogenic or IgD-binding fragment of said surface exposed protein, and to an immunogenic and adhesive fragment of said surface exposed protein. DNA segments, vaccines, plasmids and phages, non human hosts, recombinant DNA molecules and plants, fusion proteins and polypeptides and fusion products are also described. A method of detecting IgD, a method of separating IgD, a method of isolation of a surface exposed protein of *Moraxella catarrhalis* and a method for treatment of an autoimmune disease are also disclosed.

17 Claims, 26 Drawing Sheets

```
-250
ACTCTATTATTTGATATGTTTTGAAACTAATCTATTGACTTAAATCACCATATGGTTATAAT

TTAGCATAATGGTAGGCTTTTTGTAAAAATCACATCGCAATATTGTTCTACTGTTACTACCA
    -35
TGCTTGAATGACGATCCCAATCATCAGATTCATTCAAGTGATGTGTTTGTATACGCATCATT
   -10                                                     rbs
TACCCTAATTATTTCAATCGAAATGCCTATGTCAGCATGTATCATTTTTTTAAGGTAAACCA
    1/1                                    31/11
CC ATG AAT CAC ATC TAT AAA GTC ATC TTT AAC AAA GCC ACA GGC ACA
   Met asn his ile tyr lys val ile phe asn lys ala thr gly thr
                          61/21
TTT ATG GCC GTG GCG GAA TAT GCC AAA TCC CAC AGC ACG GGG GGT
phe Met ala val ala glu tyr ala lys ser his ser thr gly gly
 91/31                                      121/41
AGC TGT GCT ACA GGG CAA GTT GGC AGT GTA TGC ACT CTG AGC TTT
ser cys ala thr gly gln val gly ser val cys thr leu ser phe
                          151/51
GCC CGT GTT GCC GCG CTC GCT GTC CTC GTG ATC GGT GCG ACG CTC
ala arg val ala ala leu ala val leu val ile gly ala thr leu
181/61                                      211/71
AAT GGC AGT GCT TAT GCT CAA CAA GAT CCC AGA CAT ATC GCA ATT
asn gly ser ala tyr ala gln gln asp pro arg his ile ala ile
                          241/81
GAT GGC AAC AGC TCG AAC ACA TCC TCA GGC ACT GCC CGT GCG ACA
asp gly asn ser ser asn thr ser ser gly thr ala arg ala thr
271/91                                      301/101
GGT GAT CGA GCC ATT GCT CTT GGT GAA AAT GCT AAT GCA GAG GGC
gly asp arg ala ile ala leu gly glu asn ala asn ala glu gly
                          331/111
GGT CAA GCC ATC GCC ATC GGT AGT AGC AAT AAA ACA GGT GGT AGA
gly gln ala ile ala ile gly ser ser asn lys thr gly gly arg
361/121                                     391/131
AAC GCG CTG AAT ATA GGT ACC GAT GCC AAA GGT GAG GAG TCC ATC
asn ala leu asn ile gly thr asp ala lys gly glu glu ser ile
                          421/141
GCC ATC GGT GGT GAT GTA GTG GCT GAG GGT ACT GCC TCG ATT GCC
ala ile gly gly asp val val ala glu gly thr ala ser ile ala
451/151                                     481/161
ATC GGT GGT GAT GAC TTA CAT TTG TGG GAT GAA CCA AAT AAG CAA
ile gly gly asp asp leu his leu trp asp glu pro asn lys gln
```

Fig 6

```
                        511/171
AAG TTC CTC GAC CCA AAA GTT AAA GAA TTG ATT TTA AAA CAT CAA
lys phe leu asp pro lys val lys glu leu ile leu lys his gln
541/181                                 571/191
GAA TTA AAC AAC ATA TAC AAA CTG CCT GAT GGT AGT CCT CAA AGA
glu leu asn asn ile tyr lys leu pro asp gly ser pro gln arg
                        601/201
TAT TTT CGC ACA TAC GCA AAG GGA CAC GCC AGT ATT GCA CTA GGA
tyr phe arg thr tyr ala lys gly his ala ser ile ala leu gly
631/211                                 661/221
ACC ATG ACA CAG GCA GAG GGT CAT TTT GCC AAC GCC TTT GGT ACA
thr met thr gln ala glu gly his phe ala asn ala phe gly thr
                        691/231
CGG GCA ACA GCT AAA GGC AAC TAT TCC TTG GCA GTG GGT CTT ACC
arg ala thr ala lys gly asn tyr ser leu ala val gly leu thr
721/241                                 751/251
GCC CAA GCC AAC ACA GAA TCT TCA ATC GCT GTT GGT TCT AAT GCA
ala gln ala asn thr glu ser ser ile ala val gly ser asn ala
                        781/261
CAA GCT AAC GGG TTT GCA GCG ACA GCC ATT GGT GGA GGT ACT AAA
gln ala asn gly phe ala ala thr ala ile gly gly gly thr lys
811/271                                 841/281
GCT GAT TTG GGT CGA AGC ATA GCC CTA GGT TTT GGT TCT CAG ATC
ala asp leu gly arg ser ile ala leu gly phe gly ser gln ile
                        871/291
CTT ACT AAG GAG AAG GAT AGT CAT AAC AAT ACC AAT GTC TAT GTA
leu thr lys glu lys asp ser his asn asn thr asn val tyr val
901/301                                 931/311
CCA CAA GGT GAA ATA TTA GAA GAG CGG TAT AAA GCC ACC GAA AAC
pro gln gly glu ile leu glu glu arg tyr lys ala thr glu asn
                        961/321
GGT CAG TCG CCT AAT AAG GTA GTG GAT ATA TTT TCC ATT GGT AGT
gly gln ser pro asn lys val val asp ile phe ser ile gly ser
991/331                                 1021/341
AGC TCT ATC AAA CGT AAA ATC ATC AAT GTC GGT GCG GGT TCT CAG
ser ser ile lys arg lys ile ile asn val gly ala gly ser gln
                        1051/351
GAG ACC GAT GCG GTC AAT GTG GCA CAG CTT AAA TTG GTG GAG CGG
glu thr asp ala val asn val ala gln leu lys leu val glu arg
```

Fig 6 cont

```
1081/361                                    1111/371
GTG GCT AAG CGT CAA ATT ACT TTT CAG GGT GAT GAT AGC AAT AAT
val ala lys arg gln ile thr phe gln gly asp asp ser asn asn
                         1141/381
AGC GTA AAA AAA GGT TTG GGT CAG ACT TTA ACT ATT AAA GGT GGT
ser val lys lys gly leu gly gln thr leu thr ile lys gly gly
1171/391                                    1201/401
AAA ACA GAG ACC GGT GAA CTA ACC GAA AAT AAC ATC GGT GTG GTA
lys thr glu thr gly glu leu thr glu asn asn ile gly val val
                         1231/411
CAA GAT GAT AAT GGT AAT GGT CTG AAA GTT AAA CTT GCT AAA GAT
gln asp asp asn gly asn gly leu lys val lys leu ala lys asp
1261/421                                    1291/431
CTG ACT GGT TTG ACC AAG GTT GCA GTA AAT GGT AAT GGT GCT AAC
leu thr gly leu thr lys val ala val asn gly asn gly ala asn
                         1321/441
AAC GCC GAG CTA CTA AAC GGT GGT CTG ACC TTT TCG ACA TCA GGT
asn ala glu leu leu asn gly gly leu thr phe ser thr ser gly
1351/451                                    1381/461
GCC AAT GCA GGC AAA ACG GTC TAT GGC ACT GAT GGG GTG AAG TTT
ala asn ala gly lys thr val tyr gly thr asp gly val lys phe
                         1411/471
ACT AAT AAT ACA GGA ACA GGA ACA GGA ACG GCA ATA CCC GAC ACT
thr asn asn thr gly thr gly thr gly thr ala ile pro asp thr
1441/481                                    1471/491
ACT CGT ATT ACC AAA AAT AAA ATT GGC TTT GCT GGG GCT GAT GAA
thr arg ile thr lys asn lys ile gly phe ala gly ala asp glu
                         1501/501
CAA GTT GAT GAA AGC AAA CCT TAT CTT GAC AAC GAA AAG CTA AAA
gln val asp glu ser lys pro tyr leu asp asn glu lys leu lys
1531/511                                    1561/521
GTT GGC ACA GTT GAG ATT AAA AAA ACT GGC ATC AAT GCA GGT AAT
val gly thr val glu ile lys lys thr gly ile asn ala gly asn
                         1591/531
CAA GAA ATT ACC AAG GTC AAA TCT GCC ATT GTT GAT GCA GTT AAT
gln glu ile thr lys val lys ser ala ile val asp ala val asn
1621/541                                    1651/551
GGA CAA GCA AAT CAA AGC TTT GTG AAC CTT CTA GAA ACA GCA GGC
gly gln ala asn gln ser phe val asn leu leu glu thr ala gly
                         1681/561
ACA AAC ACC AAC AAA CAA AAC TCT GCC GCC ACG GTT AAA GAC TTA
thr asn thr asn lys gln asn ser ala ala thr val lys asp leu
```

Fig 6 cont

```
1711/571                                1741/581
TAC GAC CTA TCA CAA TCA CCG CTG ACC TTT ACA GGT GAT AGC GGT
tyr asp leu ser gln ser pro leu thr phe thr gly asp ser gly
                              1771/591
AAC GTT AAG AGA AAA CTG GGT CAG ACT TTA ACC ATC ACA GGC GGA
asn val lys arg lys leu gly gln thr leu thr ile thr gly gly
1801/601                                1831/611
CAA ACA AAG ACC GAT CAA TTA ACC GAC AAT AAC ATC GGT GTG GTA
gln thr lys thr asp gln leu thr asp asn asn ile gly val val
                              1861/621
GCA GGT ACT AAT GGC TTA ACC GTT AAA CTT GCT AAA ACT TTA AAC
ala gly thr asn gly leu thr val lys leu ala lys thr leu asn
1891/631                                1921/641
AGT CTT ACT GAA GTT AAT ACG GCT ACA TTA AAC GCC ACC AAT AAA
ser leu thr glu val asn thr ala thr leu asn ala thr asn lys
                              1951/651
GTT AAG GTA GAT AAT AGT ACT GGT AAT ACG GCT GAA TTA TTA AAC
val lys val asp asn ser thr gly asn thr ala glu leu leu asn
1981/661                                2011/671
AAT GGT TTA ACC TTT ACC CAA ACA ACA GGT GCA AAT TCA GGT AAA
asn gly leu thr phe thr gln thr thr gly ala asn ser gly lys
                              2041/681
ACC GTC TAT GGC AAT GAT GGC TTG AAG TTT ACT AAT AGT GCT AAT
thr val tyr gly asn asp gly leu lys phe thr asn ser ala asn
2071/691                                2101/701
AAA GCA CTT GGC GGC ACA ACT TAC ATC ACC AAA GAT CAA GTT GGT
lys ala leu gly gly thr thr tyr ile thr lys asp gln val gly
                              2131/711
TTT AGC AAT CAA GAT GGC TTA CTT GAT GAA AGC AAA CCG TAT CTT
phe ser asn gln asp gly leu leu asp glu ser lys pro tyr leu
2161/721                                2191/731
AAC CGA GAA AAG CTA AAA GTT GGT AAA ATT GAG ATT AAA GAC AGT
asn arg glu lys leu lys val gly lys ile glu ile lys asp ser
                              2221/741
GGC ATT AAT GCA GGT GGT AAA GCC ATC ACA GGA CTG CCC TCA ACA
gly ile asn ala gly gly lys ala ile thr gly leu pro ser thr
2251/751                                2281/761
CTG CCC AAC ACT ACC TAT ACT GCA CCT GGC GTG CAT ACT GCA CTA
leu pro asn thr thr tyr thr ala pro gly val his thr ala leu
                              2311/771
CAT GGC AGT ACA ATT TCT AAC GAC GAC AAA ACC CGT GCC GCC AGT
his gly ser thr ile ser asn asp asp lys thr arg ala ala ser
```

Fig 6 cont

```
2341/781                                  2371/791
ATC GCC GAT GTG CTA AAC GCA GGC TTT AAC TTG GAA GGT AAT GGT
ile ala asp val leu asn ala gly phe asn leu glu gly asn gly
                         2401/801
GAA GCG GTT GAC TTT GTC TCC ACT TAT GAC ACC GTC AAC TTT GCC
glu ala val asp phe val ser thr tyr asp thr val asn phe ala
2431/811                                  2461/821
GAT GGC AAT GCC ACC ACC GCT AAG GTA ACT TAT GAT AAC AAA ACC
asp gly asn ala thr thr ala lys val thr tyr asp asn lys thr
                         2491/831
AGT AAA GTG GCG TAT GAT GTC AAT GTG GAT GGT ACA ACC ATT CAT
ser lys val ala tyr asp val asn val asp gly thr thr ile his
2521/841                                  2551/851
CTA ACA GGC ACT AAT GGC AAG AAA AAC CAA ATT GGC GTA AAA ACC
leu thr gly thr asn gly lys lys asn gln ile gly val lys thr
                         2581/861
ACC ACA CTG ACC ACA AAA CGT GCT AAA GGT AAT ACA GCA ACT AAT
thr thr leu thr thr lys arg ala lys gly asn thr ala thr asn
2611/871                                  2641/881
TTT AGT GTT AAC TCT GGT GAT GAC AAT GCC CTT ATT AAC GCC AAA
phe ser val asn ser gly asp asp asn ala leu ile asn ala lys
                         2671/891
GAC ATC GCC GAC AAT CTA AAC ACC CTA GCT GGT GAA ATT CGC ACC
asp ile ala asp asn leu asn thr leu ala gly glu ile arg thr
2701/901                                  2731/911
GCC AAA GGC ACA GCA AGC ACC GCC CTA CAA ACC TTC TCT ATT ATT
ala lys gly thr ala ser thr ala leu gln thr phe ser ile ile
                         2761/921
GAT GAA CAA GGT AAT AAC TTT ATG GTC GGT AAC CTT TAC TCT GGT
asp glu gln gly asn asn phe met val gly asn leu tyr ser gly
2791/931                                  2821/941
TAT GAC ACC TCA AAT ACC TCT GAG ACC GTC ACC TTT GTA GGT GAA
tyr asp thr ser asn thr ser glu thr val thr phe val gly glu
                         2851/951
AAC GGC ATT ACC ACC AAG GTA AAT AAA GGT AAA GTC AAA GTT GGT
asn gly ile thr thr lys val asn lys gly lys val lys val gly
2881/961                                  2911/971
ATT GAC CAA ACC AAA GGC TTA ACC ACG CCT AAG CTG ACC GTG GGT
ile asp gln thr lys gly leu thr thr pro lys leu thr val gly
                         2941/981
AGT AGT AAT GGC AAA GGC ATT GTC ATT GAC AGT AAA GAT GGT CAA
ser ser asn gly lys gly ile val ile asp ser lys asp gly gln
```

Fig 6 cont

```
2971/991                                    3001/1001
AAT ACC ATC ACA GGA CTA AGC AAC ACT CTA ACC GAT GCC ACC AAC
asn thr ile thr gly leu ser asn thr leu thr asp ala thr asn
                           3031/1011
GCA ACA ACA GGG CAT GTC AGT GAA ATC CAG GGC TTG GCA CAA GGT
ala thr thr gly his val ser glu ile gln gly leu ala gln gly
3061/1021                                   3091/1031
GCA AAC AAA ACC CGT GCC GCC AGC ATT GGT GAT GTA CTA AAC GCA
ala asn lys thr arg ala ala ser ile gly asp val leu asn ala
                           3121/1041
GGC TTT AAC TTG CAA GGC AAT GGT GAA GCC AAA GAC TTT GTC TCC
gly phe asn leu gln gly asn gly glu ala lys asp phe val ser
3151/1051                                   3181/1061
ACT TAT GAC ACC GTC AAC TTT ATC GAT GGC AAT GCC ACC ACC GCT
thr tyr asp thr val asn phe ile asp gly asn ala thr thr ala
                           3211/1071
AAG GTG ACC TAT GAT GAC ACG AAA CAG ACC AGC ACA GTA ACT TAT
lys val thr tyr asp asp thr lys gln thr ser thr val thr tyr
3241/1081                                   3271/1091
GAT GTC AAT GTG GAT AAT AAA ACC CTT GAA GTG ACA GGC GAT AAA
asp val asn val asp asn lys thr leu glu val thr gly asp lys
                           3301/1101
AAA CTT GGC GTC AAA ACC ACC ACA CTG ACC AAA ACA AGT GCT AAT
lys leu gly val lys thr thr thr leu thr lys thr ser ala asn
3331/1111                                   3361/1121
GGT AAT GCA ACC AAA TTT AGT GCC GCC GAT GGC GAT GCC CTT GTT
gly asn ala thr lys phe ser ala ala asp gly asp ala leu val
                           3391/1131
AAA GCC AGT GAT ATC GCC ACC CAT CTA AAT ACC TTG GCT GGC GAC
lys ala ser asp ile ala thr his leu asn thr leu ala gly asp
3421/1141                                   3451/1151
ATC CAA ACC GCC AAA GGA GCA AGC CAA GCA AGC AGC TCA GCA AGC
ile gln thr ala lys gly ala ser gln ala ser ser ser ala ser
                           3481/1161
TAT GTG GAT GCT GAT GGC AAC AAG GTC ATC TAT GAC AGT ACC GAT
tyr val asp ala asp gly asn lys val ile tyr asp ser thr asp
```

Fig 6 cont

```
3511/1171                                    3541/1181
AAG AAG TAC TAT CAA GCC AAA AAT GAT GGC ACA GTT GAT AAA ACC
lys lys tyr tyr gln ala lys asn asp gly thr val asp lys thr
                              3571/1191
AAA GAA GTT GCC AAA GAC AAA CTG GTC GCC CAA GCC CAA ACC CCA
lys glu val ala lys asp lys leu val ala gln ala gln thr pro
3601/1201                                    3631/1211
GAT GGC ACA TTG GCT CGA ATG AAT GTC AAA TCA GTC ATT AAC AAA
asp gly thr leu ala arg met asn val lys ser val ile asn lys
                              3661/1221
GAA CAA GTA AAT GAT GCC AAT AAA AAG CAA GGC ATC AAC GAA GAC
glu gln val asn asp ala asn lys lys gln gly ile asn glu asp
3691/1231                                    3721/1241
AAC GCC TTT GTT AAA GGA CTT GAA AAA GCC GCT TCT GAT AAC AAA
asn ala phe val lys gly leu glu lys ala ala ser asp asn lys
                              3751/1251
ACC AAA AAC GCC GCA GTA ACT GTG GGT GAT TTA AAT GCC GTT GCC
thr lys asn ala ala val thr val gly asp leu asn ala val ala
3781/1261                                    3811/1271
CAA ACA CCG CTG ACC TTT GCA GGG GAT ACA GGC ACA ACG GCT AAA
gln thr pro leu thr phe ala gly asp thr gly thr thr ala lys
                              3841/1281
AAA CTG GGC GAG ACT TTG ACC ATC AAA GGT GGG CAA ACA GAC ACC
lys leu gly glu thr leu thr ile lys gly gly gln thr asp thr
3871/1291                                    3901/1301
AAT AAG CTA ACC GAT AAT AAC ATC GGT GTG GTA GCA GGT ACT GAT
asn lys leu thr asp asn asn ile gly val val ala gly thr asp
                              3931/1311
GGC TTC ACT GTC AAA CTT GCC AAA GAC CTA ACC AAT CTT AAC AGC
gly phe thr val lys leu ala lys asp leu thr asn leu asn ser
3961/1321                                    3991/1331
GTT AAT GCA GGT GGC ACC AAA ATT GAT GAC AAA GGC GTG TCT TTT
val asn ala gly gly thr lys ile asp asp lys gly val ser phe
                              4021/1341
GTA GAC GCA AAC GGT CAA GCC AAA GCA AAC ACC CCT GTG CTA AGT
val asp ala asn gly gln ala lys ala asn thr pro val leu ser
4051/1351                                    4081/1361
GCC AAT GGG CTG GAC CTG GGT GGC AAA CGC ATC AGT AAC ATC GGT
ala asn gly leu asp leu gly gly lys arg ile ser asn ile gly
```

Fig 6 cont

```
                      4111/1371
GCA GCT GTT GAT GAT AAC GAT GCG GTG AAC TTT AAG CAG TTT AAT
ala ala val asp asp asn asp ala val asn phe lys gln phe asn
4141/1381                                       4171/1391
GAA GTT GCC AAA ACG GTC AAC AAC CTA AAC AAC CAA AGT AAC TCA
glu val ala lys thr val asn asn leu asn asn gln ser asn ser
                      4201/1401
GGT GCG TCA TTG CCC TTT GTA GTA ACC GAT GCC AAT GGC AAG CCC
gly ala ser leu pro phe val val thr asp ala asn gly lys pro
4231/1411                                       4261/1421
ATC AAT GGC ACC GAT GAC AAG CCC CAA AAA GCC ATC AAG GGC GCC
ile asn gly thr asp asp lys pro gln lys ala ile lys gly ala
                      4291/1431
GAT GGT AAA TAC TAT CAC GCC AAC GCC AAC GGC GTA CCT GTG GAC
asp gly lys tyr tyr his ala asn ala asn gly val pro val asp
4321/1441                                       4351/1451
AAA GAT GGC AAC CCC ATC ACC GAT GCG GAC AAA CTT GCC AAT CTG
lys asp gly asn pro ile thr asp ala asp lys leu ala asn leu
                      4381/1461
GCA GCT CAT GGC AAA CCC CTT GAT GCA GGT CAT CAA GTG GTG GCA
ala ala his gly lys pro leu asp ala gly his gln val val ala
4411/1471                                       4441/1481
AGC CTA GGC GGC AAC TCA GAT GCC ATC ACC CTA ACC AAC ATC AAG
ser leu gly gly asn ser asp ala ile thr leu thr asn ile lys
                      4471/1491
TCC ACT TTG CCA CAA ATT GAC ACA CCA AAC ACA GGT AAT GCC AAT
ser thr leu pro gln ile asp thr pro asn thr gly asn ala asn
4501/1501                                       4531/1511
GCA GGG CAA GCC CAA AGT CTG CCC AGC CTA TCA GCA GCA CAG CAA
ala gly gln ala gln ser leu pro ser leu ser ala ala gln gln
                      4561/1521
AGT AAT GCT GCC AGT GTC AAA GAT GTG CTA AAT GTA GGC TTT AAC
ser asn ala ala ser val lys asp val leu asn val gly phe asn
4591/1531                                       4621/1541
TTG CAG ACC AAT CAC AAT CAA GTG GAC TTT GTC AAA GCC TAT GAT
leu gln thr asn his asn gln val asp phe val lys ala tyr asp
                      4651/1551
ACC GTC AAC TTT GTC AAT GGT ACA GGT GCC GAC ATC ACA AGC GTG
thr val asn phe val asn gly thr gly ala asp ile thr ser val
```

Fig 6 cont

```
4681/1561                                    4711/1571
CGT AGT GCT GAT GGC ACG ATG AGT AAC ATC ACC GTC AAC ACC GCC
arg ser ala asp gly thr met ser asn ile thr val asn thr ala
                         4741/1581
TTA GCA GCG ACC GAT GAT GAT GGC AAT GTG CTT ATC AAA GCC AAA
leu ala ala thr asp asp asp gly asn val leu ile lys ala lys
4771/1591                                    4801/1601
GAT GGT AAG TTC TAC AAA GCA GAC GAC CTC ATG CCA AAC GGC TCA
asp gly lys phe tyr lys ala asp asp leu met pro asn gly ser
                         4831/1611
CTA AAA GCA GGC AAA TCA GCC AGT GAT GCC AAA ACT CCA ACT GGT
leu lys ala gly lys ser ala ser asp ala lys thr pro thr gly
4861/1621                                    4891/1631
CTA AGC CTT GTC AAC CCC AAT GCT GGT AAA GGC AGT ACA GGC GAT
leu ser leu val asn pro asn ala gly lys gly ser thr gly asp
                         4921/1641
GCA GTG GCT CTT AAT AAC TTA TCA AAA GCG GTA TTT AAA TCC AAA
ala val ala leu asn asn leu ser lys ala val phe lys ser lys
4951/1651                                    4981/1661
GAT GGT ACA ACT ACT ACC ACA GTA AGC TCT GAT GGC ATC AGT ATC
asp gly thr thr thr thr thr val ser ser asp gly ile ser ile
                         5011/1671
CAA GGC AAA GAT AAC AGC AAC ATC ACC CTA AGC AAA GAT GGG CTG
gln gly lys asp asn ser asn ile thr leu ser lys asp gly leu
5041/1681                                    5071/1691
AAT GTA GGC GGT AAG GTC ATC AGC AAT GTG GGT AAA GGC ACA AAA
asn val gly gly lys val ile ser asn val gly lys gly thr lys
                         5101/1701
GAC ACC GAC GCT GCC AAT GTA CAA CAG TTA AAC CGA AGT ACG CAA
asp thr asp ala ala asn val gln gln leu asn arg ser thr gln
5131/1711                                    5161/1721
CTT GTT GGG TCT TGG GTA ATG GCT GGT AAT GAT AAC GCT GAC GGC
leu val gly ser trp val met ala gly asn asp asn ala asp gly
                         5191/1731
AAT CAG GTA AAC ATT GCC GAC ATC AAA AAA GAC CCA AAT TCA GGT
asn gln val asn ile ala asp ile lys lys asp pro asn ser gly
5221/1741                                    5251/1751
TCA TCA TCT AAC CGC ACT GTC ATC AAA GCA GGC ACG GTA CTT GGC
ser ser ser asn arg thr val ile lys ala gly thr val leu gly
                         5281/1761
GGT AAA GGT AAT AAC GAT ACC GAA AAA CTT GCC ACT GGT GGT GTA
gly lys gly asn asn asp thr glu lys leu ala thr gly gly val
```

Fig 6 cont

```
5311/1771                                         5341/1781
CAA GTG GGC GTG GAT AAA GAC GGC AAC GCT AAC GGC GAT TTA AGC
gln val gly val asp lys asp gly asn ala asn gly asp leu ser
                                  5371/1791
AAT GTT TGG GTC AAA ACC CAA AAA GAT GGC AGC AAA AAA GCC CTG
asn val trp val lys thr gln lys asp gly ser lys lys ala leu
5401/1801                                         5431/1811
CTC GCC ACT TAT AAC GCC GCA GGT CAG ACC AAC TAT TTG ACC AAC
leu ala thr tyr asn ala ala gly gln thr asn tyr leu thr asn
                                  5461/1821
AAC CCC GCA GAA GCC ATT GAC AGA ATA AAT GAA CAA GGT ATC CGC
asn pro ala glu ala ile asp arg ile asn glu gln gly ile arg
5491/1831                                         5521/1841
TTC TTC CAT GTC AAC GAT GGC AAT CAA GAG CCT GTG GTA CAA GGG
phe phe his val asn asp gly asn gln glu pro val val gln gly
                                  5551/1851
CGT AAC GGC ATT GAC TCA AGT GCC TCA GGC AAG CAC TCA GTG GCG
arg asn gly ile asp ser ser ala ser gly lys his ser val ala
5581/1861                                         5611/1871
GTC GGT TAT AAG GCC AAG GCA GAT GGT GAA GCC GCC GTT GCC ATA
val gly tyr lys ala lys ala asp gly glu ala ala val ala ile
                                  5641/1881
GGC AGA CAA ACC CAA GCA GGC AAC CAA TCC ATC GCC ATC GGT GAT
gly arg gln thr gln ala gly asn gln ser ile ala ile gly asp
5671/1891                                         5701/1901
AAC GCA CAA GCC ACA GGC GAT CAA TCC ATC GCC ATC GGT ACA GGC
asn ala gln ala thr gly asp gln ser ile ala ile gly thr gly
                                  5731/1911
AAT GTG GTA GCA GGT AAG CAC TCT GGT GCC ATC GGC GAC CCA AGC
asn val val ala gly lys his ser gly ala ile gly asp pro ser
5761/1921                                         5791/1931
ACT GTT AAG GCT GAT AAC AGT TAC AGT GTG GGT AAT AAC AAC CAG
thr val lys ala asp asn ser tyr ser val gly asn asn asn gln
                                  5821/1941
TTT ACC GAT GCC ACT CAG ACC GAT GTC TTT GGT GTG GGC AAT AAC
phe thr asp ala thr gln thr asp val phe gly val gly asn asn
5851/1951                                         5881/1961
ATC ACC GTG ACC GAA AGT AAC TCG GTT GCC TTA GGT TCA AAC TCT
ile thr val thr glu ser asn ser val ala leu gly ser asn ser
```

Fig 6 cont

```
                           5911/1971
GCC ATC AGT GCA GGC ACA CAC GCA GGC ACA CAA GCC AAA AAA TCT
ala ile ser ala gly thr his ala gly thr gln ala lys lys ser
5941/1981                                      5971/1991
GAC GGC ACA GCA GGT ACA ACC ACC ACA GCA GGT GCA ACA GGT ACG
asp gly thr ala gly thr thr thr thr ala gly ala thr gly thr
                           6001/2001
GTT AAA GGC TTT GCT GGA CAA ACG GCG GTT GGT GCG GTC TCC GTG
val lys gly phe ala gly gln thr ala val gly ala val ser val
6031/2011                                      6061/2021
GGT GCC TCA GGT GCT GAA CGC CGT ATC CAA AAT GTG GCA GCA GGT
gly ala ser gly ala glu arg arg ile gln asn val ala ala gly
                           6091/2031
GAG GTC AGT GCC ACC AGC ACC GAT GCG GTC AAT GGT AGC CAG TTG
glu val ser ala thr ser thr asp ala val asn gly ser gln leu
6121/2041                                      6151/2051
TAC AAA GCC ACC CAA AGC ATT GCC AAC GCA ACC AAT GAG CTT GAC
tyr lys ala thr gln ser ile ala asn ala thr asn glu leu asp
                           6181/2061
CAT CGT ATC CAC CAA AAC GAA AAT AAA GCC AAT GCA GGG ATT TCA
his arg ile his gln asn glu asn lys ala asn ala gly ile ser
6211/2071                                      6241/2081
TCA GCG ATG GCG ATG GCG TCC ATG CCA CAA GCC TAC ATT CCT GGC
ser ala met ala met ala ser met pro gln ala tyr ile pro gly
                           6271/2091
AGA TCC ATG GTT ACC GGG GGT ATT GCC ACC CAC AAC GGT CAA GGT
arg ser met val thr gly gly ile ala thr his asn gly gln gly
6301/2101                                      6331/2111
GCG GTG GCA GTG GGA CTG TCG AAG CTG TCG GAT AAT GGT CAA TGG
ala val ala val gly leu ser lys leu ser asp asn gly gln trp
                           6361/2121
GTA TTT AAA ATC AAT GGT TCA GCC GAT ACC CAA GGC CAT GTA GGG
val phe lys ile asn gly ser ala asp thr gln gly his val gly
6391/2131
GCA GCA GTT GGT GCA GGT TTT CAC TTT TAA GCCATAAATCGC
ala ala val gly ala gly phe his phe stop

AGATTTTACTTAAAAATCAATCTCACCATAGTTGTATAAAACAGCATCA inverted repeat                                   6505
GCATCAGTCATATTACTGATGCTTGATGGTTTTTATTACTTAAACCATTTTA
```

|  | Bc5 | BBH17 | Perez112 | RH1 | RH4 | ATCC 25238; UspA1 | ATCC 25238; UspA2 |
|---|---|---|---|---|---|---|---|
| Bc5 | 100 %<br>100 % | | | | | | |
| BBH17 | 83.5 %<br>88.1 % | 100 %<br>100 % | | | | | |
| Perez112 | 79.2 %<br>82.6 % | 78.3 %<br>81.4 % | 100 %<br>100 % | | | | |
| RH1 | 75.8 %<br>80.2 % | 76.3 %<br>79.6 % | 85.0 %<br>89.1 % | 100 %<br>100 % | | | |
| RH4 | 65.6 %<br>71.3 % | 65.3 %<br>71.2 % | 68.0 %<br>72.9 % | 67.7 %<br>71.7 % | 100 %<br>100 % | | |
| ATCC 25238; UspA1 | 11.1 %<br>17.9 % | 9.5 %<br>14.9 % | 11.1 %<br>17.5 % | 5.5 %<br>8.3 % | 10.0 %<br>15.6 % | 100 %<br>100 % | |
| ATCC 25238; UspA2 | 6.7 %<br>12.1 % | 6.7 %<br>11.1 % | 7.5 %<br>12.4 % | 7.3 %<br>12.4 % | 6.5 %<br>11.1 % | 28.8 %<br>38.3 % | 100 %<br>100 % |

Fig 7

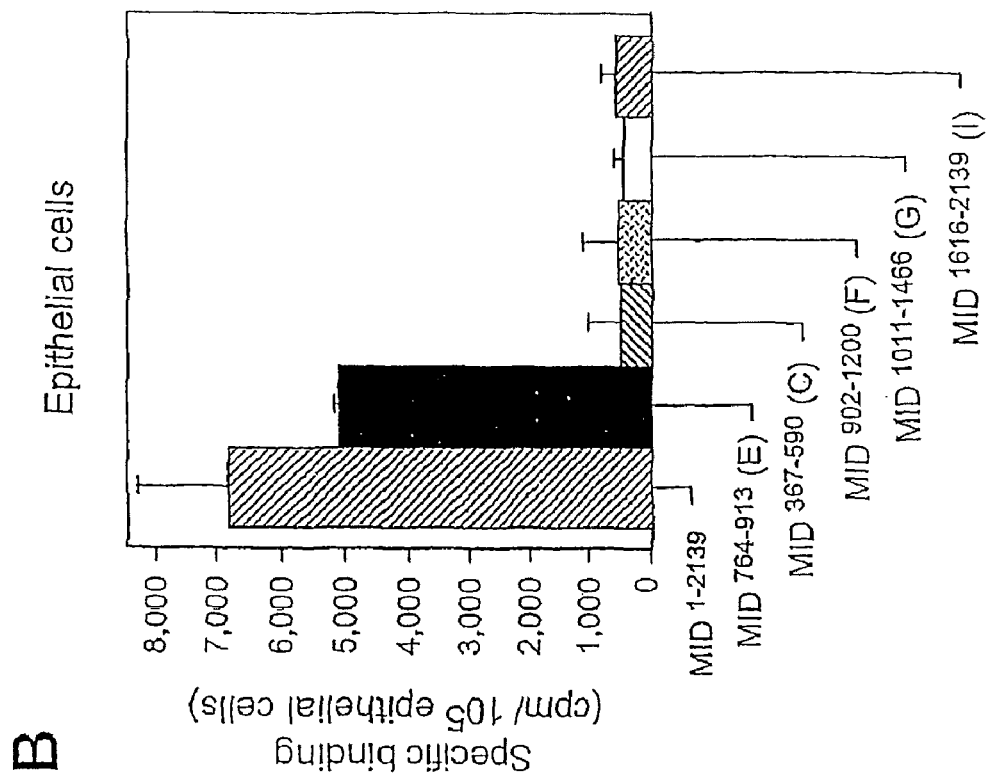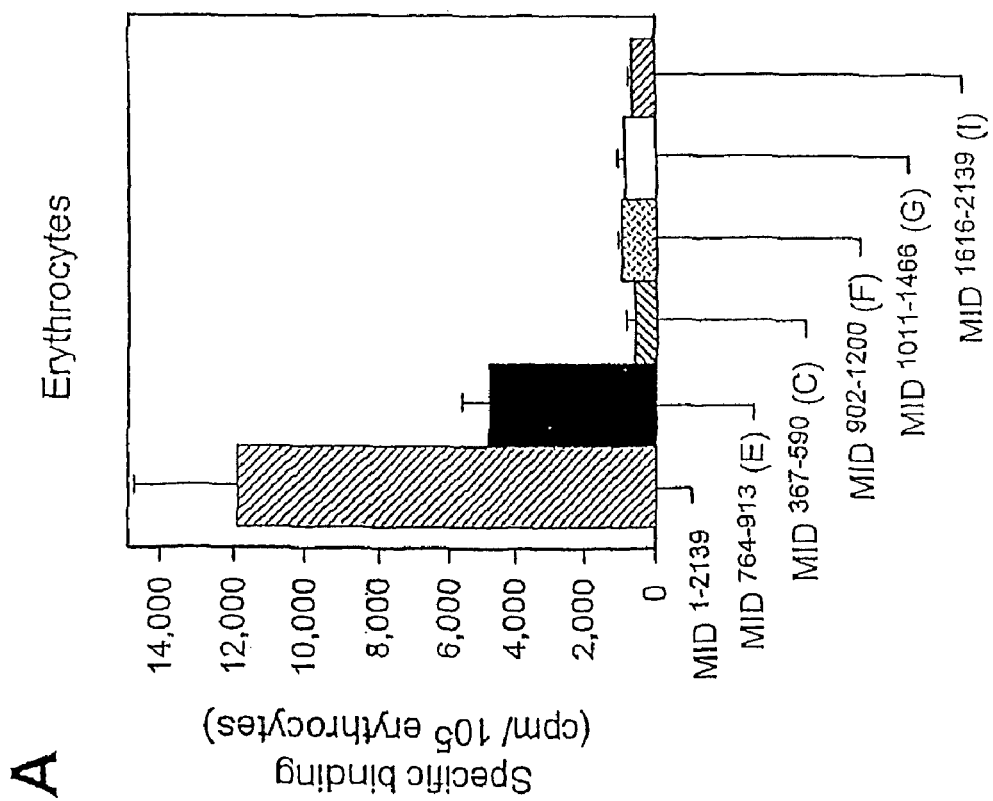
Fig 13

SURFACE EXPOSED IMMUNOGLOBULIN D-BINDING PROTEIN FROM *MORAXELLA CATARRHALIS*

This application is a continuation application of U.S. patent application Ser. No. 10/480,456, filed on Jul. 13, 2004, now U.S. Pat. No. 7,470,432, issued on Dec. 30, 2008, which is a national stage filing under 35 U.S.C. §371 of International Patent Application No. PCT/SE02/01299, filed on Jul. 1, 2002, which claims the benefit of Swedish Patent Application No. 0102410-8, filed on Jul. 4, 2001, the entire contents of which are hereby incorporated by reference for all purposes.

FIELD OF THE INVENTION

The present invention relates to a surface exposed protein, which can be detected in *Moraxella catarrhalis*, having an amino acid sequence as described in SEQ ID NO: 1, an apparent molecular weight of 200 kDa and a capacity of selectively binding membrane bound or soluble IgD, and to an immunogenic or IgD-binding fragment of said surface exposed protein, and to an immunogenic and adhesive fragment of said surface exposed protein.

BACKGROUND OF THE INVENTION

*Moraxella catarrhalis* is a Gram-negative diplococcus that for a long time was considered a relatively harmless commensal in the respiratory tract. At present, it is the third most frequent cause of otitis media and also a significant agent in sinusitis and lower respiratory tract infections in adults with pulmonary disease. *M. catarrhalis* is also one of the most common inhabitants of the pharynx of healthy children.

Two decades ago, *Haemophilus influenzae* and *M. catarrhalis* were shown to display a strong affinity for both soluble and surface-bound human IgD (1). The IgD-binding seems to be paralleled by a similar interaction with surface-bound IgD at the cellular level, a phenomenon that explains the strong mitogenic effects on human lymphocytes by *H. influenzae* and *M. catarrhalis* (2-4). An IgD-binding outer membrane protein from *H. influenzae* (protein D) was isolated and cloned, and shown to be an important pathogenicity factor (5). However, protein D does not bind to the majority of IgD myelomas tested, and it was suggested that encapsulated *H. influenzae* of serotype b expresses an additional IgD receptor (6).

Early studies demonstrated that the outer membrane proteins (OMPs) from a diverse collection of *Moraxella* isolates exhibit a high degree of similarity (7). Investigators have primarily focused their research efforts on a selected group of proteins. Recent studies have demonstrated that the high-molecular-weight surface antigen, termed UspA or HMW-OMP, is actually comprised of two different proteins. These proteins are named UspA1 and UspA2 (8,9,10). The apparent molecular masses of these OMPs are greater than 250 kDa as determined by SDS-PAGE analysis. Reduction with formic acid yields bands of approximately 120 to 140 kDa, suggesting that the UspA proteins form an oligomeric complex composed of several monomeric subunits (11). The predicted mass of each protein, as deduced from the cloned genes, is 88 kDa and 62 kDa for UspA1 and UspA2, respectively. It is thought that the difference in the deduced mass and the mass determined using SDS-PAGE is due to a predicted coiled coil structure (9).

In a recent patent publication, an outer membrane protein of *M. catarrhalis* with a molecular mass of approximately 200 kDa was isolated (12). A sequence encoding a protein of approximately 200 kDa was also provided. The protein was shown to be immunogenic, but no further biological functions were presented. In addition, a 200 kDa protein is associated with hemagglutinating *M. catarrhalis* (13,14).

CopB is an 80 kDa surface exposed major OMP that shows a moderate antigenic conservation. In addition, OMP CD is a 46 kDa highly conserved protein with numerous surface exposed epitopes and OMP E a 47 kDa protein detected on a variety of heterologous strains. The lactoferrin-binding (LbpA and B) and transferrin-binding (TbpA and B) proteins have molecular sizes of 99-111 and 74-105 kDa, respectively.

Certain strains of *Staphylococcus aureus* produce immunostimulatory exotoxins such as toxic shock syndrome toxin-1 (TSST-1), staphylococcal enterotoxin A (SEA), SEB and SEC, all of which are associated with food poisoning and toxic shock syndrome (TSS). These exotoxins have been denominated as superantigens (SAg) due to their ability to activate a high frequency of T lymphocytes. SAg bind as unprocessed proteins to HLA class II molecules on APC and oligoclonally activate T cells expressing particular TCR Vβ chains. In vivo exposure to excessive amounts of SAg results in a strong cytokine production and includes IL-2, TNF-α and IFN-γ, which are associated with a toxic shock like syndrome.

Since the discovery of the first immunoglobulin-binding bacterial protein, *S. aureus* protein A (SpA) in 1966, this protein has been extensively characterized. The ability of SpA to bind the Fc part of IgG is well known, but SpA also binds a fraction of 1 g-molecules of all classes due to the so called 'alternative' binding, which represents an interaction with the variable region of certain heavy chains. All IgG-binding capacity of *S. aureus* has been considered to be mediated by SpA. However, the existence of a second gene in *S. aureus* encoding an Ig-binding protein has also been reported. *Streptococcus pyogenes* and *Peptostreptococcus magnus* are other examples of Ig-binding bacteria. *S. pyogenes* produces protein H belonging to the M family of proteins, and has strong affinity for the Fc region of IgG. Proteins expressed by some strains bind IgA instead of IgG or both IgG and IgA. Protein Bac or the B-antigen is an IgA-binding protein expressed by certain strains of group B streptococci. Finally, *P. magnus* expresses protein L that shows high and specific affinity for Ig light chains, especially k light chains, and thereby interacts with all classes of Ig.

IgD is a unique immunoglobulin that exists in both a soluble and a surface-bound form. Both forms are encoded by the same gene and are splicing products. All mature B lymphocytes have B cell receptors (BCR) consisting of membrane-bound IgD and IgM. Soluble IgD comprises approximately 0.25% of the total amount of serum-Ig. The main function of IgD seems to be as an antigen-receptor on the B cell surface in order to optimize B cell recruitment and accelerated affinity maturation. Antigen is taken up through IgD by endocytosis followed by intracellular degradation and presentation on MHC class II for T cells, which in turn are activated and produce cytokines. Hereby, T cell help is obtained including numerous cytokines (e.g. interleukin-4) and co-stimulatory molecules such as CD28.

Despite macrophages, dendritic cells, and B cells all can present antigens to T lymphocytes, the B cells are 100-fold more efficient due to the importance of the antigen-presenting immunoglobulin on the surface. An attractive strategy in order to potentiate immunization is to directly target an antigen to the B cell receptor. It was early shown that the mouse antibody-response against bovine serum albumin (BSA) conjugated to anti-IgD monoclonal antibodies was 100-fold stronger compared to BSA administration without any antibody. In parallel, it has been demonstrated that a mouse myeloma antigen incorporated into the constant region of anti-IgD-antibodies targeted to the surface-bound IgD results in an up to 1000-fold more efficient antigen presentation on MHC class II (15).

Tolerance induction can be achieved experimentally by B cell activation through the IgD BCR without any additional T cell help. It would also be possible to treat autoimmune diseases by inducing B cell anergy and thus inhibit the production of auto-antibodies. In fact, SLE-prone mice administered dextran-conjugated anti-IgD antibodies exhibit a delayed development of autoimmunity. In yet another study it was shown that B cell activation via IgD decreases a T helper 2-induced IgE response suggesting a therapy for diminishing the IgE production in severely allergic individuals by displacing the antibody response from a Th2- to a Th1-response. By targeting antigens to the B cell receptor IgD, stimulation, tolerance, and a switch from IgE-production can be achieved. In addition, polyclonal activation has been reported. The outcome is depending on the experimental model used. With different constructs including various repeating IgD-binding segments, it is possible to tailor the response.

The T cell is a significant player in the anti-tumor response since it recognizes tumor-specific antigens. However, the important T cells display commonly depressed activity in the cancer patient due to a general immunosuppression. A triggering of T helper cells would therefore be very beneficial. Vaccination against tumors using antigen presenting cells (APC) has recently been acknowledged (17). Immunization protocols with APC pulsed ex vivo with tumor antigens (peptides) have been shown to induce effective MHC class I presentation for cytotoxic T cells. It has also been demonstrated that EBV-transformed B cells are able to present melanoma antigens for tumor-infiltrating lymphocytes (TIL). In experimental models, it has also been shown that tumor cells transfected with MHC class II and B7 surface molecules, receptors that are abundant on B cells, would be a feasible approach for tumor vaccination. Interestingly, B16 melanoma bearing mice that were injected with B cells pulsed with a tumor lysate from the corresponding cell line showed a prolonged survival due to an increase in IFN-γ producing T cells. It was also demonstrated that the induced T helper cells evoked a stronger cytotoxic response against the solid tumors. Since myeloma antigen targeted to IgD induces a T cell response, the suggested approach using IgD-binding bacterial proteins conjugated to specific tumor antigens would be feasible.

To target an antigen (e.g. peptide derived from a microbe or a specific tumor) to IgD-bearing B cells in order to trigger both humoral and cellular immune responses a IgD-binding protein or a shorter IgD-binding peptide would be a very feasible vector. Several examples of successful strategies with a similar angle of approach exist. The humoral immune response in mice against bovine serum albumin (BSA) conjugated to anti-IgD monoclonal antibodies is 100-fold stronger compared to when BSA is administered alone. A recent publication by Lunde et al. (15) describes that when a myeloma-derived peptide is integrated in the constant region of anti-IgD Fab' fragments and injected into mice, a 1,000-fold more efficient antigen presentation is achieved against the antigen in question (15). In parallel, the Ig-binding fragment of *S. aureus* protein A fused with cholera toxin significantly increases both systemic and mucosal immune responses 10- to 100-fold against the cholera toxin (16). Finally, in a mouse tumor model consisting of the experimentally well defined B16 melanoma, activated B lymphocytes that are pulsed ex vivo with peptides derived from the tumor tissue can evoke a stronger anti-tumor response in vivo and consequently a prolonged survival (17).

SUMMARY OF THE INVENTION

In one aspect the present invention relates to a surface exposed protein, which can be detected in *Moraxella catarrhalis*, having an amino acid sequence as described in SEQ ID NO: 1, an apparent molecular weight of 200 kDa and a capacity of selectively binding membrane bound or soluble IgD, or naturally occurring or artificially modified variants thereof, or an immunogenic or IgD-binding fragment of said protein or variants, or an immunogenic and adhesive fragment of said surface exposed protein.

In another aspect the present invention relates to an immunogenic or IgD-binding fragment of a surface exposed protein as defined above, which fragment can be detected in *Moraxella catarrhalis*, having a capacity of selectively binding membrane bound or soluble IgD, or naturally occurring or artificially modified variants thereof.

In a further aspect the present invention relates to an immunogenic or IgD-binding fragment as described above, having an amino acid sequence as described in SEQ ID NO:10.

In still a further aspect the present invention relates to an immunogenic and adhesive fragment of a surface exposed protein as defined above, which fragment can be detected in *Moraxella catarrhalis*, having a capacity of binding erythrocytes and epithelial cells.

In still another aspect the present invention relates to an immunogenic and adhesive fragment as defined above, having an amino acid sequence as described in SEQ ID NO: 8.

In one aspect the present invention relates to a DNA segment comprising a DNA sequence, as shown in SEQ ID NO: 2, which DNA sequence codes for a surface exposed protein of *Moraxella catarrhalis* as defined above, or naturally occurring or artificially modified variants of said DNA sequence.

In yet another aspect the present invention relates to a DNA segment comprising a DNA sequence which codes for an immunogenic or IgD-binding fragment as defined above.

In a further aspect the present invention relates to a DNA segment as defined above, comprising a DNA sequence, as shown in SEQ ID NO: 11, which DNA sequence codes for an immunogenic or IgD-binding fragment as defined above.

In still a further aspect the present invention relates to a DNA segment comprising a DNA sequence, which codes for an immunogenic and adhesive fragment of a surface exposed protein as defined above.

In another aspect the present invention relates to a DNA segment as above, comprising a DNA sequence, as shown in SEQ ID NO: 9, which DNA sequence codes for an immunogenic and adhesive fragment as defined above.

In a further aspect the present invention relates to a vaccine containing a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants of said protein, or an immunogenic or IgD-binding fragment of said protein or variants, or an immunogenic and adhesive fragment of said surface exposed protein.

In another aspect the present invention relates to a vaccine containing an immunogenic or IgD-binding fragment of a surface exposed protein of *Moraxella catarrhalis*, which has a capacity of selectively binding membrane bound or soluble IgD, or naturally occurring or artificially modified variants of said fragment, preferably a vaccine containing an immunogenic or IgD-binding fragment having an amino acid sequence as described in SEQ ID NO: 10.

In still another aspect the present invention relates to a vaccine containing an immunogenic and adhesive fragment of a surface exposed protein of *Moraxella catarrhalis* as defined above, preferably a vaccine containing an immunogenic and adhesive fragment having an amino acid sequence as described in SEQ ID NO: 8.

In one preferred embodiment said vaccines are combined with another vaccine and in another preferred embodiment said vaccines are combined with an immunogenic portion of another molecule.

In one aspect the present invention relates to a plasmid or phage comprising a DNA sequence, which codes for a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants thereof, or an immunogenic or IgD-binding fragment of said protein or variants.

In another aspect the present invention relates to a plasmid or phage comprising a DNA sequence, which codes for a an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, preferably a plasmid or phage comprising a DNA sequence, which codes for a an immunogenic or IgD-binding fragment having an amino acid sequence as described in SEQ ID NO: 10.

In still another aspect the present invention relates to a plasmid or phage comprising a DNA sequence, which codes for an immunogenic and adhesive fragment of a surface exposed protein as defined above, which fragment can be detected in *Moraxella catarrhalis* and has a capacity of selectively binding erythrocytes and epithelial cells or naturally occurring or artificially modified variants of said fragment, preferably a plasmid or phage comprising a DNA sequence, which codes for a an immunogenic and adhesive fragment having an amino acid sequence as described in SEQ ID NO: 8.

In yet another aspect the present invention relates to a non human host comprising at least one plasmid or phage as defined above, and capable of producing said protein or variants, or said immunogenic or IgD-binding fragment of said protein or variants, or said immunogenic and adhesive fragment of said protein, which host is chosen among bacteria, yeast and plants. In one embodiment the host is *E. coli*.

In one aspect the present invention relates to a recombinant DNA molecule comprising a DNA sequence coding for a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants thereof, or for an immunogenic or IgD-binding fragment of said protein, or variants, which DNA sequence is combined with another gene.

In another aspect the present invention relates to a recombinant DNA molecule comprising a DNA sequence coding for an immunogenic or IgD-binding fragment of a surface exposed protein, which fragment can be detected in *Moraxella catarrhalis* and has a capacity of selectively binding membrane bound or soluble IgD, or naturally occurring or artificially modified variants thereof, which DNA sequence is combined with another gene, preferably a recombinant DNA molecule comprising a DNA sequence coding for an immunogenic or IgD-binding fragment having an amino acid sequence as described in SEQ ID NO: 10.

In still another aspect the present invention relates to a recombinant DNA molecule comprising a DNA sequence coding for an immunogenic and adhesive fragment of a surface exposed protein as above, which fragment can be detected in *Moraxella catarrhalis* and has a capacity of selectively binding erythrocytes and epithelial cells, or naturally occurring or artificially modified variants of said fragment, which DNA sequence is combined with another gene, preferably a recombinant DNA molecule comprising a DNA sequence coding for an immunogenic and adhesive fragment having an amino acid sequence as described in SEQ ID NO: 8.

In yet another aspect the present invention relates to a plasmid or phage comprising said fused DNA sequence as defined above.

In a further aspect the present invention relates to a non-human host comprising at least one plasmid or phage as defined above, which host is chosen among bacteria, yeast and plants. In one embodiment the host is *E. coli*.

In one aspect the present invention relates to a fusion protein or polypeptide, in which a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants thereof, or an immunogenic or IgD-binding fragment of said protein or variants, is combined with another protein by the use of a recombinant DNA molecule as defined above.

In another aspect the present invention relates to a fusion protein or polypeptide, in which an immunogenic or IgD-binding fragment of a surface exposed protein, which fragment can be detected in *Moraxella catarrhalis*, which has a capacity of selectively binding membrane bound or soluble IgD, or naturally occurring or artificially modified variants thereof, is combined with another protein by the use of a recombinant DNA molecule as defined above.

In still another aspect the present invention relates to a fusion protein or polypeptide in which an immunogenic and adhesive fragment of a surface exposed protein as defined above, which fragment can be detected in *Moraxella catarrhalis* and has a capacity of selectively binding erythrocytes and epithelial cells, or naturally occurring or artificially modified variants of said fragment, is combined with another protein by the use of a recombinant DNA molecule as defined in above.

In yet another aspect the present invention relates to a fusion product, in which a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants of said protein, or an immunogenic or IgD-binding fragment of said protein or variants, is covalently or by any other means bound to a protein, carbohydrate or matrix.

In a further aspect the present invention relates to a fusion product in which an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, is covalently or by any other means bound to a protein, carbohydrate or matrix.

In still another aspect the present invention relates to a fusion product in which an immunogenic and adhesive fragment of a surface exposed protein as defined above, which fragment can be detected in *Moraxella catarrhalis* and has a capacity of selectively binding erythrocytes and epithelial cells, or naturally occurring or artificially modified variants of said fragment, is covalently, or by any other means, bound to a protein, carbohydrate or matrix. Preferably, a fusion product in which an immunogenic or IgD-binding fragment, having an amino acid sequence described in SEQ ID NO: 10, is covalently, or by any other means, bound to a protein, carbohydrate or matrix. Preferably, a fusion product in which an immunogenic and adhesive fragment, having an amino acid sequence described in SEQ ID NO: 8, is covalently, or by any other means, bound to a protein, carbohydrate or matrix.

In one aspect the present invention relates to a method of detecting IgD using a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants of said protein, or an immunogenic or IgD-binding fragment of said protein or variants, optionally labeled and/or bound to a matrix.

In a further aspect the present invention relates to a method of detecting IgD using an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, optionally labeled and/or bound to a matrix.

In another aspect the present invention relates to a method of detecting IgD using an immunogenic or IgD-binding fragment of a surface exposed protein of *Moraxella catarrhalis*, having an amino acid sequence as described in SEQ ID NO: 10, and a capacity of selectively binding membrane bound or soluble IgD, or naturally occurring or artificially modified variants of said fragment, optionally labeled and/or bound to a matrix.

In a further aspect the present invention relates to a method of separating IgD using a surface exposed protein of *Moraxella catarrhalis*, said protein an amino acid sequence as shown in SEQ ID NO: 1, an apparent molecular weight of 200 kDa and a capacity of selectively binding membrane bound or soluble IgD, or naturally occurring or artificially modified variants of said protein, or an immunogenic or IgD-binding fragment of said protein or variants, optionally bound to a matrix.

In yet another aspect the present invention relates to method of separating IgD using an immunogenic or IgD-binding fragment of a surface exposed protein, which fragment can be detected in *Moraxella catarrhalis* and has a capacity of selectively binding membrane bound or soluble IgD, or naturally occurring or artificially modified variants of said fragment, optionally bound to a matrix.

In another aspect the present invention relates to a method of separating IgD using an immunogenic or IgD-binding fragment of a surface exposed protein of *Moraxella catarrhalis*, having an amino acid sequence as described in SEQ ID NO: 10, and a capacity of selectively binding membrane bound or soluble IgD, or naturally occurring or artificially modified variants of said fragment, optionally labeled and/or bound to a matrix.

In one aspect the present invention relates to a method of isolation of a surface exposed protein of *Moraxella catarrhalis*, said protein having an amino acid sequence as shown in SEQ ID NO: 1, an apparent molecular weight of 200 kDa and a capacity of selectively binding membrane bound or soluble IgD, or naturally occurring or artificially modified variants of said protein, or an immunogenic or IgD-binding fragment of said protein or variants. Said method comprises the steps:

a) subjecting a suspension of *Moraxella catarrhalis* to an extraction process by adding a zwitterionic or non-ionic detergent, optionally in the presence of EDTA;

b) applying the extract comprising the IgD-binding protein of *Moraxella catarrhalis* from step a) to an adsorption column;

c) eluting the IgD-binding protein; and d) separating the IgD-binding protein.

In another embodiment the concentration of the detergent in step a) of the method is within the range 0.1-5%, preferably 3%.

In yet another aspect the present invention relates to a method for treatment of an autoimmune disease comprising extra corporal circulation of the blood trough a material comprising a surface exposed protein as defined above, or a fragment thereof as defined above, for removal of IgD from the blood.

In one aspect the present invention relates to a purified antibody which is specific to an immunogenic portion of a surface exposed protein *Moraxella catarrhalis*, said protein having an amino acid sequence as described in SEQ ID NO: 1, an apparent molecular weight of 200 kDa and a capacity of selectively binding membrane bound or soluble IgD, or naturally occurring or artificially modified variants thereof, or an immunogenic or IgD-binding fragment of said protein or variants.

In another aspect the present-invention relates to a purified antibody as described above, which is specific to an immunogenic or IgD-binding fragment as defined above, having a capacity of selectively binding membrane bound or soluble IgD, or naturally occurring or artificially modified variants of said fragment.

In still another aspect the present invention relates to a purified antibody as described above, which is specific to an immunogenic or adhesive fragment as defined above, having a capacity of binding erythrocytes and epithelial cells.

DESCRIPTION OF THE FIGURES

FIG. 6. Nucleotide sequence (nucleotides 106-6889 of SEQ ID NO: 2) of the mid gene from *M. catarrhalis* Bc5 together with the deduced amino acid sequence (SEQ ID NO: 1). Putative −35, −10 regions, a possible ribosome binding site (RBS), inverted repeat, the predicted signal peptide, and two alternative start-codons at amino acid positions 1 and 17 are indicated. The stop-codon and the inverted repeat is also shown.

FIG. 7. The degrees of identity and similarity between MID isolated from five *M. catarrahlis* strains and UspA1 and A2 from ATCC 25238 are demonstrated. The identity and similarity were calculated using the software Needle.

FIG. 13. [125I]-labeled recombinant MID764-913 (fragment E) is specifically attracted to erythrocytes and epithelial cells. [125I]-labeled MID and a series of truncated [125I]-MID fragments (C, E, F, G, and I) were added to human erythrocytes (A). The recombinant [125I]-labeled MID fragments were also added to epithelial cells (B). All truncated MID proteins (except fragment I) were produced in *E. coli* followed by purification on nickel resins. Fragment I was a fusion protein with MBP and consequently purified on an amylose resin. The recombinant proteins were labeled with [125I] and added to erythrocytes or the epithelial cell line A549. After several washings, bound radioactivity was measured in a γ-counter. Data are presented as mean values of 2 experiments with duplicates. Error bars indicate SD.

DESCRIPTION OF THE INVENTION

Figure 1:
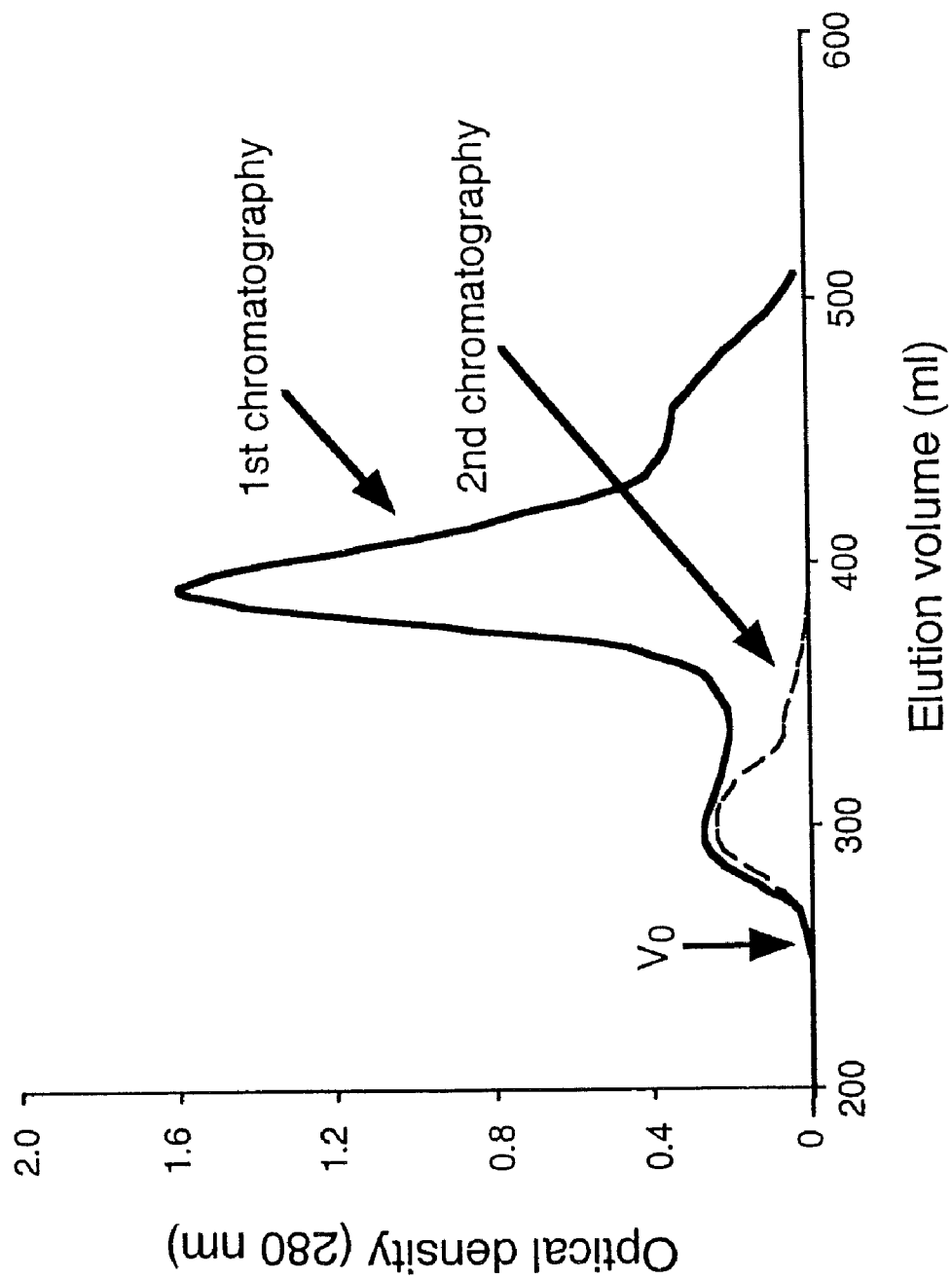
FIG. 1. Chromatography and rechromatography on a SEPHACRYLT™ S-400 column of EMPIGEN® soluble extract from *M. catarrhalis* after ion exchange chromatograpy. The solid line indicates protein content of the first chromatography and the broken line rechromatography of the first peak. Vo specifies the void volume.

MID is not identical to previously well characterized outer membrane proteins of *M. catarrhalis*. It is not recognized by monoclonal antibodies derived against the UspA or CopB outer membrane antigens. MID also has a different migration pattern in SDS-PAGE and a different composition as shown by amino acid and DNA sequence analysis. MID appears as a 200 kDa band in accordance with the Mw from the deduced amino acid sequence, but also as an extra band with an estimated molecular mass of more than 1,000 kDa. The extra band indicates that native MID is an oligomeric complex in a similar fashion as UspA (11). This is further supported by the fact that MID was eluted immediately after the void volume from a SEPHACRYL™. S-400 column with a fractionation range of up to ~8,000 kDa. The amino acid sequences for MID shows 11.1 and 6.7% identity, respectively, with the USPA1 and USPA2 outer membrane proteins from *M. catarrhalis* (FIG. 7).

In a recent patent publication, an outer membrane protein of *M. catarrhalis* with a molecular mass of approximately 200 kDa was isolated (12). A sequence encoding a protein of approximately 200 kDa was also provided. However, that protein sequence is not identical to the sequence provided by us and shows only 45.9 to 54.4% identity with MID (FIG. 7). The protein was shown to be immunogenic, but no further biological functions were presented. In addition, a 200 kDa protein is associated with hemagglutinating *M. catarrhalis* (13,14).

Experimental Part

The present investigation describes the isolation, purification, characterization, cloning and expression of the novel Ig-binding protein named MID of *M. catarrhalis*, which has affinity for human IgD, of an immunogenic or IgD-binding fragment of said surface exposed protein, and of an immunogenic and adhesive fragment of said surface exposed protein.

Materials and Methods
Bacteria and Plasmids

*M. catarrhalis*, strain Bc5, was a clinical isolate from a nasopharyngeal swab culture at our Department. 118 strains isolated from blood, nasopharynx, and sputum were obtained from Sweden, Denmark, Finland, Hungary, Japan, and USA. Sequenced strains and plasmids used for expression are shown in Table I.

TABLE I

Bacterial strains and plasmids used in this study

| Strains or Plasmid | Description (site of isolation) | Reference or source |
|---|---|---|
| Strains | | |
| DH5α | *E. coli* | Novagen |
| BL21DE3 | *E. coli* | Novagen |
| BBH17 | *M. cararrhalis* (sputum) | Christensen (Denmark) |
| Bc5 | *M. cararrhalis* (nasopharynx) | Dept. Clinical Microbiology, (Malmo, Sweden) |
| NCTC 4103 | *M. cararrhalis* (nasopharynx) | CCUG (Gothenburg, Sweden) |
| RH1 | *M. cararrhalis* (blood) | Christensen (Denmark) |
| RH4 | *M. cararrhalis* (blood) | Christensen (Denmark) |
| Plasmid | | |
| pET16(b) | Expression vector | Novagen |
| pET16-MID | PET16(b) with the ORF of mid | This study |

Bacteria were grown overnight in Nutrient Broth (Oxoid, Basingstoke Hampshire, England), harvested and washed in phosphate-balanced saline (PBS), pH 7.2 by centrifugation.

Immunoglobulins, Sera and Other Proteins

The Ig preparations IgG1 (κ), IgG1(λ), IgG2(κ), IgG2(λ), IgG3(κ), IgG3(λ), IgG4(κ), IgG4(λ), IgA1(κ) IgA1(λ), IgA2 (κ), IgA2(λ), IgM (κ), IgM(λ), IgD(κ), IgD(λ) and IgE(κ) were all of human origin and purchased from The Binding Site (Birmingham, England). IgD myeloma sera IgD(κ) and IgD(λ) were from the same company and IgD-standard serum OTRD 02/b3 was from Behringwerke A G (Marburg, Germany). Myeloma sera IgD(λ)A, IgD(λ) B, IgG A, IgG B, IgG C, IgM, IgA A and IgA B were obtained from the Department of Clinical Chemistry, Malmo, Sweden. The concentration of respective immunoglobulins was according to the suppliers.

Antibodies

Horseradish peroxidase (HRP)-conjugated goat anti-human IgD was from Biosource (Camarillo, Calif.). Fluoresceinisothiocyanate (FITC)-conjugated mouse anti-human IgD, unlabeled rabbit anti-human IgD, and HRP-labeled rabbit anti-mouse Ig were purchased from Dakopatts (Gentofte, Denmark). Goat anti-human IgD and HRP-conjugated rabbit anti-human polyvalent immunoglobulins was from Sigma (St. Louis, Mo.). Phycoerythrin (RPE)-conjugated mouse anti-human CD3 and CD19 were from Becton Dickinson (San Jos, Calif.). Mouse monoclonal antibodies 17C7 (UspA) and 10F3 (CopB) were kindly provided by Dr. Eric J. Hansen, Department of Microbiology, University of Texas (Dallas, Tex.).

Antisera

Rabbits were immunized intramuscularly with 200 μg of purified MID (Forsgren et al., 2001), recombinant MID fragments, or recombinant UspA1 emulsified in complete Freunds adjuvans (Difco, Becton Dickinson, Heidelberg, Germany) and boosted on days 18 and 36 with the same dose of protein in incomplete Freunds adjuvans. Blood was drawn 2 to 3 weeks later. The anti-UspA1 polyclonal antibodies reacted with both recombinant UspA1 and UspA2 as examined by Western blots.

SDS-PAGE and Detection of Proteins on Membranes (Western Blot)

SDS-PAGE was run using a commercial electrophoresis system consisting of 10% Bis-Tris gels with running (MES), sample (LDS), and transfer buffer as well as a blotting instrument (Novex, San Diego, Calif.). Briefly, samples were boiled for 10 min followed by electrophoresis at room temperature using Protein II vertical slab electrophoresis cells (Novex) at 150 constant voltage. Gels were stained with Coomassie Brilliant Blue R-250 (Bio-Rad, Sundbyberg, Sweden). In addition, electrophoretical transfer of protein bands from the gel to an immobilon-P membrane (Millipore, Bedford, Mass.) was carried out at 30 V for 2-3 h. After transfer, the immobilon-P membrane was blocked in PBS with 0.05% Tween 20 (PBS-Tween) containing 5% milk powder. After several washings in PBS-Tween, the membrane was incubated for 1 h in room temperature with purified IgD myeloma protein (0.5 μg/ml, hu IgD(κ) myeloma; The Bindingsite, Birmingham, UK) in PBS-Tween including 2% milk powder. HRP-conjugated goat anti-human IgD diluted {fraction (1/1000)} in the same buffer was added after several washings in PBS-Tween. In some experiments, IgD myeloma protein was replaced by myeloma protein of other immunoglobulin classes and HRP-labeled anti-human polyvalent immunoglobulins (Sigma) was used as secondary layer. Mouse mAbs 17C7 and 10F3 were used to detect *Moraxella* outer membrane proteins UspA1, 2 and Cop B, respectively (7,8). In these experiments, HRP-labeled rabbit anti-mouse immunoglobulins were used as a secondary layer. After incubation for 40 min at room temperature and several additional washings in PBS-Tween, development was performed with ECL Western blotting detection reagents (Amersham Pharmacia Biotech, Uppsala, Sweden). Western blots were analyzed by a Personal Molecular Imager FX (Bio-Rad).

Enzyme Linked Immunosorbent Assay (ELISA)

ELISA was used to quantitate the immunoglobulin D-binding protein. Extracts of *M. catarrhalis* diluted in five-fold steps in 0.1 M Tris-HCl, pH 9.0 were added in 100 µl volumes to microtiter plates (F96 Maxisorb, Nunc-Immuno module, Roskilde, Denmark), which were sealed and incubated at 4° C. overnight. After washing the plate four times in PBS-Tween, blocking buffer PBS-Tween containing 1.5% ovalbumin, was added. The plate was incubated for 1 h at room temperature and further washed four times with PBS-Tween. IgD(κ) myeloma protein, 0.05 µg in 100 µl PBS-Tween containing 1.5% ovalbumin was added to each well and after incubation for 1 h at room temperature the plate was washed four times with PBS-Tween. After 1 h incubation with HRP-conjugated goat anti-human IgD diluted {fraction (1/1000)} in the same buffer and subsequent washing with PBS-Tween, tetramethylbenzidine (20 mM) in 0.1 M potassium citrate solution, pH 4.25, mixed with hydrogen peroxide (final concentration 0.002%) was added. After 30 min, the enzymatic reaction was stopped by adding 2 M sulphuric acid. The optical density (OD) was then measured at 450 nm in an automated ELISA reader (Multiskan Plus, Labsystems, Finland)

Dot Blot Assay

Purified MID (0.0005-0.2 µg) in a volume of 100 µl in 0.1 M Tris-HCl, pH 9.0 were manually applied to nitrocellulose membranes (Schleicher & Schuell, Dessel, Germany) by using a dot blot apparatus (Schleicher & Schuell). After saturation, the membranes were incubated for 2 h at room temperature in PBS-Tween containing 1% ovalbumin and 5% milk powder and washed four times with PBS-Tween. Human myeloma protein 0.5 µg in 100 µl PBS-Tween was added and after 2 h of incubation, followed by several washings in PBS-Tween, HRP-labeled anti-human light chains (κ and λ) (Dakopatts) in dilution {fraction (1/200)} was used as a secondary antibody. Development was performed as described above for the Western blots. In another set of experiments, dilutions of human myeloma sera in a volume of 100 µl in 0.1 M Tris-HCl, pH 9.0 was first applied to the membranes. After saturation, incubations, blocking, and washing steps were performed as described above. Thereafter, [125I]-labeled protein MID probe (5 to 10×10$^5$ cpm/ml) in PBS-Tween was added. After overnight incubation, the membrane was washed four times with PBS-Tween, air dried, and exposed to Kodak CEA.C x-ray films at −70° C. using Kodak X-Omat regular intensifying screen (Eastman Kodak, Rochester, N.Y.).

Extraction of IgD-Binding Protein

*M. catarrhalis* bacteria (1-5×1011 colony forming units (cfu)/ml) were suspended in 0.05 M Tris-HCl-buffer (pH 8.8) containing 0.1-5% EMPIGEN® (Calbiochem Novabiochem, Bedford, Mass.). In some experiments EMPIGEN® was replaced by CHAPS (Sigma), n-Octyl-p-D-glucoside (Bachem, Budendorf, Switzerland) or Triton X-100 (Sigma). All these detergents at a concentration of 0.1-5% were tested with or without 0.01 M EDTA. The bacterial suspensions were mixed by magnetic stirring for 2 h at 37° C. After centrifugation at 8000×g for 20 min at 4° C., the supernatants were filtrated with sterile filters (0.45 µm; Sterivex-HV, Millipore).

Purification of IgD-Binding Protein

*M. catarrhalis* extract in 3% EMPIGEN® was applied to a Q-SEPHAROSE® column (Amersham Pharmacia Biotech) equilibrated with 0.05 M Tris-HCl (pH 8.8) containing 0.1% EMPIGEN®. The column was eluted using a 0 to 1 M NaCl linear gradient in the same buffer. Fractions showing most IgD-binding activity as detected by ELISA and Western Blot were pooled, dialyzed in Spectraphor membrane tubes (molecular weight cut off 25,000; Spectrum, Laguna hills, CA) against 0.05 M Tris-HCl, pH 8.8, concentrated on YM100 disc membranes (molecular weight cut off 100,000; Amicon, Beverly, Mass.) and then applied to gel-chromatography. The gel-filtration of IgD-binding protein was done on a SEPHACRYL™ S-400 high resolution column (20 by 900 mm; Amersham Pharmacia Biotech), equilibrated with 0.05 M Tris-HCl, pH 8.8 containing 0.1% EMPIGEN®. Fractions containing the strongest IgD-binding activity were concentrated and re-chromatographed as described above.

Peptide Cleavage and Amino Acid Sequence Analysis

Purified MID in 0.05 M Tris-HCl (pH 8.8) containing 0.1% EMPIGEN® was treated with trypsin or chymotrypsin in an enzyme-protein-ratio of 1:10 at 37° C. overnight. The cleavage mixtures were subjected to SDS-PAGE and peptide bands transferred to Immobilon membranes were automatically sequenced or exposed to Western blot analysis as described above. In order to get an N-terminal sequence of the protein, deblocking of intact MID from a possible pyroglutamate group was attempted. Two different protocols were used to deblock both soluble and membrane-bound protein. Automated amino acid sequence analysis was performed with an Applied Biosystems (Foster City, Calif.) 470A gas-liquid solid phase sequenator with on-line detection of the released aminoacid phenylthiohydantoin derivatives by Applied Biosystems model 120A PTH analyzer.

Labeling of Protein MID

Purified MID was radioiodinated ([125I]; Amersham, Buckinghamshire, England) to high specific activity with lactoperoxidase. The preparations contained approximately 0.05 mol iodine per mol protein. FITC (Sigma) was conjugated to purified MID using a standard protocol. Briefly, MID (2 mg/ml) in 0.1 M carbonate buffer, pH 9.5, was incubated with 0.15 µg/ml FITC solubilized in DMSO. After 45 min at room temperature and constant stirring, the sample was diluted and subjected to a PD10 column (Pharmacia Biotech) pre-equilibrated with PBS, pH 7.4. The resulting MID-FITC was used for binding studies.

DNA Isolation and Sequencing

Genomic DNA was extracted from five *M. catarrhalis* strains (see Table I) using a genomic DNA preparation kit (Qiagen, Hilden, Germany) and was subsequently used as template for amplification of the MID gene by PCR. Degenerate primers were synthesized according to the amino terminal sequences of the four peptide fragments (Table II).

TABLE II

Amino acid sequences derived from highly purified MID after protease digestions
(SEQ ID NOS: 12-15, respectively in order of appearance).

| Peptide sequence | Protease |
| --- | --- |
| TAQANTESSIAVG | Trypsin |
| GNTATNFSVNSGDDNALIN | Trypsin |
| QGINEDNAFVKGLEK | Trypsin |
| PSTVKADN | Chymotrypsin |

In some of the PCR reactions (High Fidelity PCR System; Roche, Bromma, Sweden), specific primers were used in combination with the degenerate ones. DNA sequences flanking the central region of the gene, where the peptide fragments originated from, were isolated using inverse PCR (IPCR). Briefly, genomic DNA was cleaved with the following restriction enzymes used separately; EcORV, SphI and PstI for the isolation of the start codon, and AccI, AsuI and finally HincII for the isolation of the stop codon sequences. The resulting fragments were religated upon themselves (Rapid DNA Ligation Kit; Roche) and the DNA was used in IPCR. To amplify the start and stop codon areas of the gene, specific primers were designed and used in a long template PCR (LTPCR) (Expand Long Template PCR System; Roche). All PCR products were cloned into pPCR-Script-Amp (Stratagene, La Jolla, Calif.) and sequenced using the Big Dye Cycle Sequencing Ready Reaction kit (Applied Biosystems, Warrington, England). Primers for amplification of genomic DNA were designed using the Oligo Primer Analysis software (Molecular Biology Insights, Cascade, Co). The signal peptide was deduced using the SignalP V1.1 World Wide Web Prediction Server Center for Biological Sequence Analysis (http://www.cbs.dtu.dk/services/SignalP/)

PCR Amplification of the Mid Gene

The complete 6.4 kb open reading frame of the mid gene was amplified by PCR using *M. catarrhalis* BcS strain genomic DNA as template. The oligonucleotide primers containing BamHI restriction enzyme recognition sequences were 5'-cgggatccgatggccgtggcggaatatgcc-3' (primer A, SEQ ID NO: 3) and 5'-cgcggatccgaaaagtgaaaacctgcaccaactgctgc-3' (primer B, SEQ ID NO: 4) generating a PCR product of 6391 base pairs. BamHI-digested insert was ligated into pET16(b) and the resulting plasmid pET16-MID was transformed into DH5α. Both strands of the cloned PCR product were sequenced.

To examine the full length mid gene in other *M. catarrhalis* strains, the primers A and B were used. In addition, primers used for narrowing down the sequence encoding the signal peptide were either primer A or 5'-tgtcagcatgtatcatttttttaagg-taaaccaccatg-3' (primer C; detecting the upper start codon, SEQ ID NO: 5) in combination with 5'-catcaattgcgatatgtctgg-gatcttg-31 (primer D; located at a conserved region just outside the signal peptide, SEQ ID NO: 6) generating 192- and 266-base pair long PCR products (using Bc5 genomic DNA as template), respectively. Furthermore, primer A or C in combination with 5'-cttcaccccatcagtgccatagacc-3' (primer E, SEQ ID NO: 7) were used for confirming the existence of the mid gene resulting in 1355- and 1429-base pair long fragments, respectively. The expand long template PCR system was used in all reactions and conditions were as recommended by the manufacturer (Roche, Bromma, Sweden).

Expression of the Mid Gene Product in *E. coli* and Cell Fraction

To express the mid gene product, pET16-MID was transformed into the expression host BL21 DE3, containing a chromosomal copy of the T7 RNA polymerase gene under lacUV5 control. The recombinant bacteria were grown in LB medium supplemented with 2% of glucose and ampicillin. Overexpression was achieved by growing cells to logarithmic-growth phase at $OD_{600}$ of 0.6 followed by addition of 1 mM IPTG. After 4 h of induction, bacteria were sonicated according to a standard protocol and the resulting proteins were analyzed by SDS-PAGE.

Localisation of recombinant protein from pET16-MID was carried out by osmotic shock as described. Briefly, broth cultures of induced and uninduced cells were harvested and resuspended in 30 mM Tris-HCl, pH 8, containing 20% sucrose. EDTA was added to a final concentration of 1 mM and the solution was slowly stirred at room temperature for 10 min. After centrifugation at 10,000 g for 10 min at 4° C., cells were resuspended in ice-cold 5 mM $MgSO_4$ and stirred for 10 min on ice. During this step, the periplasmic proteins were released into the buffer. The supernatant containing the periplasmic fraction was collected by centrifugation. Bacteria were completely lysed by lysozyme at a final concentration of 100 mg/ml followed by sonication. Finally, the soluble cytoplasmic and insoluble membrane fractions were collected.

Truncated MID-Derived Recombinant Proteins

Figure 10:
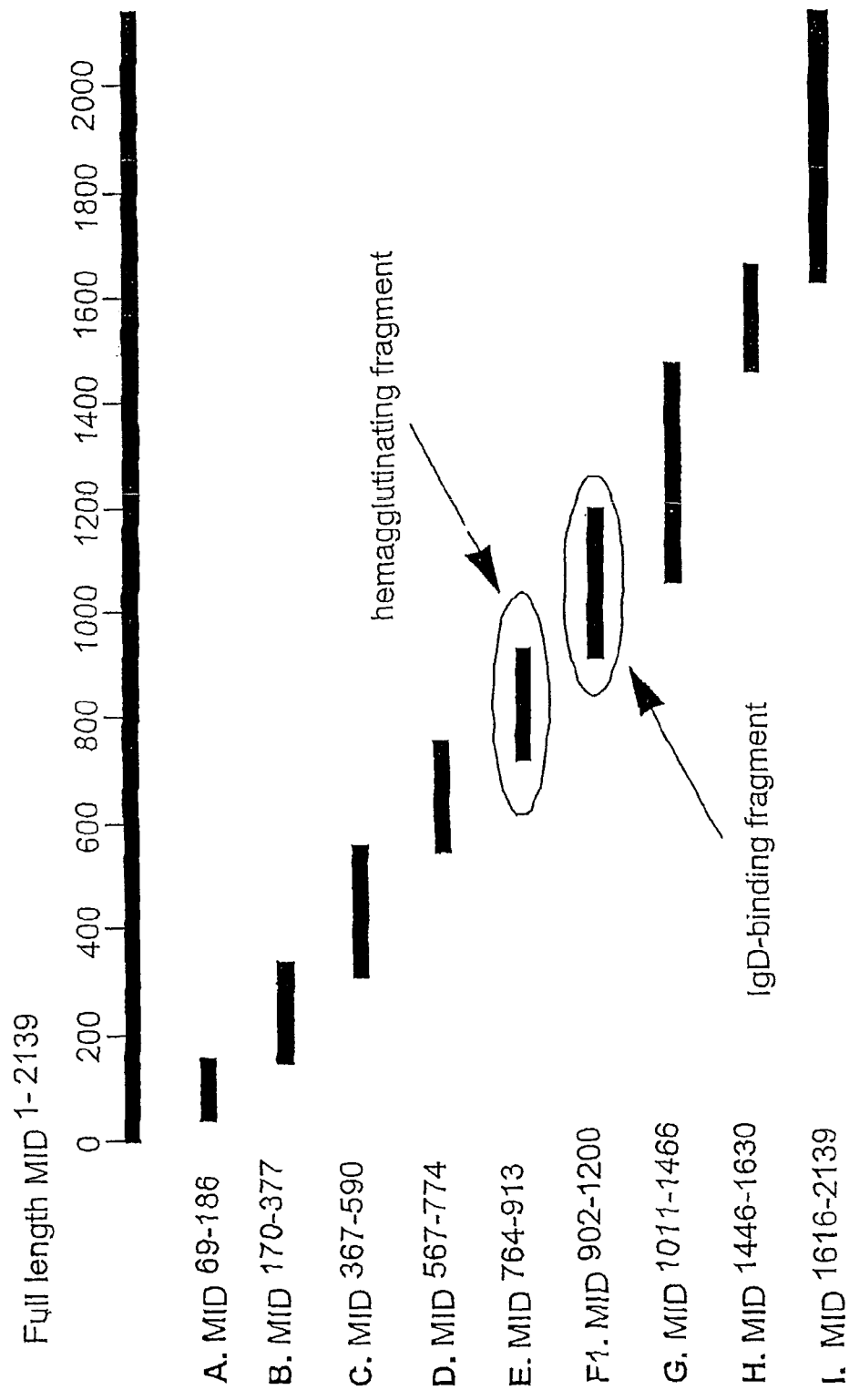
FIG. 10. MID764-913 (fragment E) and MID902-1200 (fragment F) is responsible for erythrocyte hemagglutination and IgD-binding, respectively. A series of truncated MID proteins (designated A to I) were manufactured. Recombinant proteins containing histidine tags in their C-terminals (A to H) or fused with maltose binding protein (I) were produced in *E. coli* and purified on nickel and amylose resin columns, respectively.

The different truncated MID fragments designated A to I with their specific sizes and primers for generating the proteins are shown in FIG. 10. The open reading frame of the mid gene from *M. catarrhalis* Bc5 (in pET26-MID) (Forsgren et al., 2001) was used as template. All MID constructs, except for MID367-590 (C), were amplified by PCR using specific primers introducing BamHI and HindIII restriction enzyme sites. Due to an internal HindIII restriction enzyme site in fragment C, an XhoI site was used instead of HindIII at the 3' end. All PCR products, except for MID1616-2139 (I), were cloned into pET26 (Novagen, Madison, Wis.). The PCR product encoding for the I fragment was cloned into pMAL-c2 (New England Biolabs, Beverly, Mass.). To avoid presumptive toxicity, the resulting plasmids were first transformed into the non-expressing host *E. coli* DH5α. Thereafter, plasmids encoding for fragments A to D, G and H were transformed into *E. coli* BL21(DE3), whereas the host BL21(DE3)-pLysS was used for vectors containing fragments E and F. Both *E. coli* strains were incubated in the presence of kanamycin, whereas chloramphenicol also was supplemented when BL21(DE3)-pLysS transformants were used. Fragment I was expressed in DH5α. Bacteria were grown to mid-log phase followed by induction with 1 mM isopropyl-1-thio-.β.-D-g-alactoside (IPTG). After 3.5 h, transformants were sonicated and the overexpressed proteins were purified according to the manufacturers instructions. Resulting recombinant proteins having a histidine tag or combined with maltose binding protein were purified on resins containing nickel amylose, respectively. The concentrations of the eluted proteins were determined using the BCA Protein Assay Kit (Pierce). Thereafter, recombinant proteins were analyzed by SDS-PAGE and Western blots.

Hemagglutination

Human erythrocytes were obtained from freshly drawn heparinized human blood. The erythrocytes were washed twice in PBS (pH 7.2) and suspended in PBS at a final concentration of 1%. Bacteria cultured in Nutrient Broth were harvested by centrifugation, washed and suspended to 1-2× 109/ml in PBS. Bacteria and erythrocyte suspension (50 µl of each) were mixed in round bottom microtiter plates (Sarstedt, Newton, N.C.). In some experiments, erythrocytes were mixed with MID-SEPHAROSE® or BSA-SEPHAROSE® in 150 µl PBS. Agglutination was read by the naked eye.

Cell Line and Adherence Assay

The lung carcinoma cell line A549 (type II alveolar epithelial cells; CCL-185) was obtained from ATCC. The cells were cultured in RPMI 1640 medium (Gibco BRL, Life Technologies, Paisley, Scotland) supplemented with 10% fetal calf serum, 2 mM L-glutamine, and 12 µg/ml gentamicin (referred to as culture medium). On the day before adherence experiments, cells were harvested, washed twice in gentamicin-free RPMI 1640 and added to 12-well tissue culture plates (Nunc, Roskilde, Denmark) at a concentration of 1×104 cells/well in 2.0 ml gentamicin free culture medium. Cells were thereafter incubated overnight at 37° C. in 5% $CO_2$. On the day of experiments, *M. catarrhalis* (−2×108) in PBS, 0.15% gelatin (Sigma) was inoculated onto the monolayers. In neutralization experiments with specific antisera, bacteria were preincubated with polyclonal antibodies (dilution {fraction (1/250) }). After 1 h at 4° C., bacteria were added to the epithelial cells. In all experiments, tissue culture plates were centrifuged at 3,000 g for 5 min and incubated at 37° C., 5% $CO_2$.

After 30 min, the infected monolayers were rinsed twice with PBS, 0.15% gelatin with gentle rocking to remove nonadherant bacteria and then treated with trypsin-EDTA (0.05% trypsin, 0.5 mM EDTA) to release them from the plastic support. Thereafter, the resulting cell/bacteria suspension was seeded to agar plates containing 1.1% isovitalex, 7.8% human blood, and finally 0.9% proteose peptone. Data was calculated from duplicate cultures.

Flow Cytometry Analysis

Human peripheral blood lymphocytes (PBLs) were isolated from heparinized blood from healthy donors by centrifugation on a step gradient of Ficoll-Isopaque (Lymphoprep; Pharmacia, Uppsala, Sweden). For flow cytometry analyses, a standard staining protocol was used with 0.5% BSA (w/v) in PBS as buffer. PBLs ($2.5 \times 10^5$ in 100 µl) were labeled with anti-CD3 or anti-CD19 mAbs with or without FITC-conjugated anti-IgD mAb on ice for 30 min according to the manufacturer's instructions. In blocking experiments, lymphocytes were also pre-incubated with anti-IgD immunoglobulins for 30 min. After two washes, 10 µg/ml of purified FITC-conjugated MID was supplemented to the cells followed by incubation for 45 min on ice. After 4 final washes with excess PBS 0.5% BSA, $10^5$ cells for each sample were analyzed in an EPICS® XL-MCL flow cytometer (Coulter, Hialeah, Fla.). Where appropriate, rabbit and goat pre-immune sera and mouse IgG1 and IgG2a were included as negative controls (Dakopatts).

Results

Extraction and Purification of MID

Solubilization of MID was a major obstacle in the process of purification. Amongst several detergents tested, only EMPIGEN® and n-Octyl-b-D glucoside alone at a final concentration of 3% solubilized MID from a suspension of *M. catarrhalis* efficiently as estimated by ELISA and Western blot. The two detergents were equally efficient. Triton X-100 alone did not solubilize MID, but Triton X-100 plus 0.01 M EDTA solubilized MID efficiently. CHAPS alone or CHAPS with EDTA or EDTA alone did not solubilize MID. In the following experiments, EMPIGEN® extraction was used for solubilization and subsequent purification of MID. When the EMPIGEN® extract of *M. catarrhalis* was applied to a Q-SEPHAROSE® column, all IgD-binding material was eluted from the column with 0.1% EMPIGEN® in 0.05 M Tris HCl, pH 8.8. No additional IgD-binding material could be eluted when a NaCl-gradient up to 1 M was applied to the same column. After concentration of the IgD-binding material obtained after separation on Q-SEPHAROSE®, fractionation of the extract was achieved by gel filtration in the presence of 0.1% EMPIGEN® on a SEPHACRYL™ S-400 column (FIG. 1). Most IgD-binding material was eluted in this first peak immediately after the void volume. MID was further purified by rechromatography of the first peak under the same conditions.

Figure 2:
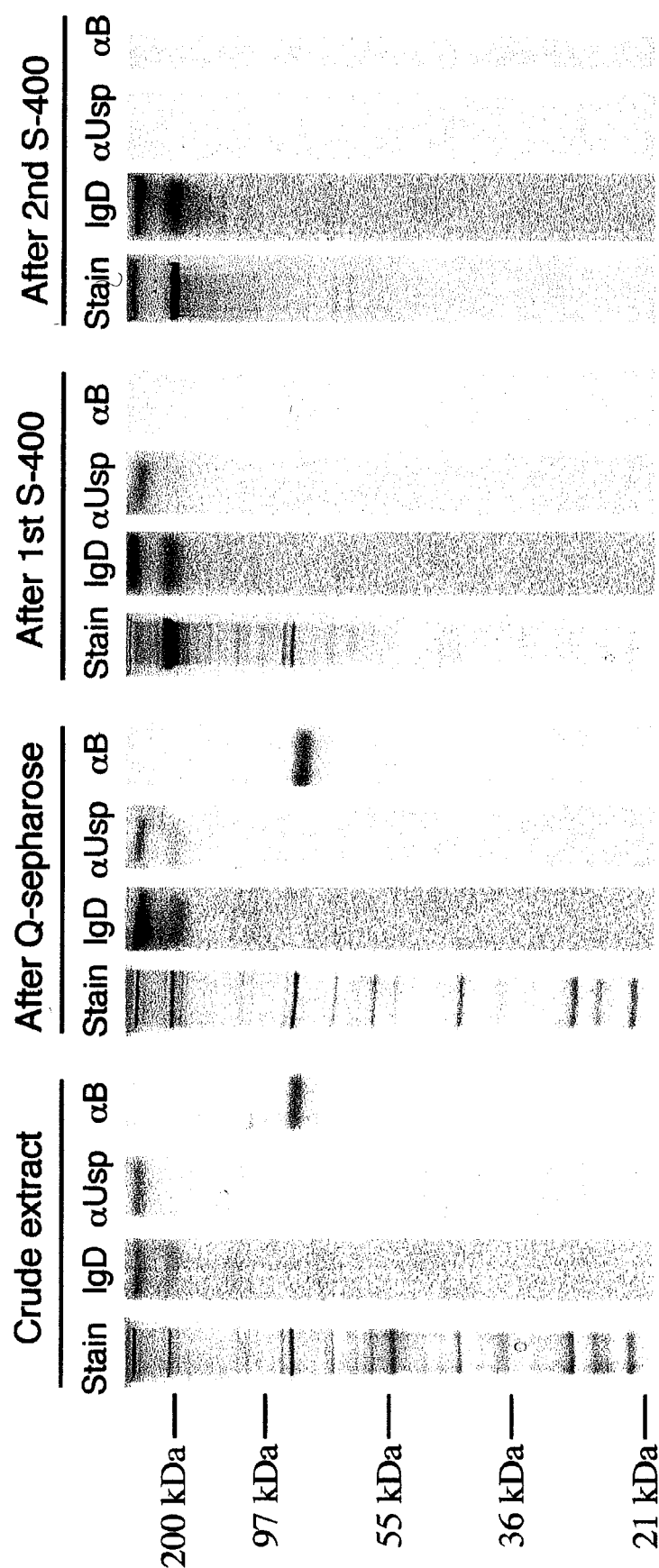
FIG. 2. Analysis on SDS-PAGE of fractions representing different purification steps of MID. The fractions are shown for crude extract in 3% EMPIGEN®, after an ion-exchange chromatography on Q-SEPHAROSE® column, and after the 1st and 2nd gelfiltrations on a SEPHACRYL™ S-400 column. Two gels were run simultaneously, one was stained with Coomassie blue (Stain) and one was blotted onto Immobilon-P membranes, probed with human IgD(κ) myeloma protein (IgD), anti-UspA (αUsp), or anti-CopB (βB) monoclonal antibodies followed by incubation with appropriate horseradish peroxidase-conjugated secondary antibodies. Molecular weights of marker proteins are indicated to the left.

FIG. 2 shows that after purification MID appeared as two bands, one 200 kDa-band and a second band with an apparent molecular mass of more than 1,000 kDa. Western blot experiments were performed to confirm that MID was not identical to the previously described outer membrane proteins UspA1 and 2 with an apparent molecular mass varying from 350 to 720 kD (8-10) or CopB with a molecular weight of 80 kDa. The crude EMPIGEN® extract of *M. catarrhalis* or partly purified preparations of MID were subjected to SDS-PAGE, transferred to Immobilon filters and blotted with antibodies to those *Moraxella* proteins and also with human IgD. As can be seen in FIG. 2, MID (as revealed by IgD-binding) is not identical with the outer membrane proteins UspA and Cop B.

Three attempts were made to determine the amino-terminal amino acid sequence of purified MID. Approximately 1000 pmol of MID was applied each time in an automated amino acid sequencer. Inasmuch as no amino acid phenylthiohydantoin derivatives were obtained, the amino-terminal end of the single MID polypeptide chain was probably blocked. It was recently determined that the *moraxella* UspA1 and UspA2 proteins, which are also resistant to Edman degradation, contained a pyroglutamyl residue that was removed by the treatment with pyroglutamate aminopeptidase. However, when MID purified from *M. catarrhalis* or recombinant MID was treated with this enzyme according to two different protocols (twice for each method) and then subjected to Edman degradation, no N-terminal amino acid sequence was obtained.

IgD-Binding Properties of MID

Crude EMPIGEN® extracts of *M. catarrhalis* and highly purified MID subjected to SDS-PAGE and transferred to filters were exposed to highly purified commercially available Ig-preparations representing all human Ig-classes and subclasses (Table III).

TABLE III

Summary of Western Blot and dot blot analyses showing the binding specificity of highly purified commercially available myeloma immunoglobulin D preparations against a crude EMPIGEN® extract of *M. catarrhalis* and highly purified MID. 200 kDa-protein Immunoglobulin in crude extract Purified MID

| Immunoglobulin | 200 kDa-protein in crude extract | Purified MID |
| --- | --- | --- |
| IgD(κ), IgD(λ) | + | + |
| IgG1(κ), IgG1(λ) | − | − |
| IgG2(κ), IgG2(λ) | − | − |
| IgG3(κ), IgG3(λ) | − | − |
| IgG4(κ), IgG4(λ) | − | − |
| IgA1(κ), IgA1(λ) | − | − |
| IgA2(κ), IgA2(λ) | − | − |
| IgM; (κ), IgM(λ) | − | − |
| IgE(κ) | − | − |

Only the two IgD preparations interacted with the MID-band in the 200 kDa-position in a similar fashion as shown for IgD in FIG. 2. When dot blot experiments were performed and purified MID in dilutions was first added to membranes and purified human myeloma proteins and secondary antibodies were subsequently applied, only the two IgD myelomas interacted with MID. One of the two myelomas detected as little as 0.001 µg of MID on the membrane. The specificity of the interaction between MID and IgD was further verified by using radiolabeled MID in other dot blot experiments In FIG. 3, it is demonstrated that MID effectively bound four IgD myeloma sera. A distinct reaction could be detected in the range 0.03-4 µg of IgD. For the IgD standard serum (B.W.) reactivity was seen at even lower concentrations (not shown). In contrast, 6 different Ig myeloma sera representing IgG, IgA and IgM showed no visible reaction with MID at 4 µg.

Figure 3:
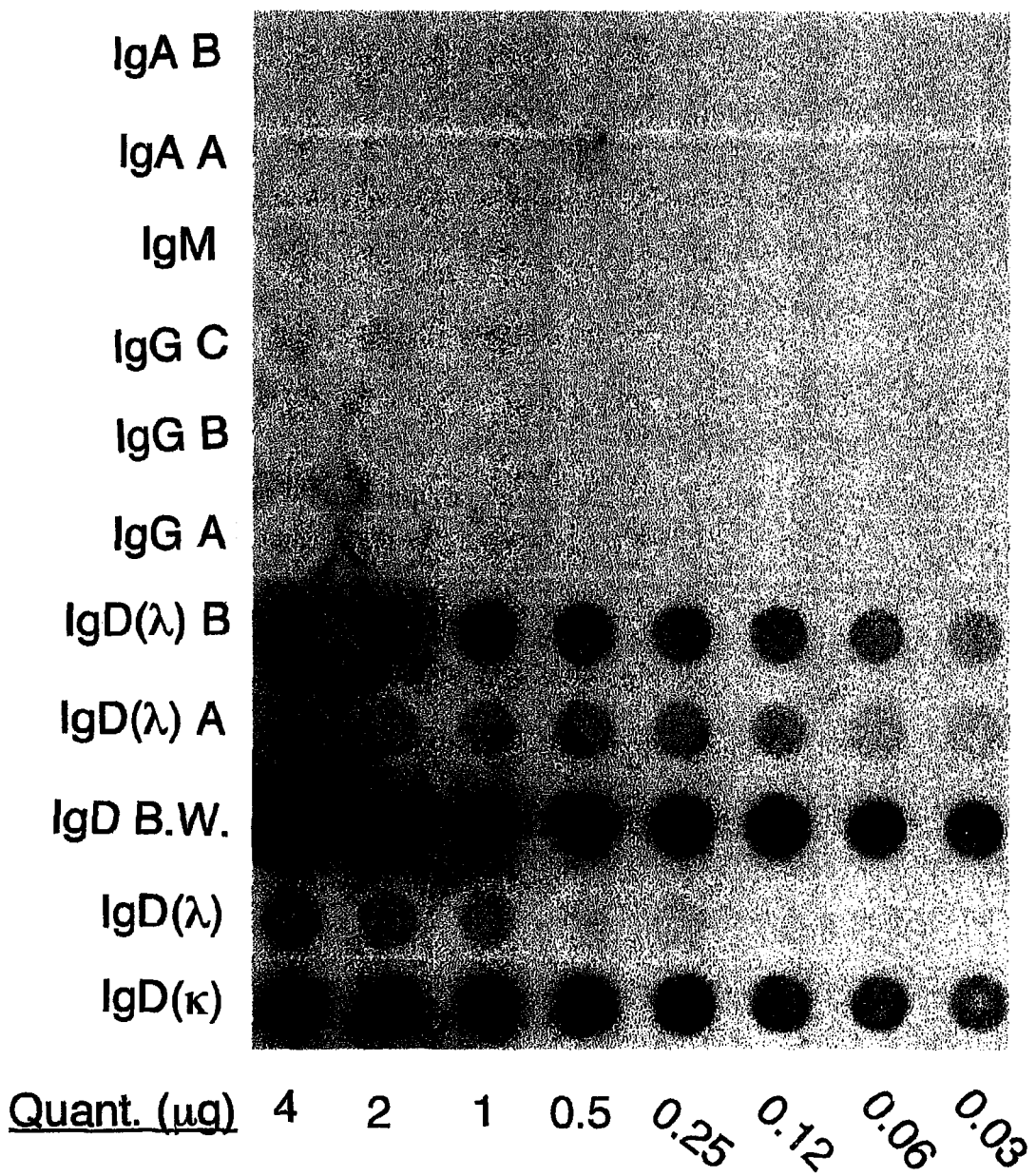
FIG. 3. Binding of MID to human myeloma sera representing different immunoglobulin classes. All sera were diluted in two-fold steps (4 to 0.3 μg) and applied to a nitrocellulose membrane. After saturation, washing and blocking, an [125I]-MID-labeled probe was added. After overnight incubation and additional washings, specific MID-IgD binding was visualized by autoradiography.
Figure 4:
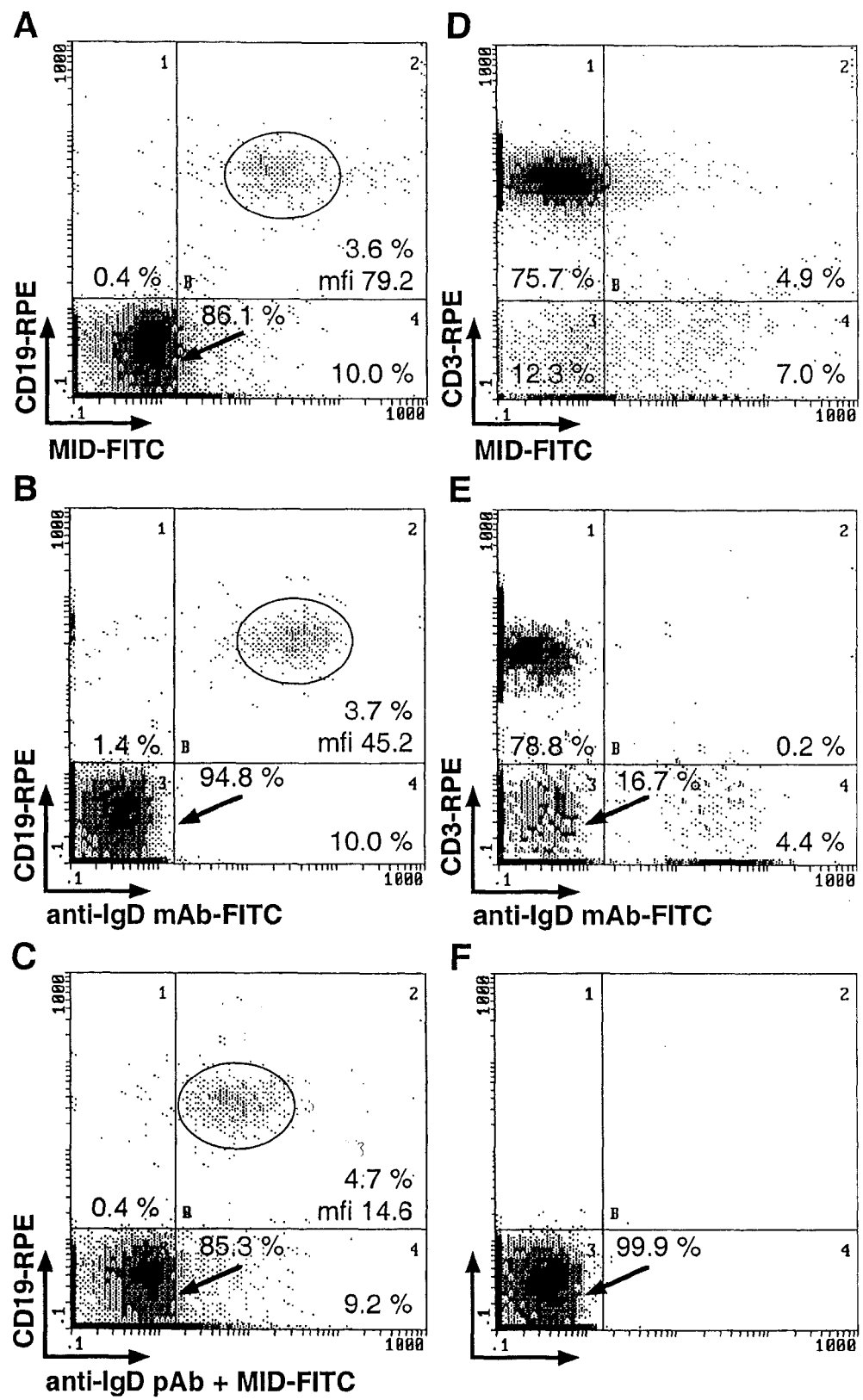
FIG. 4. IgD-bearing B cells specifically bound FITC-conjugated MID. PBLs stained with RPE-conjugated mAbs against CD19+ (A) or CD3+ (D) followed by incubation with MID-FITC were compared to PBLs incubated with anti-CD19 mAb in addition to an anti-IgD mAb (B). Double staining with CD3+ and anti-IgD mAb is demonstrated in (E). In (C), a panel with PBLs pre-incubated with a rabbit immunoglobulin fraction against human IgD followed by addition of anti-CD19 mAb and MID-FITC is shown. A control sample with no antibodies or MID-FITC is also included (F). PBLs were isolated from heparinized human blood using Lymphoprep one-step gradients. Lymphocytes ($2.5 \times 10^5$) were incubated with the appropriate anti-bodies, washed and further incubated with MID-FITC (10 μg/ml). All incubations were performed on ice and after final washings, PBLs were analyzed by flow cytometry. In this particular experiment, 68% of the total lymphocyte population was gated and analyzed. Less than 2% of the cells were labeled when iso-matched mAbs were included as negative controls. A pre-immune rabbit serum did not significantly block MID-FITC binding to the IgD BCR (not shown). An experiment with a typical donor out of three separate ones analyzed is shown.

Purified MID specifically attracted human soluble IgD as revealed in dot and Western blots (FIGS. 2 and 3, Table III). To test whether MID bound to the surface-expressed B cell receptor (BCR) IgD, human peripheral blood lymphocytes (PBLs) were isolated. FITC was conjugated to MID followed by incubation with PBLs for 45 min on ice. In parallel, PBLs were labeled with RPE-conjugated mAbs directed against the T cell marker CD3 or the B cell specific surface antigen CD19 and subsequently analyzed by flow cytometry (FIG. 4). Interestingly, a large fraction of $CD19^+$ lymphocytes bound significant amounts of MID-FITC (FIG. 4A), whereas T cells (CD3+ lymphocytes) only displayed a non-specific background binding (FIG. 4D). The MID-FITC signal corresponded well with CD19+ cells incubated with anti-IgD mAbs revealing IgD-positive B cells (FIG. 4B). To further elucidate the specificity of MID-FITC binding to IgD bearing CD19+ lymphocytes, PBLs were preincubated with a rabbit anti-human IgD immunoglobulin fraction. After incubation and washings, MID-FITC binding was analyzed by flow cytometry according to the standard procedure. The antiserum almost completely inhibited specific MID-FITC binding to the IgD BCR when compared to cells incubated with the pre-immune serum. Mean fluorescence intensity decreased from 79.2 to 14.6 arbitrary units. Similar results were obtained with goat immunoglobulins raised against IgD (not shown). Thus, IgD-expressing B cells promoted specific MID-FITC binding to the surface-expressed BCR IgD.

Cloning of the Gene Encoding MID and DNA Sequence Analysis

Figure 5:
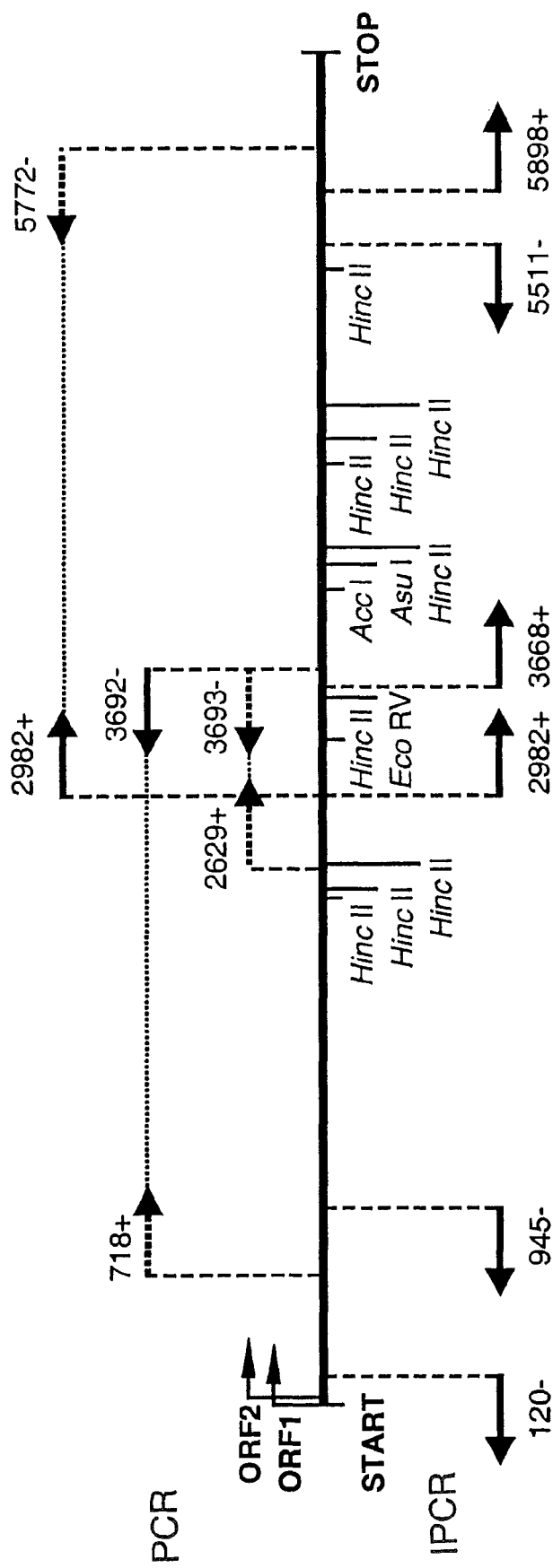
FIG. 5. Schematic map of the mid gene showing the cloning strategy. Oligonucleotide primers used for DNA amplification are indicated by arrows placed above (PCR) and below (inverse PCR [IPCR]) the relevant sequences. Degenerated primers based upon the amino acid sequences outlined in Table II and specific primers are shown by broken and solid lines, respectively.

Degenerate primers were designed according to the obtained amino terminal sequences of four peptide fragments originating from MID (Table II) and were used in PCRs in all possible combinations. The specific primers 2982+ and 3692– (FIG. 5) were synthesized using the deduced sequence of a distinctive PCR product generated with the degenerate primer pair 2629+/3693–. A PCR reaction using the specific primers in combination with the degenerate ones (718+ and 5772–) resulted in totally 5054 by of the gene coding for MID. Flanking sequences surrounding the core of the mid gene were obtained by inverse PCR (IPCR). IPCR on EcORV- and AsuI/AccI-digested *M. catarrhalis* genomic DNA with the primer-pairs 2982+/945– and 3668+/120–, respectively, provided the sequence for the start-codon area. In addition, IPCR on HincII-digested *moraxella* genomic DNA with the primer-pair 5898+/5511– generated the 3' sequence including the stop-codon. The complete nucleotide sequence of the gene encoding MID in *M. catarrhalis* Bc5 is shown in SEQ ID NO: 2 and the resulting amino acid sequence is shown in SEQ ID NO: 1. Two alternative open reading frames were revealed and are 20' indicated at amino acid positions 1 and 17, see FIG. 6). Consequently, the length of the mid gene product was either 2123 or 2139 amino acids. In addition to a putative ribosome-binding site (AAGG), –10 (TAATTA) and –35 (TTGAAT) consensus sequence boxes were identified. Furthermore, 62 bases downstream of the TAA stop-codon an inverted repeat was found with the potential of stem-loop formation that is necessary for transcriptional termination. To get an overview of the similarity and identity between different mid genes, the sequences of the five ORF MID proteins were analyzed. For 4 strains, the degree of identity and similarity was .gtoreq.75.8% and .gtoreq.78.3%, respectively (FIG. 7). In contrast, slightly lower values, .gtoreq.65.3% and .gtoreq.71.2%, respectively, were obtained for the fifth isolate (RH4). Identity and similarity with UspA1 was 5.5-11.1% and 8.3-17.9%, respectively, and with UspA2 6.5-7.5% respectively 11.1-12.4%.

The Mid Gene can be Detected in all *M. catarrhalis* Strains

By PCR analyses, the mid-I gene was detected in all 118 *M. catarrhalis* strains, whereas the *Moraxella* (nesseria)-related controls were negative. In addition, the size of the mid-1 gene was confirmed using primers spanning the whole gene including the start and stop codons. Analysis of the deduced amino acid sequence of MID differs from UspA1, UspA2 and the protein described in U.S. Pat. No. 5,808,024

Figure 8:
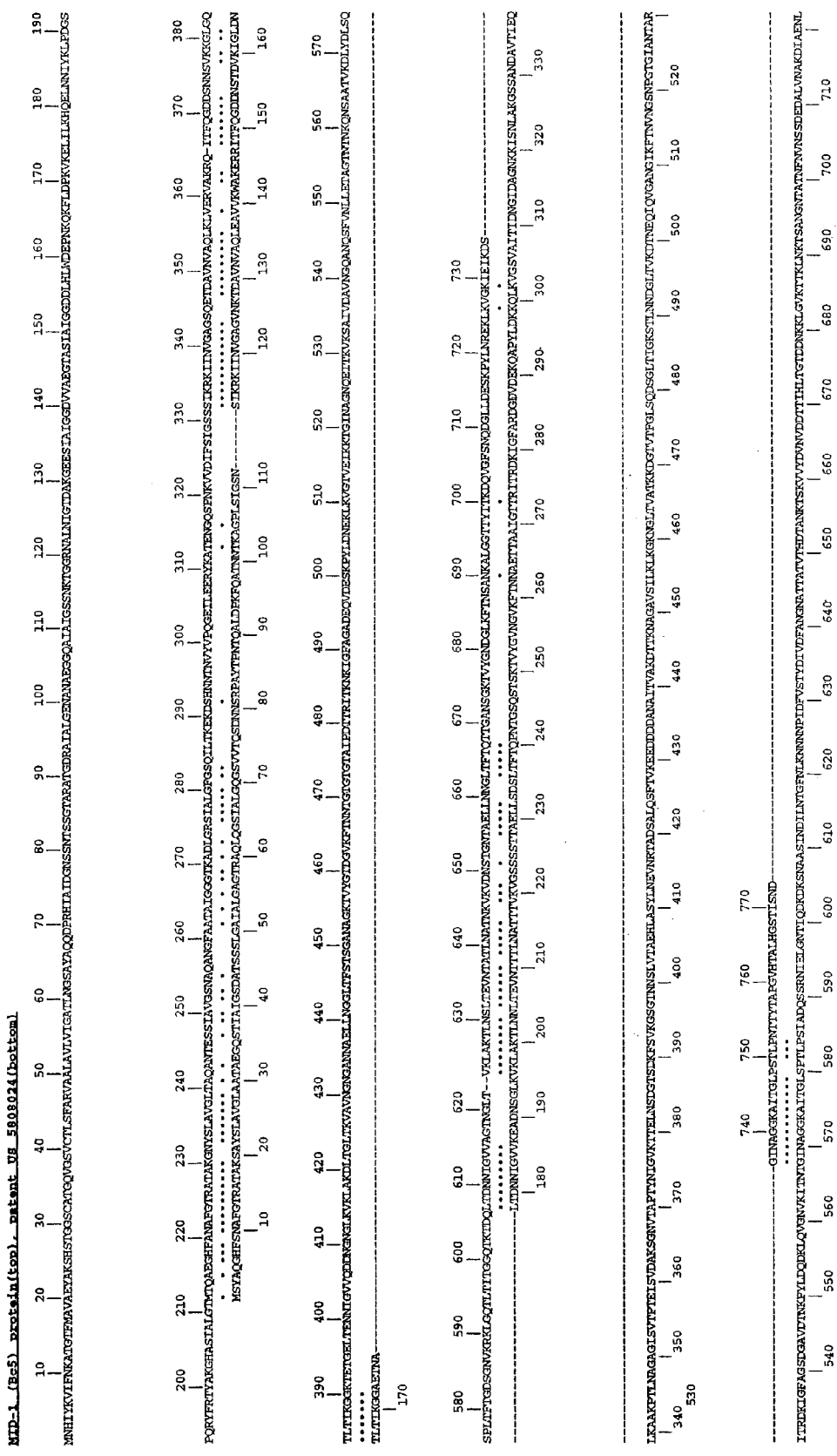
FIG. 8. Comparison of the amino acid sequence of MID (SEQ ID NO: 1) with the protein presented in U.S. Pat. No. 5,808,024 (SEQ ID NO: 16).
Figure 8:
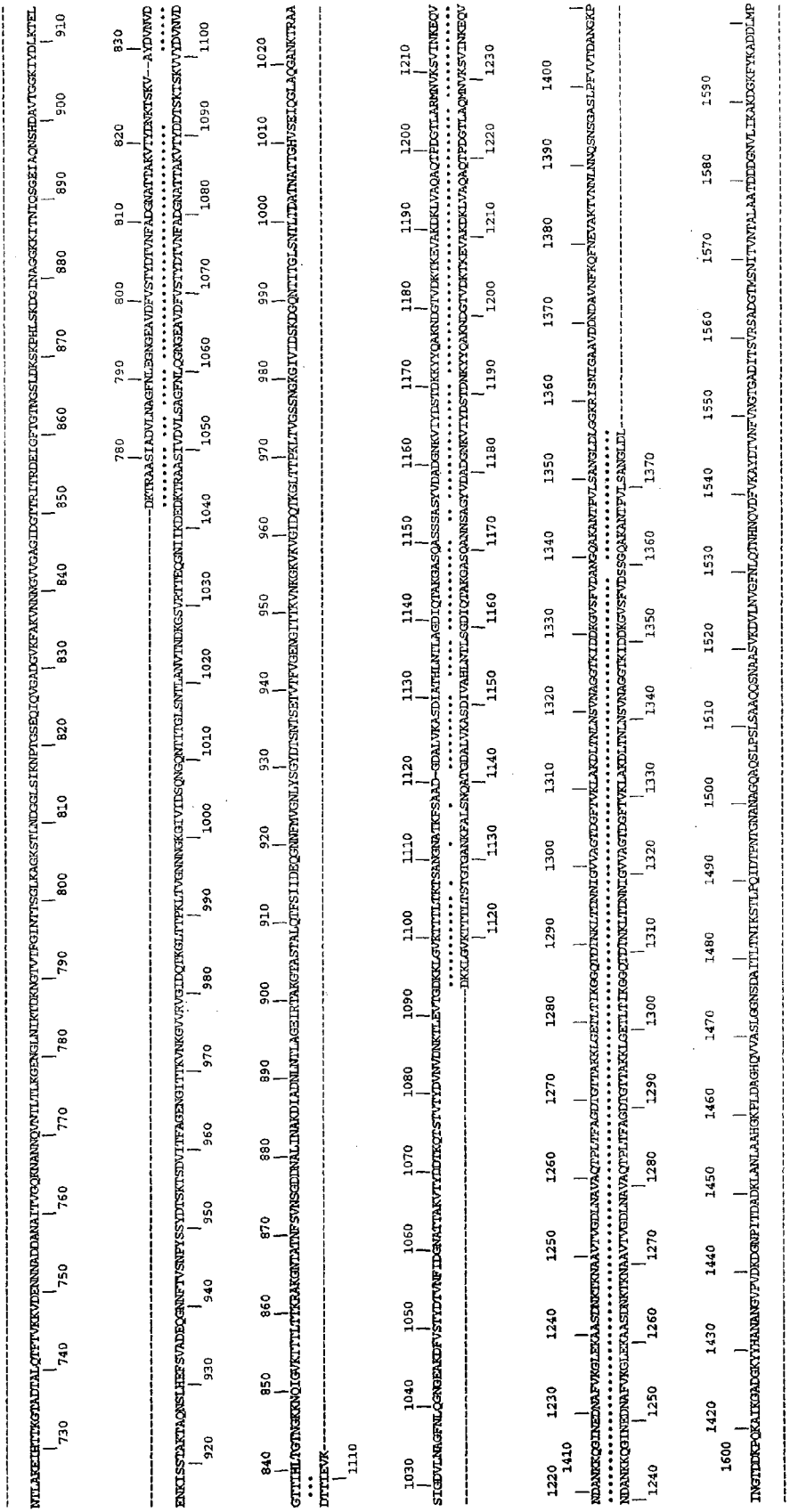
Figure 8:
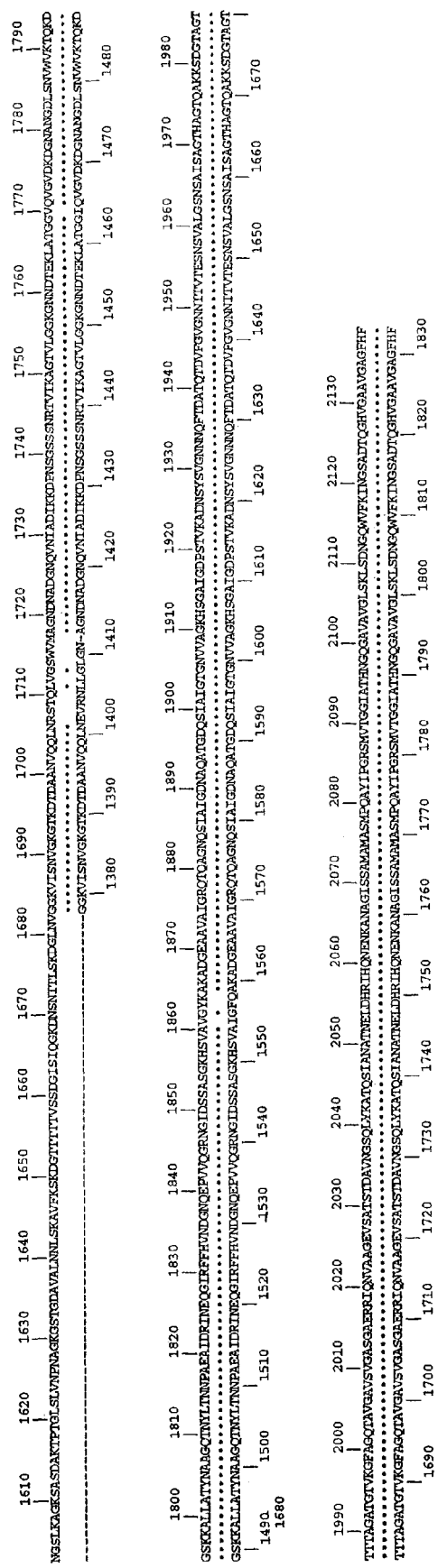

The open reading frame defined a protein with a calculated molecular mass of just below 220 kDa that readily corresponded to the empirical value of approximately 200 kDa found by SDS-PAGE. The N-terminal amino acid sequence showed the typical characteristics of a signal peptide with a potential cleavage site between amino acids 66 and 67. Despite that the first amino acid after the signal peptidase cleavage site most likely was a glutamine residue, any sequence could not be determined by Edman degradation. Furthermore, no amino acid sequence was obtained after pyroglutamate aminopeptidase treatment. The predicted amino acid sequence was also subjected to a hydrophobicity profile analysis by the method of Kyte and Doolittle and showed mainly hydrophilic properties except for the putative signal peptide that was strongly hydrophobic. The deduced amino acid sequence for MID differs significantly from those for the protein described in U.S. Pat. No. 5,808,024 and also from the UspA-proteins (FIGS. 7 and 8).

The mid gene is distributed in all *M. catarrhalis* strains. To investigate whether or not the mid gene existed in all *M. catarrhalis* strains, primers were chosen based upon a conserved area upstream of the open reading frame (ORF) and a conserved area downstream including the stop codon sequence (Forsgren et al., 2001). The mid gene was detected in all 86 clinical isolates and 7 type strains analyzed, and the length of the genomic mid DNA was approximately 6,000 base pairs. The existence was further verified by Southern blots using a probe containing a sequence selected from the 3'-end of the gene. Southern blot experiments revealed that the *moraxella* strains contained only one mid gene.

Expression of Recombinant MID in *E. coli*

Figure 9:
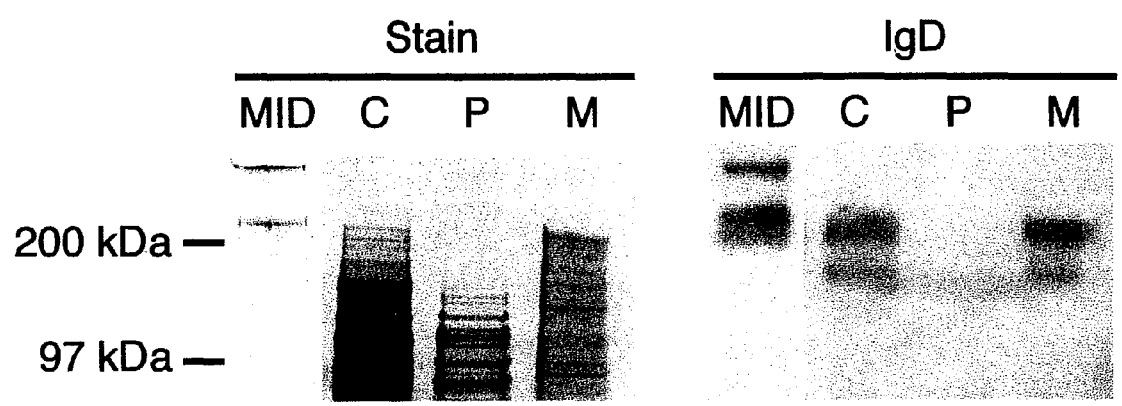
FIG. 9. Recombinantly expressed MID retained its IgD-binding capacity. The left panel shows a Coomassie brilliant blue stained gel and the right panel a Western blot probed with human IgD. Native MID protein (MID) was run and compared to cytoplasmic (C), periplasmic (P), and membrane (M) fractions. Numbers on the left indicate a molecular weight standard. *E. coli* BL21DE3 containing pET16-MID were induced for 4 h by IPTG. Cellular fractions were collected and proteins were separated by two SDS-PAGE that was run in parallel and either stained with Coomassie brilliant blue or blotted onto an Immobilon-P membrane. The membrane was probed with human IgD followed by incubation with a horse-radish peroxidase-conjugated secondary antibody.

To confirm that the cloned mid gene corresponded to the purified IgD-binding protein, the gene including the predicted signal sequence and start codon was subcloned into the expression vector pET16(b) and thereby under the control of a T7 promoter. The resulting pET16-MID was subsequently transformed into *E. coli* BL21 DE3 followed by induction with IPTG. Bacterial cells were lysed and subfractionated, and recombinant MID was localized by Western blots using human IgD as a probe. Important verifying characteristics of MID were provided from the expression experiments (FIG. 9). Firstly, following induction, cells containing pET16-MID were able to produce recombinant MID confirming the correct reading frame of the gene. Secondly, recombinant MID (as shown by SDS-PAGE) displayed a molecular mass of approximately 200 kDa, corresponding to the 217 kDa calculated value from the amino acid sequence. Thirdly, the recombinant protein was indeed the mid gene product in *E. coli* as its IgD-binding phenotype was confirmed by Western blot analysis. Total protein from *E. coli* containing induced pET16(b) vector without insert did not display any IgD-binding capacity (data not shown). Fourthly, the subcellular localization of the recombinant protein showed that MID was equally located in the cytoplasmic and the membrane fractions, but not in the periplasmic space. The localization of MID's in the membrane fraction correlated very well with the known outer membrane localization in *M. catarrhalis*. IgD-binding is preserved in 238 amino acids of MID To in detail determine the MID IgD-binding region, 9 sequences derived from the full length MID were cloned into pET26b(+) and expressed in *E. coli*. The recombinant proteins covered the entire MID sequence and their individual lengths and positions were as demonstrated in FIG. 10. The recombinant proteins comprising amino acid residues 69-1111 or 1011-2139 of MID did not bind IgD as revealed in Western and dot blots. In contrast, the protein MID902-1200 (protein fragment F1) attracted IgD-, strongly suggesting that the single IgD-binding region of MID was within that particular sequence.

Figure 11:
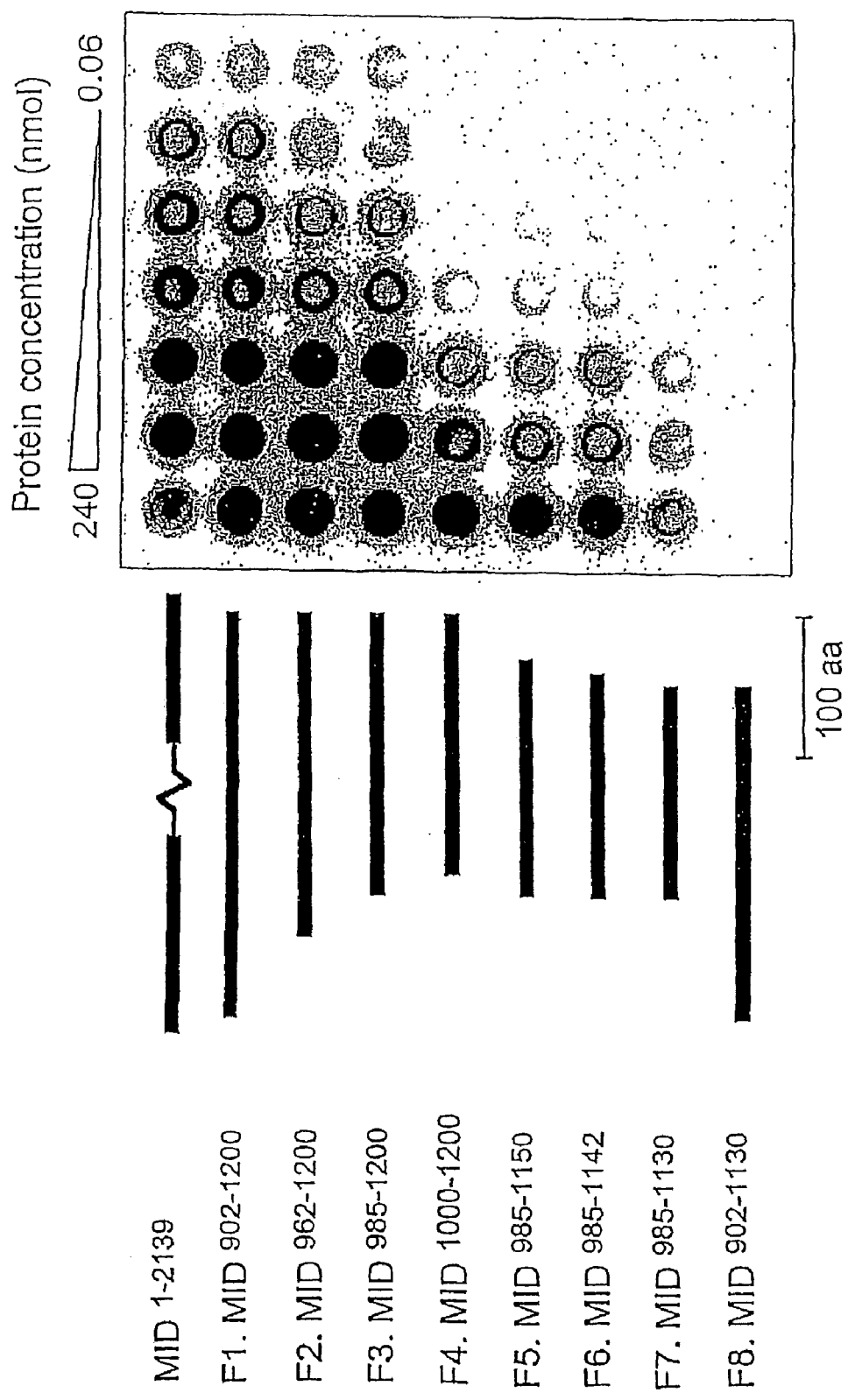
FIG. 11. MID962-1200 (fragment F2) has a conserved IgD-binding capacity compared with full length MID1-2139. Equimolar concentrations (range 240 to 0.06 nmol) of purified full length MID1-2139 and 8 truncated MID fragments (F1 to F8) were analyzed for IgD-binding by dot blots. The proteins MID902-1130 (F8), MID985-1130 (F7), and MID1000-1200 (F4) did not attract IgD, whereas all other fragments bound IgD. DNA encoding for the various truncated MID proteins were cloned into the expression vector pET26b(+) and produced in *E. coli*. The recombinant proteins containing His-tags were purified and dot blotted onto a nitro-cellulose membrane. The membrane was probed with human IgD followed by secondary HRP-conjugated polyclonal antibodies that were used for detection.

To pinpoint the sequence responsible for the IgD-binding, the truncated MID902-1200 was systematically shortened at the N- and C-terminal ends (FIG. 11). Equimolar concentrations of the various recombinant proteins were compared to native full length MID1-2139 isolated from *M. catarrhalis*. The different recombinant proteins were diluted in four-fold steps, added to membranes and incubated with human IgD. On a molar basis, an essentially preserved IgD-binding capacity was detected for the truncated MID protein stretching from amino acid residue 962 to 1200. The shortest truncated protein still interacting with IgD-was localized between MID985 and MID1142 (fragment F6). The IgD-binding property was lost when the N-terminus was reduced to the MID1000 residue (fragment F4) or when the C-terminal was shortened to MID1130 (fragment F7). Finally, a fragment (MID902-1130; F8) with a longer N-terminal and a shorter C-terminal (compared to MID985-1200; F3) was also manufactured and analyzed. However, this truncated MID did not interact with IgD, suggesting that the binding capacity was depending on a longer-C-terminal.

To further characterize the specific MID-dependent IgD-binding, an IgD ELISA was constructed using human IgD as bate. All the recombinant truncated MID fragments were subjected to ELISA followed by incubation with a specific rabbit anti-serum directed against MID902-1200. The ELISA was developed using HRP-conjugated goat anti-rabbit polyclonal antibodies. The same pattern as with the dot blot (FIG. 11) was observed, i.e. fragments F4, F7, and F8 was not attracted to the solid phase IgD, whereas the other fragments bound to a variable degree compared to full length MID (not shown).

Optimal M1D962-1200-IgD Interaction is Depending on a Tetramer Structure

Figure 12:
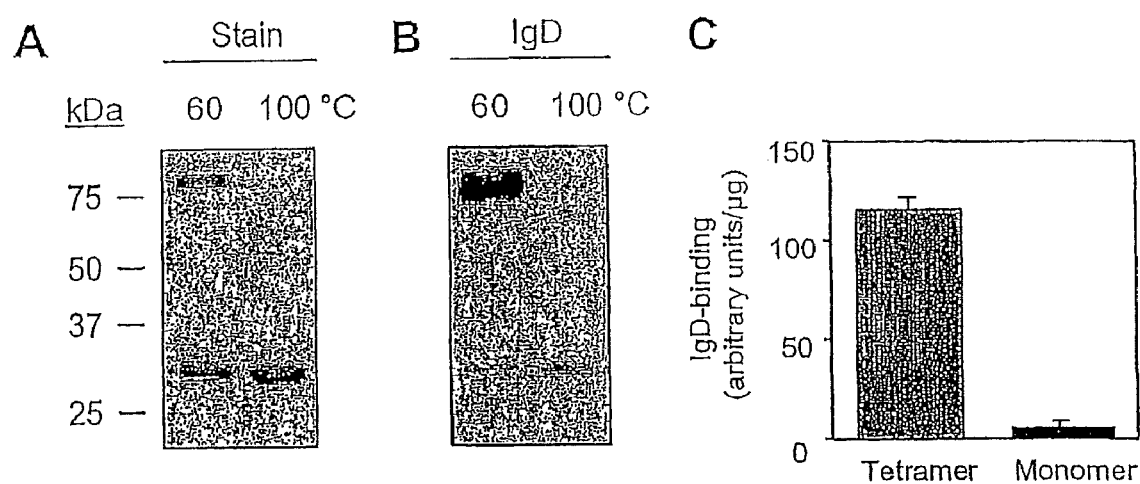
FIG. 12. A tetrameric structure of MID962-1200 (F2) is a prerequisite for optimal IgD-binding. (A), SDS-PAGE of MID962-1200 after treatment at 60° C. separates monomers and tetramers. After heat treatment at 100° C. monomers only can be detected. (B), Corresponding Western blot with IgD as probe reveals weak IgD-binding to monomers. (C), Mean IgD-binding to tetramers and monomers, respectively in 6 different experiments. IgD-binding is shown as arbitrary units/μg protein. MID962-1200 was treated in SDS-sample buffer at 60° C. or 100° C. for 10 min, and subjected to SDS-PAGE and Western blot analysis. The resulting Coomassie-stained gel and Western blot were analyzed by densitometry. The percentage of protein migrating as tetramer or monomer was calculated and compared with the IgD-binding capacity.

To shed light upon the need for a tetramer structure in order to obtain an optimal IgD-binding, MID962-1200 (F2, SEQ ID NO: 10) was incubated at 60 or 100° C. followed by analysis on SDS-PAGE and Western blots. MID962-1200 formed both a monomer and a tetramer after pre-treatment at 60° C. (FIG. 12A). The tetrameric structure was, however, disrupted at 100° C. and resulted in a monomeric form, which displayed a considerably weaker binding to IgD when examined in Western blots (FIGS. 12A and B). To investigate the capability of the tetramer to bind IgD in comparison with the monomeric form, the MID962-1200 fragment, SEQ ID NO: 10, was subjected to analysis at 60° C. in 6 different experiments. The heat treated protein was subjected to SDS-PAGE and the IgD-binding activity was analyzed by Western blots. Resulting gels and filters were analyzed by densitometry and the protein concentration (density) of the monomer was divided with the corresponding tetramer concentration. The obtained value (%) was related to the concentration (µg) of total protein loaded on the gels. Interestingly, when IgD-binding to the tetrameric respectively monomeric forms were compared, a 23-fold more efficient binding to IgD was found with the tetrameric MID962-1200 (FIG. 12C). *M. catarrhalis* IgD-binding protein (MID) hemagglutinates human erythrocytes To investigate a putative involvement of MID in hemagglutination, a series of clinical isolates that either expressed MID or by phase variation had shut off the mid gene was selected. Interestingly, all out of 21 isolates expressing MID hemagglutinated human erythrocytes, whereas only four out of the MID-negative strains (n=21) hemagglutinated the red blood cells. An almost full correlation between hemagglutinating capacity and MID expression was observed. UspA1/2 expression was similar and irrespective of the MID expression.

These initial experiments prompted us to examine whether or not purified MID protein from the model strain *M. catarrhalis* Bc5 (Forsgren et al., 2001) hemagglutinates erythrocytes. To mimic the bacterial surface, MID was conjugated to SEPHAROSE® beads and incubated with the human erythrocytes. Bovine serum albumin (BSA) linked to SEPHAROSE® was included as a negative control. Interestingly, the human erythrocytes were hemagglutinated in the presence of MID-SEPHAROSE®, whereas BSA-SEPHAROSE® did not interfere with the erythrocytes (data not shown). The hemagglutinating domain of MID is located between amino acid residues Alanine764 and Serine913

To dissect the molecule and pin-point the specific site of the molecule that was responsible for the hemagglutination, a series of truncated DNA fragments of the mid gene was cloned and recombinantly expressed in *E. coli* (FIG. 10). Polyclonal antibodies against the truncated MID proteins were raised in rabbits and used in an ELISA. In preparatory experiments, antibodies to MID and the MID-derived proteins were titrated to give similar values when tested in ELISA against respective antigens. The capacity of the truncated MID proteins to bind to lysed erythrocytes was then measured in ELISA using the specific antibodies at appropriate concentrations. MID or MID764-913 (fragment E) gave higher ELISA values (4 to 16 times) as compared to the other truncated MID proteins. Thus, the hemagglutinating structure of MID seemed to be located within amino acid residues 764-913 of MID (SEQ ID NO: 8).

MID764-913 (Fragment E, SEQ ID NO: 8) Binds Directly to Both Erythrocytes and Type II Alveolar Epithelial Cells To further confirm the importance of MID764-913 as an adhesin, MID and a selection of the truncated MID-derived proteins were radiolabeled and tested in direct binding experiments with human erythrocytes and alveolar epithelial cells (FIG. 13). Both [125I]-MID and [125I]-MID764-913 strongly bound to erythrocytes, whereas the truncated MID fragments MID367-590 (fragment C), MID902-1200 (F), MID1011-1446 (G), and MID1616-2139 (I) did not bind above background levels (FIG. 13A). In parallel, the alveolar epithelial cell line A549 also attracted both the full length [125I]-labeled MID and the truncated MID764-913 (FIG. 13B). All the other fragments did not bind to the epithelial cells. Taken together, the fragment MID764-913 (SEQ ID NO: 8) was the crucial part of the adhesin MID that mediated the attachment to mammalian cells.

Figure 14:
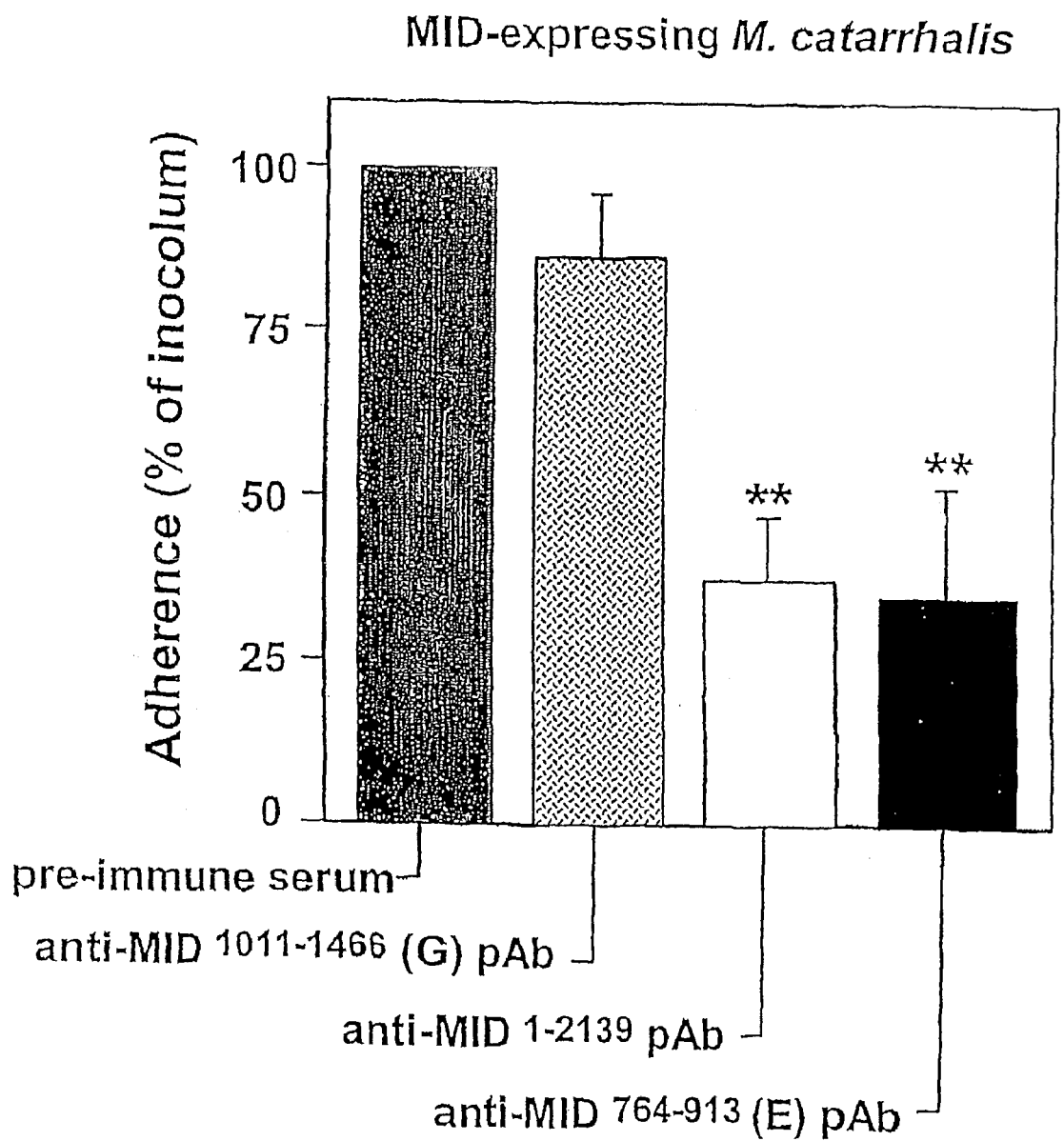
FIG. 14. Adhesion of MID-expressing *M. catarrhalis* to epithelial cells depends on the amino acid residues MID764-913 (fragment E). A decreased adhesion to epithelial cells was observed with MID-expressing bacteria coated with rabbit anti-MID1-2139 or anti-MID764-913 polyclonal antibodies compared to a pre-immune serum or anti-MID1011-1446 (fragment G) pAb. Bacteria were preincubated with the pre-immune serum or specific antisera for 1 h at 4° C. Bacteria were added to the epithelial cells followed by centrifugation and incubation for 30 min at 37° C. After washings, cells were treated with trypsin-EDTA and the suspensions were plated on blood agar plates. Colony forming units were counted after an overnight incubation. The adherence ratio (cfu added/cfu adhered) was calculated. Results are shown as mean values of 4 separate experiments with duplicates. Error bars indicate SD. * $P \leq 0.001$,  $P \leq 0.01$ and * $P \leq 0.05$.

Antibodies to Full Length MID1-2139 and M1D764-913 Inhibit Adherence of *M. catarrhalis* to Type II Alveolar Epithelial Cells To further analyze the influence of full length MID and MID764-963 on *M. catarrhalis* adherence to type II alveolar epithelial cells, a MID-expressing and a MID-deficient *M. catarrhalis* strain were preincubated with antibodies to MID and subsequently added to alveolar epithelial cells for adherence. As demonstrated in FIG. 14, polyclonal antibodies directed against full length MID1-2139 and MID763-913 (fragment E, SEQ ID NO: 8) effectively inhibited adherence for the MID-expressing isolate. In contrast, pre-immune serum and a pAb directed against MID1011-1466 (fragment G) did not significantly interfere with adhesion.

REFERENCES

1. Forsgren, A. and Grubb, A. (1979) Many bacterial species bind human IgD. J. Immunol. 122, 1468-1472.
2. Banck, G. and Forsgren, A. (1978) Many bacterial species are mitogenic for human blood lymphocytes. Scand. J. Immunol. 8, 347-354.

3. Calvert, J. E. and Calogeres, A. (1986) Characteristics of human B cells responsive to the T-independent mitogen *Branhamella catarrhalis*. Immunology 58, 37-41.
4. Forsgren, A., Penta, A., Schlossman, S. F. and Tedder, T. F. (1988) *Branhamella catarrhalis* activates human B lymphocytes following interactions with surface IgD and class I major histocompatibility complex antigens. Cell. Immunol. 112, 78-88.
5. Janson, H., Carin, B., Cervin, A., Forsgren, A., Bjork-Magnusdottir, A., Lindberg, S. and Runer, T. (1999) Effects on the ciliated epithelium of protein D-producing and -nonproducing nontypeable *Haemophilus influenzae* in nasopharyngeal tissue cultures. J. Infect. Dis. 180, 737-746.
6. Sasaki, K. and Munson Jr., R. S. (1993) Protein D of *Haemophilus influenzae* is not a universal immunoglobulin D-binding protein. Infect. Immun. 61, 3026-3031.
7. Helminen, M. E., Beach, R., Maciver, I., Jarosik, G., Hansen, E. J. and Leinonen, M. (1995) Human immune response against outer membrane proteins of *Moraxella (Branhamella) catarrhalis* determined by immunoblotting and enzyme immunoassay. Clin. Diagn. Lab. Immunol. 2, 35-39.
8. Aebi, C., Maciver, I., Latimer, J. L, Cope, L. D., Stevens, M. K., Thomas, S. E., McCracken, G. H. and Hansen, E. J. (1997) A protective epitope of *Moraxella catarrhalis* is encoded by two different genes. Infect. Immun. 65, 4367-4377.
9. Cope, L. D., Lafontaine, E. R., Slaughter, C. A., Hasemann, C. A. Jr., Aebi, C., Henderson, F. W., McCracken, G. H. Jr and Hansen, E. J. (1999) Characterization of *Moraxella catarrhalis* uspA1 and uspA2 genes and their encoded products. J Bacteriol 181, 4026-4034.
10. Klingman, K. L. and Murphy, T. F. (1994) Purification and characterization of a high-molecular-weight outer membrane protein of *Moraxella(Branhamella) catarrhalis*. Infect. Immun. 62, 1150-1155.
11. WO 98/28333
12. Sasaki, K., Harkness, R. E., Loosmoore, S. M. and Klein, M. H. (1998) U.S. Pat. No. 5,808,024.
13. Fitzgerald, M., Mulcahy, R., Murphy, S., Keane, C., Coakley, D. and Scott, T. (1997) A 200 kDa protein is associated with haemagglutinating isolates of *Moraxella (Branhamella) catarrhalis*. FEMS Immun. Med. Microbiol. 18, 209-216.
14. Tucker, K., Plosila, L., and Samuel, J. (1994) Correlation between hemagglutination and globotetraosyl-ceramide binding by *Branhamella catarrhalis*. Abstract 117 of the 94th General meeting of the American Society for Microbiology.
15. Lunde E, Munthe L A, Vabo A, Sandlie I, Bogen B. (1999) Antibodies engineered with IgD specificity efficiently deliver integrated, T-cell epitopes for antigen presentation by B cells. Nat Biotechnol. 17, 670-675.
16. Lycke N. (2001) The B-cell targeted CTA1-DD vaccine adjuvant is highly effective at enhancing anti-body as well as CTL responses. Curr. Opin. Mol. Ther. 3, 37-44.
17. Ito O, Harada M, Takenoyama M, Tamada K, Li T, Abe K, Fujie H, Nomoto K.
1998 Vaccination with activated B cells pulsed with tumor-lysates can induce tumor-specific CD4+ T cells in vivo. Immunobiol. 199, 133-147.

The invention claimed is:

1. An isolated IgD-binding fragment of a surface exposed protein, wherein:
   said surface exposed protein comprises the amino acid sequence of SEQ ID NO:1, and
   said isolated IgD-binding fragment selectively binds membrane bound or soluble IgD.

2. The isolated IgD-binding fragment of claim 1, wherein said isolated IgD-binding fragment comprises the amino acid sequence of SEQ ID NO:10.

3. The isolated IgD-binding fragment of claim 1, wherein said isolated IgD-binding fragment further selectively binds erythrocytes and epithelial cells.

4. A vaccine comprising an isolated surface exposed protein, wherein said surface exposed protein:
   comprises the amino acid sequence of SEQ ID NO:1;
   has an apparent molecular weight of 200 kDa; and
   selectively binds membrane bound or soluble IgD.

5. A vaccine comprising the IgD-binding fragment of claim 1.

6. A vaccine comprising the IgD-binding fragment of claim 2.

7. A vaccine comprising the IgD-binding fragment of claim 3.

8. A composition comprising the vaccine of any one of claims 4-7 combined with another vaccine.

9. A composition comprising the vaccine of any one of claims 4-7 combined with an immunogenic portion of another molecule.

10. An isolated fusion protein or polypeptide comprising the IgD-binding fragment of claim 1 combined with another protein.

11. An isolated fusion protein or polypeptide comprising the IgD-binding fragment of claim 2 combined with another protein.

12. An isolated fusion protein or polypeptide comprising the IgD-binding fragment of claim 3 combined with another protein.

13. An isolated fusion protein or polypeptide comprising an amino acid sequence comprising SEQ ID NO:1 combined with another protein.

14. An isolated fusion product comprising the IgD-binding fragment of claim 1 bound to a protein, carbohydrate or matrix.

15. An isolated fusion product comprising the IgD-binding fragment of claim 2 bound to a protein, carbohydrate or matrix.

16. An isolated fusion product comprising the IgD-binding fragment of claim 3 bound to a protein, carbohydrate or matrix.

17. An isolated fusion product comprising an amino acid sequence comprising SEQ ID NO:1 bound to a protein, carbohydrate or matrix.

* * * * *

SEQUENCE LISTING

```
<160> NUMBER OF SEQ ID NOS: 16

<210> SEQ ID NO 1
<211> LENGTH: 2139
<212> TYPE: PRT
<213> ORGANISM: Moraxella catarrhalis

<400> SEQUENCE: 1

Met Asn His Ile Tyr Lys Val Ile Phe Asn Lys Ala Thr Gly Thr Phe
 1               5                  10                  15

Met Ala Val Ala Glu Tyr Ala Lys Ser His Ser Thr Gly Gly Ser Cys
            20                  25                  30

Ala Thr Gly Gln Val Gly Ser Val Cys Thr Leu Ser Phe Ala Arg Val
        35                  40                  45

Ala Ala Leu Ala Val Leu Val Ile Gly Ala Thr Leu Asn Gly Ser Ala
    50                  55                  60

Tyr Ala Gln Gln Asp Pro Arg His Ile Ala Ile Asp Gly Asn Ser Ser
65                  70                  75                  80

Asn Thr Ser Ser Gly Thr Ala Arg Ala Thr Gly Asp Arg Ala Ile Ala
                85                  90                  95

Leu Gly Glu Asn Ala Asn Ala Glu Gly Gly Gln Ala Ile Ala Ile Gly
            100                 105                 110

Ser Ser Asn Lys Thr Gly Gly Arg Asn Ala Leu Asn Ile Gly Thr Asp
        115                 120                 125

Ala Lys Gly Glu Glu Ser Ile Ala Ile Gly Gly Asp Val Val Ala Glu
    130                 135                 140

Gly Thr Ala Ser Ile Ala Ile Gly Gly Asp Asp Leu His Leu Trp Asp
```

```
                145                 150                 155                 160
Glu Pro Asn Lys Gln Lys Phe Leu Asp Pro Lys Val Lys Glu Leu Ile
                165                 170                 175

Leu Lys His Gln Glu Leu Asn Asn Ile Tyr Lys Leu Pro Asp Gly Ser
            180                 185                 190

Pro Gln Arg Tyr Phe Arg Thr Tyr Ala Lys Gly His Ala Ser Ile Ala
        195                 200                 205

Leu Gly Thr Met Thr Gln Ala Glu Gly His Phe Ala Asn Ala Phe Gly
    210                 215                 220

Thr Arg Ala Thr Ala Lys Gly Asn Tyr Ser Leu Ala Val Gly Leu Thr
225                 230                 235                 240

Ala Gln Ala Asn Thr Glu Ser Ser Ile Ala Val Gly Ser Asn Ala Gln
                245                 250                 255

Ala Asn Gly Phe Ala Ala Thr Ala Ile Gly Gly Thr Lys Ala Asp
                260                 265                 270

Leu Gly Arg Ser Ile Ala Leu Gly Phe Gly Ser Gln Ile Leu Thr Lys
            275                 280                 285

Glu Lys Asp Ser His Asn Asn Thr Asn Val Tyr Val Pro Gln Gly Glu
        290                 295                 300

Ile Leu Glu Glu Arg Tyr Lys Ala Thr Glu Asn Gly Gln Ser Pro Asn
305                 310                 315                 320

Lys Val Val Asp Ile Phe Ser Ile Gly Ser Ser Ile Lys Arg Lys
                325                 330                 335

Ile Ile Asn Val Gly Ala Gly Ser Gln Glu Thr Asp Ala Val Asn Val
                340                 345                 350

Ala Gln Leu Lys Leu Val Glu Arg Val Ala Lys Arg Gln Ile Thr Phe
            355                 360                 365

Gln Gly Asp Asp Ser Asn Asn Ser Val Lys Lys Gly Leu Gly Gln Thr
        370                 375                 380

Leu Thr Ile Lys Gly Gly Lys Thr Glu Thr Gly Glu Leu Thr Glu Asn
385                 390                 395                 400

Asn Ile Gly Val Val Gln Asp Asp Asn Gly Asn Gly Leu Lys Val Lys
                405                 410                 415

Leu Ala Lys Asp Leu Thr Gly Leu Thr Lys Val Ala Val Asn Gly Asn
            420                 425                 430

Gly Ala Asn Asn Ala Glu Leu Leu Asn Gly Gly Leu Thr Phe Ser Thr
        435                 440                 445

Ser Gly Ala Asn Ala Gly Lys Thr Val Tyr Gly Thr Asp Gly Val Lys
    450                 455                 460

Phe Thr Asn Asn Thr Gly Thr Gly Thr Gly Thr Ala Ile Pro Asp Thr
465                 470                 475                 480

Thr Arg Ile Thr Lys Asn Lys Ile Gly Phe Ala Gly Ala Asp Glu Gln
                485                 490                 495

Val Asp Glu Ser Lys Pro Tyr Leu Asp Asn Glu Lys Leu Lys Val Gly
            500                 505                 510

Thr Val Glu Ile Lys Lys Thr Gly Ile Asn Ala Gly Asn Gln Glu Ile
        515                 520                 525

Thr Lys Val Lys Ser Ala Ile Val Asp Ala Val Asn Gly Gln Ala Asn
    530                 535                 540

Gln Ser Phe Val Asn Leu Leu Glu Thr Ala Gly Thr Asn Thr Asn Lys
545                 550                 555                 560

Gln Asn Ser Ala Ala Thr Val Lys Asp Leu Tyr Asp Leu Ser Gln Ser
                565                 570                 575
```

```
Pro Leu Thr Phe Thr Gly Asp Ser Gly Asn Val Lys Arg Lys Leu Gly
            580                 585                 590

Gln Thr Leu Thr Ile Thr Gly Gly Gln Thr Lys Thr Asp Gln Leu Thr
        595                 600                 605

Asp Asn Asn Ile Gly Val Val Ala Gly Thr Asn Gly Leu Thr Val Lys
    610                 615                 620

Leu Ala Lys Thr Leu Asn Ser Leu Thr Glu Val Asn Thr Ala Thr Leu
625                 630                 635                 640

Asn Ala Thr Asn Lys Val Lys Val Asp Asn Ser Thr Gly Asn Thr Ala
                645                 650                 655

Glu Leu Leu Asn Asn Gly Leu Thr Phe Thr Gln Thr Thr Gly Ala Asn
            660                 665                 670

Ser Gly Lys Thr Val Tyr Gly Asn Asp Gly Leu Lys Phe Thr Asn Ser
        675                 680                 685

Ala Asn Lys Ala Leu Gly Gly Thr Thr Tyr Ile Thr Lys Asp Gln Val
    690                 695                 700

Gly Phe Ser Asn Gln Asp Gly Leu Leu Asp Glu Ser Lys Pro Tyr Leu
705                 710                 715                 720

Asn Arg Glu Lys Leu Lys Val Gly Lys Ile Glu Ile Lys Asp Ser Gly
                725                 730                 735

Ile Asn Ala Gly Gly Lys Ala Ile Thr Gly Leu Pro Ser Thr Leu Pro
            740                 745                 750

Asn Thr Thr Tyr Thr Ala Pro Gly Val His Thr Ala Leu His Gly Ser
        755                 760                 765

Thr Ile Ser Asn Asp Asp Lys Thr Arg Ala Ala Ser Ile Ala Asp Val
    770                 775                 780

Leu Asn Ala Gly Phe Asn Leu Glu Gly Asn Gly Glu Ala Val Asp Phe
785                 790                 795                 800

Val Ser Thr Tyr Asp Thr Val Asn Phe Ala Asp Gly Asn Ala Thr Thr
                805                 810                 815

Ala Lys Val Thr Tyr Asp Asn Lys Thr Ser Lys Val Ala Tyr Asp Val
            820                 825                 830

Asn Val Asp Gly Thr Thr Ile His Leu Thr Gly Thr Asn Gly Lys Lys
        835                 840                 845

Asn Gln Ile Gly Val Lys Thr Thr Thr Leu Thr Thr Lys Arg Ala Lys
    850                 855                 860

Gly Asn Thr Ala Thr Asn Phe Ser Val Asn Ser Gly Asp Asp Asn Ala
865                 870                 875                 880

Leu Ile Asn Ala Lys Asp Ile Ala Asp Asn Leu Asn Thr Leu Ala Gly
                885                 890                 895

Glu Ile Arg Thr Ala Lys Gly Thr Ala Ser Thr Ala Leu Gln Thr Phe
            900                 905                 910

Ser Ile Ile Asp Glu Gln Gly Asn Asn Phe Met Val Gly Asn Leu Tyr
        915                 920                 925

Ser Gly Tyr Asp Thr Ser Asn Thr Ser Glu Thr Val Thr Phe Val Gly
    930                 935                 940

Glu Asn Gly Ile Thr Thr Lys Val Asn Lys Gly Lys Val Lys Val Gly
945                 950                 955                 960

Ile Asp Gln Thr Lys Gly Leu Thr Pro Lys Leu Thr Val Gly Ser
                965                 970                 975

Ser Asn Gly Lys Gly Ile Val Ile Asp Ser Lys Asp Gly Gln Asn Thr
            980                 985                 990

Ile Thr Gly Leu Ser Asn Thr Leu Thr Asp Ala Thr Asn Ala Thr Thr
        995                 1000                1005
```

```
Gly His Val Ser Glu Ile Gln Gly Leu Ala Gln Gly Ala Asn Lys Thr
    1010                1015                1020

Arg Ala Ala Ser Ile Gly Asp Val Leu Asn Ala Gly Phe Asn Leu Gln
1025                1030                1035                1040

Gly Asn Gly Glu Ala Lys Asp Phe Val Ser Thr Tyr Asp Thr Val Asn
        1045                1050                1055

Phe Ile Asp Gly Asn Ala Thr Thr Ala Lys Val Thr Tyr Asp Asp Thr
        1060                1065                1070

Lys Gln Thr Ser Thr Val Thr Tyr Asp Val Asn Val Asp Asn Lys Thr
        1075                1080                1085

Leu Glu Val Thr Gly Asp Lys Lys Leu Gly Val Lys Thr Thr Thr Leu
    1090                1095                1100

Thr Lys Thr Ser Ala Asn Gly Asn Ala Thr Lys Phe Ser Ala Ala Asp
1105                1110                1115                1120

Gly Asp Ala Leu Val Lys Ala Ser Asp Ile Ala Thr His Leu Asn Thr
        1125                1130                1135

Leu Ala Gly Asp Ile Gln Thr Ala Lys Gly Ala Ser Gln Ala Ser Ser
        1140                1145                1150

Ser Ala Ser Tyr Val Asp Ala Asp Gly Asn Lys Val Ile Tyr Asp Ser
        1155                1160                1165

Thr Asp Lys Lys Tyr Tyr Gln Ala Lys Asn Asp Gly Thr Val Asp Lys
    1170                1175                1180

Thr Lys Glu Val Ala Lys Asp Lys Leu Val Ala Gln Ala Gln Thr Pro
1185                1190                1195                1200

Asp Gly Thr Leu Ala Arg Met Asn Val Lys Ser Val Ile Asn Lys Glu
        1205                1210                1215

Gln Val Asn Asp Ala Asn Lys Lys Gln Gly Ile Asn Glu Asp Asn Ala
        1220                1225                1230

Phe Val Lys Gly Leu Glu Lys Ala Ala Ser Asp Asn Lys Thr Lys Asn
    1235                1240                1245

Ala Ala Val Thr Val Gly Asp Leu Asn Ala Val Ala Gln Thr Pro Leu
    1250                1255                1260

Thr Phe Ala Gly Asp Thr Gly Thr Thr Ala Lys Lys Leu Gly Glu Thr
1265                1270                1275                1280

Leu Thr Ile Lys Gly Gly Gln Thr Asp Thr Asn Lys Leu Thr Asp Asn
        1285                1290                1295

Asn Ile Gly Val Val Ala Gly Thr Asp Gly Phe Thr Val Lys Leu Ala
        1300                1305                1310

Lys Asp Leu Thr Asn Leu Asn Ser Val Asn Ala Gly Gly Thr Lys Ile
    1315                1320                1325

Asp Asp Lys Gly Val Ser Phe Val Asp Ala Asn Gly Gln Ala Lys Ala
    1330                1335                1340

Asn Thr Pro Val Leu Ser Ala Asn Gly Leu Asp Leu Gly Gly Lys Arg
1345                1350                1355                1360

Ile Ser Asn Ile Gly Ala Ala Val Asp Asp Asn Asp Ala Val Asn Phe
        1365                1370                1375

Lys Gln Phe Asn Glu Val Ala Lys Thr Val Asn Asn Leu Asn Asn Gln
        1380                1385                1390

Ser Asn Ser Gly Ala Ser Leu Pro Phe Val Val Thr Asp Ala Asn Gly
        1395                1400                1405

Lys Pro Ile Asn Gly Thr Asp Asp Lys Pro Gln Lys Ala Ile Lys Gly
    1410                1415                1420

Ala Asp Gly Lys Tyr Tyr His Ala Asn Ala Asn Gly Val Pro Val Asp
```

```
1425                1430                1435                1440

Lys Asp Gly Asn Pro Ile Thr Asp Ala Asp Lys Leu Ala Asn Leu Ala
                1445                1450                1455

Ala His Gly Lys Pro Leu Asp Ala Gly His Gln Val Val Ala Ser Leu
            1460                1465                1470

Gly Gly Asn Ser Asp Ala Ile Thr Leu Thr Asn Ile Lys Ser Thr Leu
        1475                1480                1485

Pro Gln Ile Asp Thr Pro Asn Thr Gly Asn Ala Asn Ala Gly Gln Ala
    1490                1495                1500

Gln Ser Leu Pro Ser Leu Ser Ala Ala Gln Gln Ser Asn Ala Ala Ser
1505                1510                1515                1520

Val Lys Asp Val Leu Asn Val Gly Phe Asn Leu Gln Thr Asn His Asn
                1525                1530                1535

Gln Val Asp Phe Val Lys Ala Tyr Asp Thr Val Asn Phe Val Asn Gly
            1540                1545                1550

Thr Gly Ala Asp Ile Thr Ser Val Arg Ser Ala Asp Gly Thr Met Ser
        1555                1560                1565

Asn Ile Thr Val Asn Thr Ala Leu Ala Ala Thr Asp Asp Gly Asn
    1570                1575                1580

Val Leu Ile Lys Ala Lys Asp Gly Lys Phe Tyr Lys Ala Asp Asp Leu
1585                1590                1595                1600

Met Pro Asn Gly Ser Leu Lys Ala Gly Lys Ser Ala Ser Asp Ala Lys
                1605                1610                1615

Thr Pro Thr Gly Leu Ser Leu Val Asn Pro Asn Ala Gly Lys Gly Ser
            1620                1625                1630

Thr Gly Asp Ala Val Ala Leu Asn Asn Leu Ser Lys Ala Val Phe Lys
        1635                1640                1645

Ser Lys Asp Gly Thr Thr Thr Thr Val Ser Ser Asp Gly Ile Ser
    1650                1655                1660

Ile Gln Gly Lys Asp Asn Ser Asn Ile Thr Leu Ser Lys Asp Gly Leu
1665                1670                1675                1680

Asn Val Gly Gly Lys Val Ile Ser Asn Val Gly Lys Gly Thr Lys Asp
                1685                1690                1695

Thr Asp Ala Ala Asn Val Gln Gln Leu Asn Arg Ser Thr Gln Leu Val
            1700                1705                1710

Gly Ser Trp Val Met Ala Gly Asn Asp Asn Ala Asp Gly Asn Gln Val
        1715                1720                1725

Asn Ile Ala Asp Ile Lys Lys Asp Pro Asn Ser Gly Ser Ser Ser Asn
    1730                1735                1740

Arg Thr Val Ile Lys Ala Gly Thr Val Leu Gly Gly Lys Gly Asn Asn
1745                1750                1755                1760

Asp Thr Glu Lys Leu Ala Thr Gly Gly Val Gln Val Gly Val Asp Lys
                1765                1770                1775

Asp Gly Asn Ala Asn Gly Asp Leu Ser Asn Val Trp Val Lys Thr Gln
            1780                1785                1790

Lys Asp Gly Ser Lys Lys Ala Leu Leu Ala Thr Tyr Asn Ala Ala Gly
        1795                1800                1805

Gln Thr Asn Tyr Leu Thr Asn Asn Pro Ala Glu Ala Ile Asp Arg Ile
    1810                1815                1820

Asn Glu Gln Gly Ile Arg Phe Phe His Val Asn Asp Gly Asn Gln Glu
1825                1830                1835                1840

Pro Val Val Gln Gly Arg Asn Gly Ile Asp Ser Ser Ala Ser Gly Lys
                1845                1850                1855
```

-continued

His Ser Val Ala Val Gly Tyr Lys Ala Lys Ala Asp Gly Glu Ala Ala
        1860                1865                1870

Val Ala Ile Gly Arg Gln Thr Gln Ala Gly Asn Gln Ser Ile Ala Ile
    1875                1880                1885

Gly Asp Asn Ala Gln Ala Thr Gly Asp Gln Ser Ile Ala Ile Gly Thr
1890                1895                1900

Gly Asn Val Val Ala Gly Lys His Ser Gly Ala Ile Gly Asp Pro Ser
1905                1910                1915                1920

Thr Val Lys Ala Asp Asn Ser Tyr Ser Val Gly Asn Asn Gln Phe
            1925                1930                1935

Thr Asp Ala Thr Gln Thr Asp Val Phe Gly Val Gly Asn Asn Ile Thr
        1940                1945                1950

Val Thr Glu Ser Asn Ser Val Ala Leu Gly Ser Asn Ser Ala Ile Ser
    1955                1960                1965

Ala Gly Thr His Ala Gly Thr Gln Ala Lys Lys Ser Asp Gly Thr Ala
    1970                1975                1980

Gly Thr Thr Thr Thr Ala Gly Ala Thr Gly Thr Val Lys Gly Phe Ala
1985                1990                1995                2000

Gly Gln Thr Ala Val Gly Ala Val Ser Val Gly Ala Ser Gly Ala Glu
        2005                2010                2015

Arg Arg Ile Gln Asn Val Ala Ala Gly Glu Val Ser Ala Thr Ser Thr
        2020                2025                2030

Asp Ala Val Asn Gly Ser Gln Leu Tyr Lys Ala Thr Gln Ser Ile Ala
        2035                2040                2045

Asn Ala Thr Asn Glu Leu Asp His Arg Ile His Gln Asn Glu Asn Lys
    2050                2055                2060

Ala Asn Ala Gly Ile Ser Ser Ala Met Ala Met Ala Ser Met Pro Gln
2065                2070                2075                2080

Ala Tyr Ile Pro Gly Arg Ser Met Val Thr Gly Gly Ile Ala Thr His
            2085                2090                2095

Asn Gly Gln Gly Ala Val Ala Val Gly Leu Ser Lys Leu Ser Asp Asn
        2100                2105                2110

Gly Gln Trp Val Phe Lys Ile Asn Gly Ser Ala Asp Thr Gln Gly His
    2115                2120                2125

Val Gly Ala Ala Val Gly Ala Gly Phe His Phe
    2130                2135

<210> SEQ ID NO 2
<211> LENGTH: 6889
<212> TYPE: DNA
<213> ORGANISM: Moraxella catarrhalis
<220> FEATURE:
<221> NAME/KEY: CDS
<222> LOCATION: (356)..(6772)

<400> SEQUENCE: 2

```
aatcattacc cccccttta  tgggggatca tatgaataga atattatgat tgtatctgat      60
tattgtatca gaatggtgat gcctacgagt tgatttgggt gaatcactct attatttgat    120
atgttttgaa actaatctat tgacttaaat caccatatgg ttataattta gcataatggt    180 aggcttttg  taaaaatcac atcgcaatat tgttctactg ttactaccat gcttgaatga    240
cgatcccaat catcagattc attcaagtga tgtgtttgta tacgcatcat ttaccctaat    300
tatttcaatc gaaatgccta tgtcagcatg tatcattttt ttaaggtaaa ccacc atg    358
                                                              Met
                                                                1 aat cac atc tat aaa gtc atc ttt aac aaa gcc aca ggc aca ttt atg      406
```

```
                                                           -continued
Asn His Ile Tyr Lys Val Ile Phe Asn Lys Ala Thr Gly Thr Phe Met
          5                  10                 15 gcc gtg gcg gaa tat gcc aaa tcc cac agc acg ggg ggt agc tgt gct      454
Ala Val Ala Glu Tyr Ala Lys Ser His Ser Thr Gly Gly Ser Cys Ala
         20                  25                 30 aca ggg caa gtt ggc agt gta tgc act ctg agc ttt gcc cgt gtt gcc      502
Thr Gly Gln Val Gly Ser Val Cys Thr Leu Ser Phe Ala Arg Val Ala
 35                  40                  45 gcg ctc gct gtc ctc gtg atc ggt gcg acg ctc aat ggc agt gct tat      550
Ala Leu Ala Val Leu Val Ile Gly Ala Thr Leu Asn Gly Ser Ala Tyr
 50                  55                  60                  65 gct caa caa gat ccc aga cat atc gca att gat ggc aac agc tcg aac      598
Ala Gln Gln Asp Pro Arg His Ile Ala Ile Asp Gly Asn Ser Ser Asn
             70                  75                  80 aca tcc tca ggc act gcc cgt gcg aca ggt gat cga gcc att gct ctt      646
Thr Ser Ser Gly Thr Ala Arg Ala Thr Gly Asp Arg Ala Ile Ala Leu
             85                  90                  95 ggt gaa aat gct aat gca gag ggc ggt caa gcc atc gcc atc ggt agt      694
Gly Glu Asn Ala Asn Ala Glu Gly Gly Gln Ala Ile Ala Ile Gly Ser
            100                 105                 110 agc aat aaa aca ggt ggt aga aac gcg ctg aat ata ggt acc gat gcc      742
Ser Asn Lys Thr Gly Gly Arg Asn Ala Leu Asn Ile Gly Thr Asp Ala
        115                 120                 125 aaa ggt gag gag tcc atc gcc atc ggt ggt gat gta gtg gct gag ggt      790
Lys Gly Glu Glu Ser Ile Ala Ile Gly Gly Asp Val Val Ala Glu Gly
130                 135                 140                 145 act gcc tcg att gcc atc ggt ggt gat gac tta cat ttg tgg gat gaa      838
Thr Ala Ser Ile Ala Ile Gly Gly Asp Asp Leu His Leu Trp Asp Glu
                150                 155                 160 cca aat aag caa aag ttc ctc gac cca aaa gtt aaa gaa ttg att tta      886
Pro Asn Lys Gln Lys Phe Leu Asp Pro Lys Val Lys Glu Leu Ile Leu
            165                 170                 175 aaa cat caa gaa tta aac aac ata tac aaa ctg cct gat ggt agt cct      934
Lys His Gln Glu Leu Asn Asn Ile Tyr Lys Leu Pro Asp Gly Ser Pro
        180                 185                 190 caa aga tat ttt cgc aca tac gca aag gga cac gcc agt att gca cta      982
Gln Arg Tyr Phe Arg Thr Tyr Ala Lys Gly His Ala Ser Ile Ala Leu
    195                 200                 205 gga acc atg aca cag gca gag ggt cat ttt gcc aac gcc ttt ggt aca     1030
Gly Thr Met Thr Gln Ala Glu Gly His Phe Ala Asn Ala Phe Gly Thr
210                 215                 220                 225 cgg gca aca gct aaa ggc aac tat tcc ttg gca gtg ggt ctt acc gcc     1078
Arg Ala Thr Ala Lys Gly Asn Tyr Ser Leu Ala Val Gly Leu Thr Ala
                230                 235                 240 caa gcc aac aca gaa tct tca atc gct gtt ggt tct aat gca caa gct     1126
Gln Ala Asn Thr Glu Ser Ser Ile Ala Val Gly Ser Asn Ala Gln Ala
            245                 250                 255 aac ggg ttt gca gcg aca gcc att ggt gga ggt act aaa gct gat ttg     1174
Asn Gly Phe Ala Ala Thr Ala Ile Gly Gly Gly Thr Lys Ala Asp Leu
        260                 265                 270 ggt cga agc ata gcc cta ggt ttt ggt tct cag atc ctt act aag gag     1222
Gly Arg Ser Ile Ala Leu Gly Phe Gly Ser Gln Ile Leu Thr Lys Glu
    275                 280                 285 aag gat agt cat aac aat acc aat gtc tat gta cca caa ggt gaa ata     1270
Lys Asp Ser His Asn Asn Thr Asn Val Tyr Val Pro Gln Gly Glu Ile
290                 295                 300                 305 tta gaa gag cgg tat aaa gcc acc gaa aac ggt cag tcg cct aat aag     1318
Leu Glu Glu Arg Tyr Lys Ala Thr Glu Asn Gly Gln Ser Pro Asn Lys
                310                 315                 320 gta gtg gat ata ttt tcc att ggt agt agc tct atc aaa cgt aaa atc     1366
```

```
Val Val Asp Ile Phe Ser Ile Gly Ser Ser Ile Lys Arg Lys Ile
            325                 330                 335 atc aat gtc ggt gcg ggt tct cag gag acc gat gcg gtc aat gtg gca    1414
Ile Asn Val Gly Ala Gly Ser Gln Glu Thr Asp Ala Val Asn Val Ala
            340                 345                 350 cag ctt aaa ttg gtg gag cgg gtg gct aag cgt caa att act ttt cag    1462
Gln Leu Lys Leu Val Glu Arg Val Ala Lys Arg Gln Ile Thr Phe Gln
        355                 360                 365 ggt gat gat agc aat aat agc gta aaa aaa ggt ttg ggt cag act tta    1510
Gly Asp Asp Ser Asn Asn Ser Val Lys Lys Gly Leu Gly Gln Thr Leu
370                 375                 380                 385 act att aaa ggt ggt aaa aca gag acc ggt gaa cta acc gaa aat aac    1558
Thr Ile Lys Gly Gly Lys Thr Glu Thr Gly Glu Leu Thr Glu Asn Asn
            390                 395                 400 atc ggt gtg gta caa gat gat aat ggt aat ggc tga aaa gtt aaa ctt    1606
Ile Gly Val Val Gln Asp Asp Asn Gly Asn Gly Leu Lys Val Lys Leu
            405                 410                 415 gct aaa gat ctg act ggt ttg acc aag gtt gca gta aat ggt aat ggt    1654
Ala Lys Asp Leu Thr Gly Leu Thr Lys Val Ala Val Asn Gly Asn Gly
            420                 425                 430 gct aac aac gcc gag cta cta aac ggt ggt ctg acc ttt tcg aca tca    1702
Ala Asn Asn Ala Glu Leu Leu Asn Gly Gly Leu Thr Phe Ser Thr Ser
        435                 440                 445 ggt gcc aat gca ggc aaa acg gtc tat ggc act gat ggg gtg aag ttt    1750
Gly Ala Asn Ala Gly Lys Thr Val Tyr Gly Thr Asp Gly Val Lys Phe
450                 455                 460                 465 act aat aat aca gga aca gga aca gga acg gca ata ccc gac act act    1798
Thr Asn Asn Thr Gly Thr Gly Thr Gly Thr Ala Ile Pro Asp Thr Thr
            470                 475                 480 cgt att acc aaa aat aaa att ggc ttt gct ggg gct gat gaa caa gtt    1846
Arg Ile Thr Lys Asn Lys Ile Gly Phe Ala Gly Ala Asp Glu Gln Val
            485                 490                 495 gat gaa agc aaa cct tat ctt gac aac gaa aag cta aaa gtt ggc aca    1894
Asp Glu Ser Lys Pro Tyr Leu Asp Asn Glu Lys Leu Lys Val Gly Thr
        500                 505                 510 gtt gag att aaa aaa act ggc atc aat gca ggt aat caa gaa att acc    1942
Val Glu Ile Lys Lys Thr Gly Ile Asn Ala Gly Asn Gln Glu Ile Thr
        515                 520                 525 aag gtc aaa tct gcc att gtt gat gca gtt aat gga caa gca aat caa    1990
Lys Val Lys Ser Ala Ile Val Asp Ala Val Asn Gly Gln Ala Asn Gln
530                 535                 540                 545 agc ttt gtg aac ctt cta gaa aca gca ggc aca aac acc aac aaa caa    2038
Ser Phe Val Asn Leu Leu Glu Thr Ala Gly Thr Asn Thr Asn Lys Gln
            550                 555                 560 aac tct gcc gcc acg gtt aaa gac tta tac gac cta tca caa tca ccg    2086
Asn Ser Ala Ala Thr Val Lys Asp Leu Tyr Asp Leu Ser Gln Ser Pro
        565                 570                 575 ctg acc ttt aca ggt gat agc ggt aac gtt aag aga aaa ctg ggt cag    2134
Leu Thr Phe Thr Gly Asp Ser Gly Asn Val Lys Arg Lys Leu Gly Gln
        580                 585                 590 act tta acc atc aca ggc gga caa aca aag acc gat caa tta acc gac    2182
Thr Leu Thr Ile Thr Gly Gly Gln Thr Lys Thr Asp Gln Leu Thr Asp
        595                 600                 605 aat aac atc ggt gtg gta gca ggt act aat ggc tta acc gtt aaa ctt    2230
Asn Asn Ile Gly Val Val Ala Gly Thr Asn Gly Leu Thr Val Lys Leu
610                 615                 620                 625 gct aaa act tta aac agt ctt act gaa gtt aat acg gct aca tta aac    2278
Ala Lys Thr Leu Asn Ser Leu Thr Glu Val Asn Thr Ala Thr Leu Asn
            630                 635                 640 gcc acc aat aaa gtt aag gta gat aat agt act ggt aat acg gct gaa    2326
```

-continued

```
Ala Thr Asn Lys Val Lys Val Asp Asn Ser Thr Gly Asn Thr Ala Glu
            645             650             655 tta tta aac aat ggt tta acc ttt acc caa aca aca ggt gca aat tca    2374
Leu Leu Asn Asn Gly Leu Thr Phe Thr Gln Thr Thr Gly Ala Asn Ser
            660             665             670 ggt aaa acc gtc tat ggc aat gat ggc ttg aag ttt act aat agt gct    2422
Gly Lys Thr Val Tyr Gly Asn Asp Gly Leu Lys Phe Thr Asn Ser Ala
    675             680             685 aat aaa gca ctt ggc ggc aca act tac atc acc aaa gat caa gtt ggt    2470
Asn Lys Ala Leu Gly Gly Thr Thr Tyr Ile Thr Lys Asp Gln Val Gly
690             695             700             705 ttt agc aat caa gat ggc tta ctt gat gaa agc aaa ccg tat ctt aac    2518
Phe Ser Asn Gln Asp Gly Leu Leu Asp Glu Ser Lys Pro Tyr Leu Asn
            710             715             720 cga gaa aag cta aaa gtt ggt aaa att gag att aaa gac agt ggc att    2566
Arg Glu Lys Leu Lys Val Gly Lys Ile Glu Ile Lys Asp Ser Gly Ile
            725             730             735 aat gca ggt ggt aaa gcc atc aca gga ctg ccc tca aca ctg ccc aac    2614
Asn Ala Gly Gly Lys Ala Ile Thr Gly Leu Pro Ser Thr Leu Pro Asn
            740             745             750 act acc tat act gca cct ggc gtg cat act gca cta cat ggc agt aca    2662
Thr Thr Tyr Thr Ala Pro Gly Val His Thr Ala Leu His Gly Ser Thr
755             760             765 att tct aac gac gac aaa acc cgt gcc gcc agt atc gcc gat gtg cta    2710
Ile Ser Asn Asp Asp Lys Thr Arg Ala Ala Ser Ile Ala Asp Val Leu
770             775             780             785 aac gca ggc ttt aac ttg gaa ggt aat ggt gaa gcg gtt gac ttt gtc    2758
Asn Ala Gly Phe Asn Leu Glu Gly Asn Gly Glu Ala Val Asp Phe Val
            790             795             800 tcc act tat gac acc gtc aac ttt gcc gat ggc aat gcc acc acc gct    2806
Ser Thr Tyr Asp Thr Val Asn Phe Ala Asp Gly Asn Ala Thr Thr Ala
    805             810             815 aag gta act tat gat aac aaa acc agt aaa gtg gcg tat gat gtc aat    2854
Lys Val Thr Tyr Asp Asn Lys Thr Ser Lys Val Ala Tyr Asp Val Asn
            820             825             830 gtg gat ggt aca acc att cat cta aca ggc act aat ggc aag aaa aac    2902
Val Asp Gly Thr Thr Ile His Leu Thr Gly Thr Asn Gly Lys Lys Asn
835             840             845 caa att ggc gta aaa acc acc aca ctg acc aca aaa cgt gct aaa ggt    2950
Gln Ile Gly Val Lys Thr Thr Thr Leu Thr Thr Lys Arg Ala Lys Gly
850             855             860             865 aat aca gca act aat ttt agt gtt aac tct ggt gat gac aat gcc ctt    2998
Asn Thr Ala Thr Asn Phe Ser Val Asn Ser Gly Asp Asp Asn Ala Leu
            870             875             880 att aac gcc aaa gac atc gcc gac aat cta aac acc cta gct ggt gaa    3046
Ile Asn Ala Lys Asp Ile Ala Asp Asn Leu Asn Thr Leu Ala Gly Glu
            885             890             895 att cgc acc gcc aaa ggc aca gca agc acc gcc cta caa acc ttc tct    3094
Ile Arg Thr Ala Lys Gly Thr Ala Ser Thr Ala Leu Gln Thr Phe Ser
    900             905             910 att att gat gaa caa ggt aat aac ttt atg gtc ggt aac ctt tac tct    3142
Ile Ile Asp Glu Gln Gly Asn Asn Phe Met Val Gly Asn Leu Tyr Ser
915             920             925 ggt tat gac acc tca aat acc tct gag acc gtc acc ttt gta ggt gaa    3190
Gly Tyr Asp Thr Ser Asn Thr Ser Glu Thr Val Thr Phe Val Gly Glu
930             935             940             945 aac ggc att acc acc aag gta aat aaa ggt aaa gtc aaa gtt ggt att    3238
Asn Gly Ile Thr Thr Lys Val Asn Lys Gly Lys Val Lys Val Gly Ile
            950             955             960 gac caa acc aaa ggc tta acc acg cct aag ctg acc gtg ggt agt agt    3286
```

```
            Asp Gln Thr Lys Gly Leu Thr Thr Pro Lys Leu Thr Val Gly Ser Ser
                        965                 970                 975 aat ggc aaa ggc att gtc att gac agt aaa gat ggt caa aat acc atc           3334
Asn Gly Lys Gly Ile Val Ile Asp Ser Lys Asp Gly Gln Asn Thr Ile
            980                 985                 990 aca gga cta agc aac act cta acc gat gcc acc aac gca aca aca ggg           3382
Thr Gly Leu Ser Asn Thr Leu Thr Asp Ala Thr Asn Ala Thr Thr Gly
        995                 1000                1005 cat gtc agt gaa atc cag ggc ttg gca caa ggt gca aac aaa acc cgt           3430
His Val Ser Glu Ile Gln Gly Leu Ala Gln Gly Ala Asn Lys Thr Arg
1010                1015                1020                1025 gcc gcc agc att ggt gat gta cta aac gca ggc ttt aac ttg caa ggc           3478
Ala Ala Ser Ile Gly Asp Val Leu Asn Ala Gly Phe Asn Leu Gln Gly
                1030                1035                1040 aat ggt gaa gcc aaa gac ttt gtc tcc act tat gac acc gtc aac ttt           3526
Asn Gly Glu Ala Lys Asp Phe Val Ser Thr Tyr Asp Thr Val Asn Phe
            1045                1050                1055 atc gat ggc aat gcc acc acc gct aag gtg acc tat gat gac acg aaa           3574
Ile Asp Gly Asn Ala Thr Thr Ala Lys Val Thr Tyr Asp Asp Thr Lys
        1060                1065                1070 cag acc agc aca gta act tat gat gtc aat gtg gat aat aaa acc ctt           3622
Gln Thr Ser Thr Val Thr Tyr Asp Val Asn Val Asp Asn Lys Thr Leu
    1075                1080                1085 gaa gtg aca ggc gat aaa aaa ctt ggc gtc aaa acc acc aca ctg acc           3670
Glu Val Thr Gly Asp Lys Lys Leu Gly Val Lys Thr Thr Thr Leu Thr
1090                1095                1100                1105 aaa aca agt gct aat ggt aat gca acc aaa ttt agt gcc gcc gat ggc           3718
Lys Thr Ser Ala Asn Gly Asn Ala Thr Lys Phe Ser Ala Ala Asp Gly
                1110                1115                1120 gat gcc ctt gtt aaa gcc agt gat atc gcc acc cat cta aat acc ttg           3766
Asp Ala Leu Val Lys Ala Ser Asp Ile Ala Thr His Leu Asn Thr Leu
            1125                1130                1135 gct ggc gac atc caa acc gcc aaa gga gca agc caa gca agc agc tca           3814
Ala Gly Asp Ile Gln Thr Ala Lys Gly Ala Ser Gln Ala Ser Ser Ser
        1140                1145                1150 gca agc tat gtg gat gct gat ggc aac aag gtc atc tat gac agt acc           3862
Ala Ser Tyr Val Asp Ala Asp Gly Asn Lys Val Ile Tyr Asp Ser Thr
    1155                1160                1165 gat aag aag tac tat caa gcc aaa aat gat ggc aca gtt gat aaa acc           3910
Asp Lys Lys Tyr Tyr Gln Ala Lys Asn Asp Gly Thr Val Asp Lys Thr
1170                1175                1180                1185 aaa gaa gtt gcc aaa gac aaa ctg gtc gcc caa gcc caa acc cca gat           3958
Lys Glu Val Ala Lys Asp Lys Leu Val Ala Gln Ala Gln Thr Pro Asp
                1190                1195                1200 ggc aca ttg gct cga atg aat gtc aaa tca gtc att aac aaa gaa caa           4006
Gly Thr Leu Ala Arg Met Asn Val Lys Ser Val Ile Asn Lys Glu Gln
            1205                1210                1215 gta aat gat gcc aat aaa aag caa ggc atc aac gaa gac aac gcc ttt           4054
Val Asn Asp Ala Asn Lys Lys Gln Gly Ile Asn Glu Asp Asn Ala Phe
        1220                1225                1230 gtt aaa gga ctt gaa aaa gcc gct tct gat aac aaa acc aaa aac gcc           4102
Val Lys Gly Leu Glu Lys Ala Ala Ser Asp Asn Lys Thr Lys Asn Ala
    1235                1240                1245 gca gta act gtg ggt gat tta aat gcc gtt gcc caa aca ccg ctg acc           4150
Ala Val Thr Val Gly Asp Leu Asn Ala Val Ala Gln Thr Pro Leu Thr
1250                1255                1260                1265 ttt gca ggg gat aca ggc aca acg gct aaa aaa ctg ggc gag act ttg           4198
Phe Ala Gly Asp Thr Gly Thr Thr Ala Lys Lys Leu Gly Glu Thr Leu
                1270                1275                1280 acc atc aaa ggt ggg caa aca gac acc aat aag cta acc gat aat aac           4246
```

-continued

```
Thr Ile Lys Gly Gly Gln Thr Asp Thr Asn Lys Leu Thr Asp Asn Asn
        1285                1290                1295 atc ggt gtg gta gca ggt act gat ggc ttc act gtc aaa ctt gcc aaa      4294
Ile Gly Val Val Ala Gly Thr Asp Gly Phe Thr Val Lys Leu Ala Lys
        1300                1305                1310 gac cta acc aat ctt aac agc gtt aat gca ggt ggc acc aaa att gat      4342
Asp Leu Thr Asn Leu Asn Ser Val Asn Ala Gly Gly Thr Lys Ile Asp
        1315                1320                1325 gac aaa ggc gtg tct ttt gta gac gca aac ggt caa gcc aaa gca aac      4390
Asp Lys Gly Val Ser Phe Val Asp Ala Asn Gly Gln Ala Lys Ala Asn
1330                1335                1340                1345 acc cct gtg cta agt gcc aat ggg ctg gac ctg ggt ggc aaa cgc atc      4438
Thr Pro Val Leu Ser Ala Asn Gly Leu Asp Leu Gly Gly Lys Arg Ile
            1350                1355                1360 agt aac atc ggt gca gct gtt gat gat aac gat gcg gtg aac ttt aag      4486
Ser Asn Ile Gly Ala Ala Val Asp Asp Asn Asp Ala Val Asn Phe Lys
        1365                1370                1375 cag ttt aat gaa gtt gcc aaa acg gtc aac aac cta aac aac caa agt      4534
Gln Phe Asn Glu Val Ala Lys Thr Val Asn Asn Leu Asn Asn Gln Ser
        1380                1385                1390 aac tca ggt gcg tca ttg ccc ttt gta gta acc gat gcc aat ggc aag      4582
Asn Ser Gly Ala Ser Leu Pro Phe Val Val Thr Asp Ala Asn Gly Lys
        1395                1400                1405 ccc atc aat ggc acc gat gac aag ccc caa aaa gcc atc aag ggc gcc      4630
Pro Ile Asn Gly Thr Asp Asp Lys Pro Gln Lys Ala Ile Lys Gly Ala
1410                1415                1420                1425 gat ggt aaa tac tat cac gcc aac gcc aac ggc gta cct gtg gac aaa      4678
Asp Gly Lys Tyr Tyr His Ala Asn Ala Asn Gly Val Pro Val Asp Lys
            1430                1435                1440 gat ggc aac ccc atc acc gat gcg gac aaa ctt gcc aat ctg gca gct      4726
Asp Gly Asn Pro Ile Thr Asp Ala Asp Lys Leu Ala Asn Leu Ala Ala
        1445                1450                1455 cat ggc aaa ccc ctt gat gca ggt cat caa gtg gtg gca agc cta ggc      4774
His Gly Lys Pro Leu Asp Ala Gly His Gln Val Val Ala Ser Leu Gly
        1460                1465                1470 ggc aac tca gat gcc atc acc cta acc aac atc aag tcc act ttg cca      4822
Gly Asn Ser Asp Ala Ile Thr Leu Thr Asn Ile Lys Ser Thr Leu Pro
    1475                1480                1485 caa att gac aca cca aac aca ggt aat gcc aat gca ggg caa gcc caa      4870
Gln Ile Asp Thr Pro Asn Thr Gly Asn Ala Asn Ala Gly Gln Ala Gln
1490                1495                1500                1505 agt ctg ccc agc cta tca gca gca cag caa agt aat gct gcc agt gtc      4918
Ser Leu Pro Ser Leu Ser Ala Ala Gln Gln Ser Asn Ala Ala Ser Val
            1510                1515                1520 aaa gat gtg cta aat gta ggc ttt aac ttg cag acc aat cac aat caa      4966
Lys Asp Val Leu Asn Val Gly Phe Asn Leu Gln Thr Asn His Asn Gln
        1525                1530                1535 gtg gac ttt gtc aaa gcc tat gat acc gtc aac ttt gtc aat ggt aca      5014
Val Asp Phe Val Lys Ala Tyr Asp Thr Val Asn Phe Val Asn Gly Thr
        1540                1545                1550 ggt gcc gac atc aca agc gtg cgt agt gct gat ggc acg atg agt aac      5062
Gly Ala Asp Ile Thr Ser Val Arg Ser Ala Asp Gly Thr Met Ser Asn
    1555                1560                1565 atc acc gtc aac acc gcc tta gca gcg acc gat gat gat ggc aat gtg      5110
Ile Thr Val Asn Thr Ala Leu Ala Ala Thr Asp Asp Asp Gly Asn Val
1570                1575                1580                1585 ctt atc aaa gcc aaa gat ggt aag ttc tac aaa gca gac gac ctc atg      5158
Leu Ile Lys Ala Lys Asp Gly Lys Phe Tyr Lys Ala Asp Asp Leu Met
            1590                1595                1600 cca aac ggc tca cta aaa gca ggc aaa tca gcc agt gat gcc aaa act      5206
Pro Asn Gly Ser Leu Lys Ala Gly Lys Ser Ala Ser Asp Ala Lys Thr
```

-continued

```
Pro Asn Gly Ser Leu Lys Ala Gly Lys Ser Ala Ser Asp Ala Lys Thr
            1605                1610                1615 cca act ggt cta agc ctt gtc aac ccc aat gct ggt aaa ggc agt aca       5254
Pro Thr Gly Leu Ser Leu Val Asn Pro Asn Ala Gly Lys Gly Ser Thr
        1620                1625                1630 ggc gat gca gtg gct ctt aat aac tta tca aaa gcg gta ttt aaa tcc       5302
Gly Asp Ala Val Ala Leu Asn Asn Leu Ser Lys Ala Val Phe Lys Ser
    1635                1640                1645 aaa gat ggt aca act act acc aca gta agc tct gat ggc atc agt atc       5350
Lys Asp Gly Thr Thr Thr Thr Thr Val Ser Ser Asp Gly Ile Ser Ile
1650                1655                1660                1665 caa ggc aaa gat aac agc aac atc acc cta agc aaa gat ggg ctg aat       5398
Gln Gly Lys Asp Asn Ser Asn Ile Thr Leu Ser Lys Asp Gly Leu Asn
            1670                1675                1680 gta ggc ggt aag gtc atc agc aat gtg ggt aaa ggc aca aaa gac acc       5446
Val Gly Gly Lys Val Ile Ser Asn Val Gly Lys Gly Thr Lys Asp Thr
        1685                1690                1695 gac gct gcc aat gta caa cag tta aac cga agt acg caa ctt gtt ggg       5494
Asp Ala Ala Asn Val Gln Gln Leu Asn Arg Ser Thr Gln Leu Val Gly
    1700                1705                1710 tct tgg gta atg gct ggt aat gat aac gct gac ggc aat cag gta aac       5542
Ser Trp Val Met Ala Gly Asn Asp Asn Ala Asp Gly Asn Gln Val Asn
 1715                1720                1725 att gcc gac atc aaa aaa gac cca aat tca ggt tca tca tct aac cgc       5590
Ile Ala Asp Ile Lys Lys Asp Pro Asn Ser Gly Ser Ser Ser Asn Arg
1730                1735                1740                1745 act gtc atc aaa gca ggc acg gta ctt ggc ggt aaa ggt aat aac gat       5638
Thr Val Ile Lys Ala Gly Thr Val Leu Gly Gly Lys Gly Asn Asn Asp
            1750                1755                1760 acc gaa aaa ctt gcc act ggt ggt gta caa gtg ggc gtg gat aaa gac       5686
Thr Glu Lys Leu Ala Thr Gly Gly Val Gln Val Gly Val Asp Lys Asp
        1765                1770                1775 ggc aac gct aac ggc gat tta agc aat gtt tgg gtc aaa acc caa aaa       5734
Gly Asn Ala Asn Gly Asp Leu Ser Asn Val Trp Val Lys Thr Gln Lys
    1780                1785                1790 gat ggc agc aaa aaa gcc ctg ctc gcc act tat aac gcc gca ggt cag       5782
Asp Gly Ser Lys Lys Ala Leu Leu Ala Thr Tyr Asn Ala Ala Gly Gln
 1795                1800                1805 acc aac tat ttg acc aac aac ccc gca gaa gcc att gac aga ata aat       5830
Thr Asn Tyr Leu Thr Asn Asn Pro Ala Glu Ala Ile Asp Arg Ile Asn
1810                1815                1820                1825 gaa caa ggt atc cgc ttc ttc cat gtc aac gat ggc aat caa gag cct       5878
Glu Gln Gly Ile Arg Phe Phe His Val Asn Asp Gly Asn Gln Glu Pro
            1830                1835                1840 gtg gta caa ggg cgt aac ggc att gac tca agt gcc tca ggc aag cac       5926
Val Val Gln Gly Arg Asn Gly Ile Asp Ser Ser Ala Ser Gly Lys His
        1845                1850                1855 tca gtg gcg gtc ggt tat aag gcc aag gca gat ggt gaa gcc gcc gtt       5974
Ser Val Ala Val Gly Tyr Lys Ala Lys Ala Asp Gly Glu Ala Ala Val
    1860                1865                1870 gcc ata ggc aga caa acc caa gca ggc aac caa tcc atc gcc atc ggt       6022
Ala Ile Gly Arg Gln Thr Gln Ala Gly Asn Gln Ser Ile Ala Ile Gly
 1875                1880                1885 gat aac gca caa gcc aca ggc gat caa tcc atc gcc atc ggt aca ggc       6070
Asp Asn Ala Gln Ala Thr Gly Asp Gln Ser Ile Ala Ile Gly Thr Gly
1890                1895                1900                1905 aat gtg gta gca ggt aag cac tct ggt gcc atc ggc gac cca agc act       6118
Asn Val Val Ala Gly Lys His Ser Gly Ala Ile Gly Asp Pro Ser Thr
            1910                1915                1920 gtt aag gct gat aac agt tac agt gtg ggt aat aac aac cag ttt acc       6166
```

```
                Val Lys Ala Asp Asn Ser Tyr Ser Val Gly Asn Asn Gln Phe Thr
                    1925                1930                1935 gat gcc act cag acc gat gtc ttt ggt gtg ggc aat aac atc acc gtg        6214
Asp Ala Thr Gln Thr Asp Val Phe Gly Val Gly Asn Asn Ile Thr Val
        1940                1945                1950 acc gaa agt aac tcg gtt gcc tta ggt tca aac tct gcc atc agt gca        6262
Thr Glu Ser Asn Ser Val Ala Leu Gly Ser Asn Ser Ala Ile Ser Ala
    1955                1960                1965 ggc aca cac gca ggc aca caa gcc aaa aaa tct gac ggc aca gca ggt        6310
Gly Thr His Ala Gly Thr Gln Ala Lys Lys Ser Asp Gly Thr Ala Gly
1970                1975                1980                1985 aca acc acc aca gca ggt gca aca ggt acg gtt aaa ggc ttt gct gga        6358
Thr Thr Thr Thr Ala Gly Ala Thr Gly Thr Val Lys Gly Phe Ala Gly
                1990                1995                2000 caa acg gcg gtt ggt gcg gtc tcc gtg ggt gcc tca ggt gct gaa cgc        6406
Gln Thr Ala Val Gly Ala Val Ser Val Gly Ala Ser Gly Ala Glu Arg
            2005                2010                2015 cgt atc caa aat gtg gca gca ggt gag gtc agt gcc acc agc acc gat        6454
Arg Ile Gln Asn Val Ala Ala Gly Glu Val Ser Ala Thr Ser Thr Asp
        2020                2025                2030 gcg gtc aat ggt agc cag ttg tac aaa gcc acc caa agc att gcc aac        6502
Ala Val Asn Gly Ser Gln Leu Tyr Lys Ala Thr Gln Ser Ile Ala Asn
    2035                2040                2045 gca acc aat gag ctt gac cat cgt atc cac caa aac gaa aat aaa gcc        6550
Ala Thr Asn Glu Leu Asp His Arg Ile His Gln Asn Glu Asn Lys Ala
2050                2055                2060                2065 aat gca ggg att tca tca gcg atg gcg atg gcg tcc atg cca caa gcc        6598
Asn Ala Gly Ile Ser Ser Ala Met Ala Met Ala Ser Met Pro Gln Ala
                2070                2075                2080 tac att cct ggc aga tcc atg gtt acc ggg ggt att gcc acc cac aac        6646
Tyr Ile Pro Gly Arg Ser Met Val Thr Gly Gly Ile Ala Thr His Asn
            2085                2090                2095 ggt caa ggt gcg gtg gca gtg gga ctg tcg aag ctg tcg gat aat ggt        6694
Gly Gln Gly Ala Val Ala Val Gly Leu Ser Lys Leu Ser Asp Asn Gly
        2100                2105                2110 caa tgg gta ttt aaa atc aat ggt tca gcc gat acc caa ggc cat gta        6742
Gln Trp Val Phe Lys Ile Asn Gly Ser Ala Asp Thr Gln Gly His Val
    2115                2120                2125 ggg gca gca gtt ggt gca ggt ttt cac ttt taagccataa atcgcaagat          6792
Gly Ala Ala Val Gly Ala Gly Phe His Phe
2130                2135 tttacttaaa aatcaatctc accatagttg tataaaacag catcagcatc agtcatatta     6852
ctgatgcttg atggttttta ttacttaaac cattta                                6889

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgggatccga tggccgtggc ggaatatgcc                                        30

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 4
cgcggatccg aaaagtgaaa acctgcacca actgctgc                                  38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtcagcatg tatcattttt ttaaggtaaa ccaccatg                                  38

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catcaattgc gatatgtctg ggatcttg                                             28

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttcacccca tcagtgccat agacc                                                25

<210> SEQ ID NO 8
<211> LENGTH: 150
<212> TYPE: PRT
<213> ORGANISM: Moraxella catarrhalis

<400> SEQUENCE: 8

Ala Leu His Gly Ser Thr Ile Ser Asn Asp Lys Thr Arg Ala Ala
 1               5                  10                  15

Ser Ile Ala Asp Val Leu Asn Ala Gly Phe Asn Leu Glu Gly Asn Gly
             20                  25                  30

Glu Ala Val Asp Phe Val Ser Thr Tyr Asp Thr Val Asn Phe Ala Asp
         35                  40                  45

Gly Asn Ala Thr Thr Ala Lys Val Thr Tyr Asp Asn Lys Thr Ser Lys
     50                  55                  60

Val Ala Tyr Asp Val Asn Val Asp Gly Thr Thr Ile His Leu Thr Gly
 65                  70                  75                  80

Thr Asn Gly Lys Lys Asn Gln Ile Gly Val Lys Thr Thr Leu Thr
                 85                  90                  95

Thr Lys Arg Ala Lys Gly Asn Thr Ala Thr Asn Phe Ser Val Asn Ser
            100                 105                 110

Gly Asp Asn Ala Leu Ile Asn Ala Lys Ile Ala Asp Asn Leu
        115                 120                 125

Asn Thr Leu Ala Gly Glu Ile Arg Thr Ala Lys Gly Thr Ala Ser Thr
    130                 135                 140

Ala Leu Gln Thr Phe Ser
```

```
<210> SEQ ID NO 9
<211> LENGTH: 450
<212> TYPE: DNA
<213> ORGANISM: Moraxella catarrhalis

<400> SEQUENCE: 9
gcactacatg gcagtacaat ttctaacgac gacaaaaccc gtgccgccag tatcgccgat      60
gtgctaaacg caggctttaa cttggaaggt aatggtgaag cggttgactt tgtctccact     120
tatgacaccg tcaactttgc cgatggcaat gccaccaccg ctaaggtaac ttatgataac     180
aaaaccagta aagtggcgta tgatgtcaat gtggatggta caaccattca tctaacaggc     240
actaatggca agaaaaacca aattggcgta aaaaccacca cactgaccac aaaacgtgct     300
aaaggtaata cagcaactaa tttagtgtt aactctggtg atgacaatgc ccttattaac      360
gccaaagaca tcgccgacaa tctaaacacc ctagctggtg aaattcgcac cgccaaaggc     420
acagcaagca ccgccctaca aaccttctct                                      450

<210> SEQ ID NO 10
<211> LENGTH: 239
<212> TYPE: PRT
<213> ORGANISM: Moraxella catarrhalis

<400> SEQUENCE: 10

Asp Gln Thr Lys Gly Leu Thr Thr Pro Lys Leu Thr Val Gly Ser Ser
 1               5                  10                  15

Asn Gly Lys Gly Ile Val Ile Asp Ser Lys Asp Gly Gln Asn Thr Ile
            20                  25                  30

Thr Gly Leu Ser Asn Thr Leu Thr Asp Ala Thr Asn Ala Thr Thr Gly
        35                  40                  45

His Val Ser Glu Ile Gln Gly Leu Ala Gln Gly Ala Asn Lys Thr Arg
    50                  55                  60

Ala Ala Ser Ile Gly Asp Val Leu Asn Ala Gly Phe Asn Leu Gln Gly
65                  70                  75                  80

Asn Gly Glu Ala Lys Asp Phe Val Ser Thr Tyr Asp Thr Val Asn Phe
                85                  90                  95

Ile Asp Gly Asn Ala Thr Thr Ala Lys Val Thr Tyr Asp Asp Thr Lys
            100                 105                 110

Gln Thr Ser Thr Val Thr Tyr Asp Val Asn Val Asp Asn Lys Thr Leu
        115                 120                 125

Glu Val Thr Gly Asp Lys Lys Leu Gly Val Lys Thr Thr Leu Thr
    130                 135                 140

Lys Thr Ser Ala Asn Gly Asn Ala Thr Lys Phe Ser Ala Ala Asp Gly
145                 150                 155                 160

Asp Ala Leu Val Lys Ala Ser Asp Ile Ala Thr His Leu Asn Thr Leu
                165                 170                 175

Ala Gly Asp Ile Gln Thr Ala Lys Gly Ala Ser Gln Ala Ser Ser Ser
            180                 185                 190

Ala Ser Tyr Val Asp Ala Asp Gly Asn Lys Val Ile Tyr Asp Ser Thr
        195                 200                 205

Asp Lys Lys Tyr Gln Ala Leu Asn Asp Gly Thr Val Asp Lys Thr
    210                 215                 220

Lys Glu Val Ala Lys Asp Lys Leu Val Ala Gln Ala Gln Thr Pro
225                 230                 235
```

<210> SEQ ID NO 11
<211> LENGTH: 717
<212> TYPE: DNA
<213> ORGANISM: Moraxella catarrhalis

<400> SEQUENCE: 11

```
gaccaaacca aaggcttaac cacgcctaag ctgaccgtgg gtagtagtaa tggcaaaggc      60
attgtcattg acagtaaaga tggtcaaaat accatcacag gactaagcaa cactctaacc     120
gatgccacca acgcaacaac agggcatgtc agtgaaatcc agggcttggc acaaggtgca     180
aacaaaaccc gtgccgccag cattggtgat gtactaaacg caggctttaa cttgcaaggc     240
aatggtgaag ccaaagactt tgtctccact tatgacaccg tcaactttat cgatggcaat     300
gccaccaccg ctaaggtgac ctatgatgac acgaaacaga ccagcacagt aacttatgat     360
gtcaatgtgg ataataaaac ccttgaagtg acaggcgata aaaaacttgg cgtcaaaacc     420
accacactga ccaaaacaag tgctaatggt aatgcaacca aatttagtgc cgccgatggc     480
gatgcccttg ttaaagccag tgatatcgcc acccatctaa ataccttggc tggcgacatc     540
caaaccgcca aaggagcaag ccaagcaagc agctcagcaa gctatgtgga tgctgatggc     600
aacaaggtca tctatgacag taccgataag aagtactatc aagccaaaaa tgatggcaca     660
gttgataaaa ccaaagaagt tgccaaagac aaactggtcg cccaagccca aacccca        717
```

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Ala Gln Ala Asn Thr Glu Ser Ser Ile Ala Val Gly
1               5                   10

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Asn Thr Ala Thr Asn Phe Ser Val Asn Ser Gly Asp Asp Asn Ala
1               5                   10                  15

Leu Ile Asn

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gly Ile Asn Glu Asp Asn Ala Phe Val Lys Gly Leu Glu Lys
1               5                   10                  15

<210> SEQ ID NO 15
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 15

Pro Ser Thr Val Lys Ala Asp Asn
  1               5

<210> SEQ ID NO 16
<211> LENGTH: 1833
<212> TYPE: PRT
<213> ORGANISM: Moraxella catarrhalis

<400> SEQUENCE: 16

Met Ser Tyr Ala Gln Gly His Phe Ser Asn Ala Phe Gly Thr Arg Ala
  1               5                  10                  15

Thr Ala Lys Ser Ala Tyr Ser Leu Ala Val Gly Leu Ala Ala Thr Ala
                 20                  25                  30

Glu Gly Gln Ser Thr Ile Ala Ile Gly Ser Asp Ala Thr Ser Ser Ser
             35                  40                  45

Leu Gly Ala Ile Ala Leu Gly Ala Gly Thr Arg Ala Gln Leu Gln Gly
 50                  55                  60

Ser Ile Ala Leu Gly Gln Gly Ser Val Val Thr Gln Ser Asp Asn Asn
 65                  70                  75                  80

Ser Arg Pro Ala Tyr Thr Pro Asn Thr Gln Ala Leu Asp Pro Lys Phe
                 85                  90                  95

Gln Ala Thr Asn Asn Thr Lys Ala Gly Pro Leu Ser Ile Gly Ser Asn
            100                 105                 110

Ser Ile Lys Arg Lys Ile Ile Asn Val Gly Ala Gly Val Asn Lys Thr
        115                 120                 125

Asp Ala Val Asn Val Ala Gln Leu Glu Ala Val Val Lys Trp Ala Lys
130                 135                 140

Glu Arg Arg Ile Thr Phe Gln Gly Asp Asp Asn Ser Thr Asp Val Lys
145                 150                 155                 160

Ile Gly Leu Asp Asn Thr Leu Thr Ile Lys Gly Gly Ala Glu Thr Asn
                165                 170                 175

Ala Leu Thr Asp Asn Asn Ile Gly Val Val Lys Glu Ala Asp Asn Ser
            180                 185                 190

Gly Leu Lys Val Lys Leu Ala Lys Thr Leu Asn Asn Leu Thr Glu Val
        195                 200                 205

Asn Thr Thr Thr Leu Asn Ala Thr Thr Val Lys Val Gly Ser Ser
210                 215                 220

Ser Ser Thr Thr Ala Glu Leu Leu Ser Asp Ser Leu Thr Phe Thr Gln
225                 230                 235                 240

Pro Asn Thr Gly Ser Gln Ser Thr Ser Lys Thr Val Tyr Gly Val Asn
                245                 250                 255

Gly Val Lys Phe Thr Asn Asn Ala Glu Thr Ala Ala Ile Gly Thr
            260                 265                 270

Thr Arg Ile Thr Arg Asp Lys Ile Gly Phe Ala Arg Asp Gly Asp Val
        275                 280                 285

Asp Glu Lys Gln Ala Pro Tyr Leu Asp Lys Lys Gln Leu Lys Val Gly
290                 295                 300

Ser Val Ala Ile Thr Ile Asp Asn Gly Ile Asp Ala Gly Asn Lys Lys
305                 310                 315                 320

Ile Ser Asn Leu Ala Lys Gly Ser Ala Asn Asp Ala Val Thr Ile
                325                 330                 335
```

```
Glu Gln Leu Lys Ala Ala Lys Pro Thr Leu Asn Ala Gly Ala Gly Ile
            340                 345                 350

Ser Val Thr Pro Thr Glu Ile Ser Val Asp Ala Lys Ser Gly Asn Val
        355                 360                 365

Thr Ala Pro Thr Tyr Asn Ile Gly Val Lys Thr Thr Glu Leu Asn Ser
370                 375                 380

Asp Gly Thr Ser Asp Lys Phe Ser Val Lys Gly Ser Gly Thr Asn Asn
385                 390                 395                 400

Ser Leu Val Thr Ala Glu His Leu Ala Ser Tyr Leu Asn Glu Val Asn
            405                 410                 415

Arg Thr Ala Asp Ser Ala Leu Gln Ser Phe Thr Val Lys Glu Glu Asp
            420                 425                 430

Asp Asp Asp Ala Asn Ala Ile Thr Val Ala Lys Asp Thr Thr Lys Asn
        435                 440                 445

Ala Gly Ala Val Ser Ile Leu Lys Leu Lys Gly Lys Asn Gly Leu Thr
            450                 455                 460

Val Ala Thr Lys Lys Asp Gly Thr Val Thr Phe Gly Leu Ser Gln Asp
465                 470                 475                 480

Ser Gly Leu Thr Ile Gly Lys Ser Thr Leu Asn Asn Asp Gly Leu Thr
                485                 490                 495

Val Lys Asp Thr Asn Glu Gln Ile Gln Val Gly Ala Asn Gly Ile Lys
        500                 505                 510

Phe Thr Asn Val Asn Gly Ser Asn Pro Gly Thr Gly Ile Ala Asn Thr
            515                 520                 525

Ala Arg Ile Thr Arg Asp Lys Ile Gly Phe Ala Gly Ser Asp Gly Ala
            530                 535                 540

Val Asp Thr Asn Lys Pro Tyr Leu Asp Gln Asp Lys Leu Gln Val Gly
545                 550                 555                 560

Asn Val Lys Ile Thr Asn Thr Gly Ile Asn Ala Gly Lys Ala Ile
                565                 570                 575

Thr Gly Leu Ser Pro Thr Leu Pro Ser Ile Ala Asp Gln Ser Ser Arg
            580                 585                 590

Asn Ile Glu Leu Gly Asn Thr Ile Gln Asp Lys Asp Lys Ser Asn Ala
            595                 600                 605

Ala Ser Ile Asn Asp Ile Leu Asn Thr Gly Phe Asn Leu Lys Asn Asn
        610                 615                 620

Asn Asn Pro Ile Asp Phe Val Ser Thr Tyr Asp Ile Val Asp Phe Ala
625                 630                 635                 640

Asn Gly Asn Ala Thr Ala Thr Val Thr His Asp Thr Ala Asn Lys
            645                 650                 655

Thr Ser Lys Val Val Tyr Asp Val Asn Val Asp Asp Thr Thr Ile His
                660                 665                 670

Leu Thr Gly Thr Asp Asn Lys Lys Leu Gly Val Lys Thr Thr Lys
            675                 680                 685

Leu Asn Lys Thr Ser Ala Asn Gly Asn Thr Ala Thr Asn Phe Asn Val
        690                 695                 700

Asn Ser Ser Asp Glu Asp Ala Leu Val Asn Ala Lys Asp Ile Ala Glu
705                 710                 715                 720

Asn Leu Asn Thr Leu Ala Lys Glu Ile His Thr Thr Lys Gly Thr Ala
                725                 730                 735

Asp Thr Ala Leu Gln Thr Phe Thr Val Lys Lys Val Asp Glu Asn Asn
            740                 745                 750

Asn Ala Asp Asp Ala Asn Ala Ile Thr Val Gly Gln Lys Asn Ala Asn
        755                 760                 765
```

```
Asn Gln Val Asn Thr Leu Thr Leu Lys Gly Glu Asn Gly Leu Asn Ile
         770                 775                 780

Lys Thr Asp Lys Asn Gly Thr Val Thr Phe Gly Ile Asn Thr Thr Ser
785                 790                 795                 800

Gly Leu Lys Ala Gly Lys Ser Thr Leu Asn Asp Gly Gly Leu Ser Ile
             805                 810                 815

Lys Asn Pro Thr Gly Ser Glu Gln Ile Gln Val Gly Ala Asp Gly Val
         820                 825                 830

Lys Phe Ala Lys Val Asn Asn Gly Val Val Gly Ala Gly Ile Asp
     835                 840                 845

Gly Thr Thr Arg Ile Thr Arg Asp Glu Ile Gly Phe Thr Gly Thr Asn
         850                 855                 860

Gly Ser Leu Asp Lys Ser Lys Pro His Leu Ser Lys Asp Gly Ile Asn
865                 870                 875                 880

Ala Gly Gly Lys Lys Ile Thr Asn Ile Gln Ser Gly Glu Ile Ala Gln
             885                 890                 895

Asn Ser His Asp Ala Val Thr Gly Gly Lys Ile Tyr Asp Leu Lys Thr
         900                 905                 910

Glu Leu Glu Asn Lys Ile Ser Ser Thr Ala Lys Thr Ala Gln Asn Ser
         915                 920                 925

Leu His Glu Phe Ser Val Ala Asp Glu Gln Gly Asn Asn Phe Thr Val
         930                 935                 940

Ser Asn Pro Tyr Ser Ser Tyr Asp Thr Ser Lys Thr Ser Asp Val Ile
945                 950                 955                 960

Thr Phe Ala Gly Glu Asn Gly Ile Thr Thr Lys Val Asn Lys Gly Val
             965                 970                 975

Val Arg Val Gly Ile Asp Gln Thr Lys Gly Leu Thr Thr Pro Lys Leu
         980                 985                 990

Thr Val Gly Asn Asn Asn Gly Lys Gly Ile Val Ile Asp Ser Gln Asn
         995                1000                1005

Gly Gln Asn Thr Ile Thr Gly Leu Ser Asn Thr Leu Ala Asn Val Thr
     1010                1015                1020

Asn Asp Lys Gly Ser Val Arg Thr Thr Glu Gln Gly Asn Ile Ile Lys
1025                1030                1035                1040

Asp Glu Asp Lys Thr Arg Ala Ala Ser Ile Val Asp Val Leu Ser Ala
             1045                1050                1055

Gly Phe Asn Leu Gln Gly Asn Gly Glu Ala Val Asp Phe Val Ser Thr
         1060                1065                1070

Tyr Asp Thr Val Asn Phe Ala Asp Gly Asn Ala Thr Thr Ala Lys Val
         1075                1080                1085

Thr Tyr Asp Asp Thr Ser Lys Ser Lys Val Val Tyr Asp Val Asn
     1090                1095                1100

Val Asp Asp Thr Thr Ile Glu Val Lys Asp Lys Lys Leu Gly Val Lys
1105                1110                1115                1120

Thr Thr Thr Leu Thr Ser Thr Gly Thr Gly Ala Asn Lys Phe Ala Leu
             1125                1130                1135

Ser Asn Gln Ala Thr Gly Asp Ala Leu Val Lys Ala Ser Asp Ile Val
         1140                1145                1150

Ala His Leu Asn Thr Leu Ser Gly Asp Ile Gln Thr Ala Lys Gly Ala
         1155                1160                1165

Ser Gln Ala Asn Asn Ser Ala Gly Tyr Val Asp Ala Asp Gly Asn Lys
         1170                1175                1180

Val Ile Tyr Asp Ser Thr Asp Asn Lys Tyr Tyr Gln Ala Lys Asn Asp
```

```
                    1185              1190              1195              1200
Gly Thr Val Asp Lys Thr Lys Glu Val Ala Lys Asp Lys Leu Val Ala
                1205              1210              1215
Gln Ala Gln Thr Pro Asp Gly Thr Leu Ala Gln Met Asn Val Lys Ser
            1220              1225              1230
Val Ile Asn Lys Glu Gln Val Asn Asp Ala Asn Lys Lys Gln Gly Ile
        1235              1240              1245
Asn Glu Asp Asn Ala Phe Val Lys Gly Leu Glu Lys Ala Ala Ser Asp
    1250              1255              1260
Asn Lys Thr Lys Asn Ala Ala Val Thr Val Gly Asp Leu Asn Ala Val
1265              1270              1275              1280
Ala Gln Thr Pro Leu Thr Phe Ala Gly Asp Thr Gly Thr Thr Ala Lys
                1285              1290              1295
Lys Leu Gly Glu Thr Leu Thr Ile Lys Gly Gly Gln Thr Asp Thr Asn
            1300              1305              1310
Lys Leu Thr Asp Asn Asn Ile Gly Val Val Ala Gly Thr Asp Gly Phe
        1315              1320              1325
Thr Val Lys Leu Ala Lys Asp Leu Thr Asn Leu Asn Ser Val Asn Ala
    1330              1335              1340
Gly Gly Thr Lys Ile Asp Asp Lys Gly Val Ser Phe Val Asp Ser Ser
1345              1350              1355              1360
Gly Gln Ala Lys Ala Asn Thr Pro Val Leu Ser Ala Asn Gly Leu Asp
            1365              1370              1375
Leu Gly Gly Lys Val Ile Ser Asn Val Gly Lys Gly Thr Lys Asp Thr
        1380              1385              1390
Asp Ala Ala Asn Val Gln Gln Leu Asn Glu Val Arg Asn Leu Leu Gly
    1395              1400              1405
Leu Gly Asn Ala Gly Asn Asp Asn Ala Asp Gly Asn Gln Val Asn Ile
1410              1415              1420
Ala Asp Ile Lys Lys Asp Pro Asn Ser Gly Ser Ser Ser Asn Arg Thr
1425              1430              1435              1440
Val Ile Lys Ala Gly Thr Val Leu Gly Gly Lys Gly Asn Asn Asp Thr
            1445              1450              1455
Glu Lys Leu Ala Thr Gly Gly Ile Gln Val Gly Val Asp Lys Asp Gly
        1460              1465              1470
Asn Ala Asn Gly Asp Leu Ser Asn Val Trp Val Lys Thr Gln Lys Asp
    1475              1480              1485
Gly Ser Lys Lys Ala Leu Leu Ala Thr Tyr Asn Ala Ala Gly Gln Thr
    1490              1495              1500
Asn Tyr Leu Thr Asn Asn Pro Ala Glu Ala Ile Asp Arg Ile Asn Glu
1505              1510              1515              1520
Gln Gly Ile Arg Phe Phe His Val Asn Asp Gly Asn Gln Glu Pro Val
            1525              1530              1535
Val Gln Gly Arg Asn Gly Ile Asp Ser Ser Ala Ser Gly Lys His Ser
        1540              1545              1550
Val Ala Ile Gly Phe Gln Ala Lys Ala Asp Gly Glu Ala Ala Val Ala
    1555              1560              1565
Ile Gly Arg Gln Thr Gln Ala Gly Asn Gln Ser Ile Ala Ile Gly Asp
    1570              1575              1580
Asn Ala Gln Ala Thr Gly Asp Gln Ser Ile Ala Ile Gly Thr Gly Asn
1585              1590              1595              1600
Val Val Ala Gly Lys His Ser Gly Ala Ile Gly Asp Pro Ser Thr Val
            1605              1610              1615
```

-continued

```
Lys Ala Asp Asn Ser Tyr Ser Val Gly Asn Asn Asn Gln Phe Thr Asp
            1620                1625                1630

Ala Thr Gln Thr Asp Val Phe Gly Val Gly Asn Asn Ile Thr Val Thr
        1635                1640                1645

Glu Ser Asn Ser Val Ala Leu Gly Ser Asn Ser Ala Ile Ser Ala Gly
    1650                1655                1660

Thr His Ala Gly Thr Gln Ala Lys Lys Ser Asp Gly Thr Ala Gly Thr
1665                1670                1675                1680

Thr Thr Thr Ala Gly Ala Thr Gly Thr Val Lys Gly Phe Ala Gly Gln
            1685                1690                1695

Thr Ala Val Gly Ala Val Ser Val Gly Ala Ser Gly Ala Glu Arg Arg
            1700                1705                1710

Ile Gln Asn Val Ala Ala Gly Glu Val Ser Ala Thr Ser Thr Asp Ala
        1715                1720                1725

Val Asn Gly Ser Gln Leu Tyr Lys Ala Thr Gln Ser Ile Ala Asn Ala
    1730                1735                1740

Thr Asn Glu Leu Asp His Arg Ile His Gln Asn Glu Asn Lys Ala Asn
1745                1750                1755                1760

Ala Gly Ile Ser Ser Ala Met Ala Met Ala Ser Met Pro Gln Ala Tyr
            1765                1770                1775

Ile Pro Gly Arg Ser Met Val Thr Gly Gly Ile Ala Thr His Asn Gly
            1780                1785                1790

Gln Gly Ala Val Ala Val Gly Leu Ser Lys Leu Ser Asp Asn Gly Gln
        1795                1800                1805

Trp Val Phe Lys Ile Asn Gly Ser Ala Asp Thr Gln Gly His Val Gly
    1810                1815                1820

Ala Ala Val Gly Ala Gly Phe His Phe
1825                1830
```